United States Patent
Jackson et al.

(10) Patent No.: US 9,622,928 B2
(45) Date of Patent: Apr. 18, 2017

(54) RADIOLUCENT HINGE FOR A SURGICAL TABLE

(71) Applicant: Roger P. Jackson, Prairie Village, KS (US)

(72) Inventors: Roger P. Jackson, Prairie Village, KS (US); Lawrence E. Guerra, Mission, KS (US); Trevor A. Waggoner, Kansas City, KS (US)

(73) Assignee: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 14/792,280

(22) Filed: Jul. 6, 2015

(65) Prior Publication Data

US 2016/0000629 A1    Jan. 7, 2016

Related U.S. Application Data

(60) Provisional application No. 62/021,481, filed on Jul. 7, 2014, provisional application No. 62/118,282, filed
(Continued)

(51) Int. Cl.
*A61G 13/04* (2006.01)
*A61G 13/02* (2006.01)
(Continued)

(52) U.S. Cl.
CPC ............ *A61G 7/015* (2013.01); *A61B 6/0407* (2013.01); *A61G 13/02* (2013.01); *A61G 13/04* (2013.01);
(Continued)

(58) Field of Classification Search
CPC ........ A61G 7/015; A61G 7/018; A61G 13/02; A61G 13/004; A61G 13/04; A61G 13/06; A61G 13/08; A61G 13/10
See application file for complete search history.

(56) References Cited

U.S. PATENT DOCUMENTS 377,377 A    2/1888  Ferry
392,743 A *  11/1888  Millen .................. A61G 7/015
                                                    5/604
(Continued)

FOREIGN PATENT DOCUMENTS

CN    2467091 Y    12/2001
EP    2226010 B1    6/2014
(Continued)

OTHER PUBLICATIONS

Brochure of Smith & Nephew on Spinal Positioning System, 2003, 2004.
(Continued)

*Primary Examiner* — David E Sosnowski
*Assistant Examiner* — Ifeolu Adeboyejo
(74) *Attorney, Agent, or Firm* — Polsinelli PC

(57) ABSTRACT

A surgical table including a patient support including a head end section including a pair of head end frames joined with a foot end section including a pair of foot end frames, each of the head end frames is inwardly joined with one of the foot end frames at a hinge. Each of the hinges including a drive chain positioned within the foot end frame and including a plurality of drive links coupled together, the drive chain coupled at opposite ends to a sprocket and a drive link, the sprocket being rotatably coupled with the head end section via a hinge pin. The drive link operably coupled with a motor to move the drive link within the foot end frame so as to move the drive chain and cause the sprocket to rotate such that the head end section articulates relative to the foot end section about the hinge pins.

15 Claims, 80 Drawing Sheets

Related U.S. Application Data on Feb. 19, 2015, provisional application No. 62/118,305, filed on Feb. 19, 2015, provisional application No. 62/021,630, filed on Jul. 7, 2014, provisional application No. 62/021,643, filed on Jul. 7, 2014, provisional application No. 62/021,595, filed on Jul. 7, 2014.

(51) Int. Cl.
| | | |
|---|---|---|
| *A61G 13/06* | (2006.01) | |
| *A61G 13/08* | (2006.01) | |
| *A61G 7/015* | (2006.01) | |
| *A61B 6/04* | (2006.01) | |
| *A61G 13/10* | (2006.01) | |
| *E05D 9/00* | (2006.01) | |
| *E05D 11/00* | (2006.01) | |
| *A61G 13/12* | (2006.01) | |

(52) U.S. Cl.
CPC ............. *A61G 13/06* (2013.01); *A61G 13/08* (2013.01); *A61G 13/10* (2013.01); *A61G 13/104* (2013.01); *A61G 13/122* (2013.01); *A61G 13/123* (2013.01); *E05D 9/00* (2013.01); *E05D 11/0054* (2013.01); *A61G 2200/327* (2013.01); *E05D 2011/0072* (2013.01)

(56) References Cited

U.S. PATENT DOCUMENTS

| | | | |
|---|---|---|---|
| 430,635 A * | 6/1890 | Fox | A61G 7/015 5/617 |
| 987,423 A * | 3/1911 | Barnett | A61G 7/015 5/618 |
| 1,046,430 A * | 12/1912 | Beitz | A61G 7/015 5/282.1 |
| 1,098,477 A | 6/1914 | Cashman | |
| 1,143,618 A * | 6/1915 | Ewald | A61G 7/015 5/282.1 |
| 1,160,451 A | 11/1915 | Sanford | |
| 1,171,713 A | 2/1916 | Gilkerson | |
| 1,356,467 A * | 10/1920 | Payne | A61G 7/015 5/618 |
| 1,404,482 A * | 1/1922 | Sawyer | A61G 7/015 5/618 |
| 1,482,439 A | 2/1924 | McCullough | |
| 1,528,835 A | 3/1925 | McCullough | |
| 1,667,982 A | 5/1928 | Pearson | |
| 1,780,399 A | 11/1930 | Munson | |
| 1,799,692 A | 4/1931 | Knott | |
| 1,938,006 A | 12/1933 | Blanchard | |
| 1,990,357 A | 2/1935 | Ward | |
| 2,188,592 A | 1/1940 | Hosken et al. | |
| 2,261,297 A | 11/1941 | Frederick | |
| 2,411,768 A | 11/1946 | Welch | |
| 2,475,003 A | 7/1949 | Black | |
| 2,636,793 A * | 4/1953 | Meyer | A61B 6/04 378/209 |
| 2,688,410 A | 9/1954 | Nelson | |
| 2,792,945 A | 5/1957 | Brenny | |
| 2,807,322 A * | 9/1957 | Toti | E06B 9/362 160/168.1 V |
| 3,046,071 A | 7/1962 | Shampaine et al. | |
| 3,049,726 A | 8/1962 | Getz | |
| 3,281,141 A | 10/1966 | Smiley et al. | |
| 3,302,218 A | 2/1967 | Stryker | |
| 3,584,321 A | 6/1971 | Buchanan | |
| 3,599,964 A | 8/1971 | Magni | |
| 3,640,416 A | 2/1972 | Temple | |
| 3,766,384 A | 10/1973 | Anderson | |
| 3,814,414 A | 6/1974 | Chapa | |
| 3,827,089 A | 8/1974 | Grow | |
| 3,832,742 A | 9/1974 | Stryker | |
| 3,937,054 A | 2/1976 | Hortvet et al. | |
| 3,988,790 A | 11/1976 | Mracek et al. | |
| 4,101,120 A | 7/1978 | Seshima | |
| 4,131,802 A | 12/1978 | Braden et al. | |
| 4,144,880 A | 3/1979 | Daniels | |
| 4,148,472 A | 4/1979 | Rais et al. | |
| 4,175,550 A | 11/1979 | Leininger et al. | |
| 4,186,917 A | 2/1980 | Rais et al. | |
| 4,227,269 A | 10/1980 | Johnston | |
| 4,230,100 A | 10/1980 | Moon | |
| 4,244,358 A | 1/1981 | Pyers | |
| 4,292,962 A | 10/1981 | Krause | |
| 4,391,438 A | 7/1983 | Heffington, Jr. | |
| 4,435,861 A | 3/1984 | Lindley | |
| 4,474,364 A | 10/1984 | Brendgord | |
| 4,503,844 A | 3/1985 | Siczek | |
| 4,552,346 A | 11/1985 | Schnelle et al. | |
| 4,559,670 A * | 12/1985 | Wyatt | E06B 9/362 16/87.2 |
| 4,712,781 A | 12/1987 | Watanabe | |
| 4,715,073 A | 12/1987 | Butler | |
| 4,718,077 A | 1/1988 | Moore et al. | |
| 4,763,643 A | 8/1988 | Vrzalik | |
| 4,771,785 A | 9/1988 | Duer | |
| 4,799,527 A * | 1/1989 | Villoch | E06B 9/36 160/168.1 V |
| 4,830,337 A * | 5/1989 | Ichiro | B23Q 7/1431 254/95 |
| 4,834,163 A * | 5/1989 | Dickstein | E06B 9/361 160/176.1 R |
| 4,850,775 A | 7/1989 | Lee et al. | |
| 4,862,529 A | 9/1989 | Peck | |
| 4,872,656 A | 10/1989 | Brendgord et al. | |
| 4,872,657 A | 10/1989 | Lussi | |
| 4,887,325 A | 12/1989 | Tesch | |
| 4,937,901 A | 7/1990 | Brennan | |
| 4,939,801 A | 7/1990 | Schaal et al. | |
| 4,944,500 A | 7/1990 | Mueller et al. | |
| 4,953,245 A | 9/1990 | Jung | |
| 4,970,737 A | 11/1990 | Sagel | |
| 4,989,848 A | 2/1991 | Monroe | |
| 5,013,018 A | 5/1991 | Sicek et al. | |
| 5,088,706 A | 2/1992 | Jackson | |
| 5,131,103 A | 7/1992 | Thomas et al. | |
| 5,131,105 A | 7/1992 | Harrawood et al. | |
| 5,131,106 A | 7/1992 | Jackson | |
| 5,161,267 A | 11/1992 | Smith | |
| 5,163,890 A | 11/1992 | Perry, Jr. | |
| 5,181,289 A | 1/1993 | Kassai | |
| 5,208,928 A | 5/1993 | Kuck et al. | |
| 5,210,887 A | 5/1993 | Kershaw | |
| 5,210,888 A | 5/1993 | Canfield | |
| 5,230,112 A | 7/1993 | Harrawood et al. | |
| 5,231,741 A | 8/1993 | Maguire | |
| 5,239,716 A | 8/1993 | Fisk | |
| 5,274,862 A | 1/1994 | Palmer, Jr. | |
| 5,291,946 A * | 3/1994 | Ciriaci | E06B 9/362 160/177 R |
| 5,294,179 A | 3/1994 | Rudes et al. | |
| 5,333,334 A | 8/1994 | Kassai | |
| 5,393,018 A | 2/1995 | Roth et al. | |
| 5,407,008 A * | 4/1995 | Boloix | E06B 9/364 160/177 V |
| 5,444,882 A | 8/1995 | Andrews et al. | |
| 5,461,740 A | 10/1995 | Pearson | |
| 5,468,216 A | 11/1995 | Johnson et al. | |
| 5,487,195 A | 1/1996 | Ray | |
| 5,499,408 A | 3/1996 | Nix | |
| 5,524,304 A | 6/1996 | Shutes | |
| 5,544,371 A | 8/1996 | Fuller | |
| 5,579,550 A | 12/1996 | Bathrick et al. | |
| 5,588,705 A | 12/1996 | Chang | |
| 5,613,254 A | 3/1997 | Clayman et al. | |
| 5,640,730 A | 6/1997 | Godette | |
| 5,645,079 A | 7/1997 | Zahiri et al. | |
| 5,658,315 A | 8/1997 | Lamb et al. | |
| 5,659,909 A | 8/1997 | Pfeuffer et al. | |
| 5,673,443 A | 10/1997 | Marmor | |

(56) References Cited

U.S. PATENT DOCUMENTS

| | | | |
|---|---|---|---|
| 5,737,781 A | 4/1998 | Votel | |
| 5,754,997 A | 5/1998 | Lussi et al. | |
| 5,774,914 A | 7/1998 | Johnson et al. | |
| 5,794,286 A | 8/1998 | Scott et al. | |
| 5,829,077 A | 11/1998 | Neige | |
| 5,862,549 A | 1/1999 | Morton et al. | |
| 5,870,784 A | 2/1999 | Elliott | |
| 5,890,238 A | 4/1999 | Votel | |
| 5,901,388 A | 5/1999 | Cowan | |
| 5,937,456 A | 8/1999 | Norris | |
| 5,940,911 A * | 8/1999 | Wang | A47C 19/045 5/147 |
| 5,996,151 A | 12/1999 | Bartow et al. | |
| 6,000,076 A | 12/1999 | Webster et al. | |
| 6,035,465 A | 3/2000 | Rogozinski | |
| 6,049,923 A | 4/2000 | Ochiai | |
| 6,058,532 A | 5/2000 | Allen | |
| 6,109,424 A * | 8/2000 | Doan | B62D 65/02 198/468.8 |
| 6,212,713 B1 | 4/2001 | Kuck et al. | |
| 6,224,037 B1 * | 5/2001 | Novick | B66F 3/06 254/95 |
| 6,240,582 B1 | 6/2001 | Reinke | |
| 6,260,220 B1 | 7/2001 | Lamb et al. | |
| 6,282,736 B1 | 9/2001 | Hand et al. | |
| 6,282,738 B1 | 9/2001 | Heimbrock et al. | |
| 6,286,164 B1 | 9/2001 | Lamb et al. | |
| 6,287,241 B1 | 9/2001 | Ellis | |
| 6,295,666 B1 * | 10/2001 | Takaura | A61G 7/001 5/611 |
| 6,295,671 B1 | 10/2001 | Reesby et al. | |
| 6,315,564 B1 | 11/2001 | Levisman | |
| 6,322,251 B1 | 11/2001 | Ballhaus et al. | |
| 6,438,777 B1 | 8/2002 | Bender | |
| 6,496,991 B1 | 12/2002 | Votel | |
| 6,499,162 B1 | 12/2002 | Lu | |
| 6,505,365 B1 | 1/2003 | Hanson et al. | |
| 6,526,610 B1 | 3/2003 | Hand et al. | |
| 6,634,043 B2 | 10/2003 | Lamb et al. | |
| 6,638,299 B2 | 10/2003 | Cox | |
| 6,662,388 B2 | 12/2003 | Friel | |
| 6,668,396 B2 | 12/2003 | Wei | |
| 6,681,423 B2 | 1/2004 | Zachrisson | |
| 6,701,553 B1 | 3/2004 | Hand et al. | |
| 6,779,210 B1 | 8/2004 | Kelly | |
| 6,791,997 B2 | 9/2004 | Beyer et al. | |
| 6,794,286 B2 | 9/2004 | Aoyama et al. | |
| 6,817,363 B2 | 11/2004 | Biondo et al. | |
| 6,854,137 B2 | 2/2005 | Johnson | |
| 6,857,144 B1 | 2/2005 | Huang | |
| 6,862,759 B2 | 3/2005 | Hand et al. | |
| 6,885,165 B2 | 4/2005 | Henley et al. | |
| 6,971,131 B2 | 12/2005 | Bannister | |
| 6,971,997 B1 | 12/2005 | Ryan et al. | |
| 7,003,828 B2 | 2/2006 | Roussy | |
| 7,055,195 B2 | 6/2006 | Roussy | |
| 7,089,612 B2 | 8/2006 | Rocher et al. | |
| 7,103,931 B2 | 9/2006 | Somasundaram et al. | |
| 7,137,160 B2 | 11/2006 | Hand et al. | |
| 7,152,261 B2 | 12/2006 | Jackson | |
| 7,171,709 B2 | 2/2007 | Weismiller | |
| 7,189,214 B1 | 3/2007 | Saunders | |
| 7,197,778 B2 | 4/2007 | Sharps | |
| 7,213,279 B2 | 5/2007 | Weismiller et al. | |
| 7,234,180 B2 | 6/2007 | Horton et al. | |
| 7,290,302 B2 | 11/2007 | Sharps | |
| 7,331,557 B2 | 2/2008 | Dewert | |
| 7,343,635 B2 | 3/2008 | Jackson | |
| 7,428,760 B2 | 9/2008 | McCrimmon | |
| 7,552,490 B2 | 6/2009 | Saracen et al. | |
| 7,565,708 B2 | 7/2009 | Jackson | |
| 7,596,820 B2 | 10/2009 | Nielsen et al. | |
| 7,653,953 B2 | 2/2010 | Lopez-Sansalvador | |
| 7,669,262 B2 | 3/2010 | Skripps et al. | |
| 7,739,762 B2 | 6/2010 | Lamb et al. | |
| 7,874,695 B2 | 1/2011 | Jensen | |
| 8,056,163 B2 | 11/2011 | Lemire et al. | |
| 8,060,960 B2 | 11/2011 | Jackson | |
| 8,381,331 B2 | 2/2013 | Sharps et al. | |
| 8,584,281 B2 | 11/2013 | Diel et al. | |
| 8,635,725 B2 | 1/2014 | Tannoury et al. | |
| 8,677,529 B2 * | 3/2014 | Jackson | A61G 13/08 5/600 |
| 8,707,476 B2 | 4/2014 | Sharps | |
| 8,707,484 B2 | 4/2014 | Jackson | |
| 8,719,979 B2 | 5/2014 | Jackson | |
| 8,826,474 B2 | 9/2014 | Jackson | |
| 8,826,475 B2 | 9/2014 | Jackson | |
| 8,839,471 B2 | 9/2014 | Jackson | |
| 8,844,077 B2 | 9/2014 | Jackson et al. | |
| 8,856,986 B2 | 10/2014 | Jackson | |
| D720,076 S | 12/2014 | Sharps et al. | |
| 8,938,826 B2 | 1/2015 | Jackson | |
| 8,978,180 B2 | 3/2015 | Jackson | |
| 9,180,062 B2 | 11/2015 | Jackson | |
| 9,186,291 B2 | 11/2015 | Jackson et al. | |
| 9,198,817 B2 | 12/2015 | Jackson | |
| 9,205,013 B2 | 12/2015 | Jackson | |
| 9,211,223 B2 | 12/2015 | Jackson | |
| 9,265,680 B2 | 2/2016 | Sharps et al. | |
| 9,295,433 B2 | 3/2016 | Jackson et al. | |
| 2001/0037524 A1 | 11/2001 | Truwit | |
| 2002/0170116 A1 * | 11/2002 | Borders | A61B 6/0457 5/600 |
| 2003/0074735 A1 | 4/2003 | Zachrisson | |
| 2003/0145383 A1 | 8/2003 | Schwaegerle | |
| 2004/0098804 A1 | 5/2004 | Varadharajulu et al. | |
| 2004/0133983 A1 | 7/2004 | Newkirk et al. | |
| 2004/0168253 A1 | 9/2004 | Hand et al. | |
| 2004/0219002 A1 | 11/2004 | Lenaers | |
| 2006/0248650 A1 | 11/2006 | Skripps | |
| 2007/0056105 A1 | 3/2007 | Hyre et al. | |
| 2007/0107126 A1 | 5/2007 | Koch et al. | |
| 2007/0157385 A1 * | 7/2007 | Lemire | A61G 7/005 5/600 |
| 2007/0174965 A1 * | 8/2007 | Lemire | A61G 7/005 5/600 |
| 2007/0192960 A1 * | 8/2007 | Jackson | A61G 7/001 5/618 |
| 2007/0266516 A1 | 11/2007 | Cakmak | |
| 2008/0216241 A1 | 9/2008 | Mangiardi | |
| 2009/0126116 A1 * | 5/2009 | Lamb | A61G 13/08 5/619 |
| 2010/0037397 A1 | 2/2010 | Wood | |
| 2010/0107790 A1 | 5/2010 | Yamaguchi | |
| 2010/0192300 A1 | 8/2010 | Tannoury et al. | |
| 2010/0223728 A1 | 9/2010 | Hutchison | B66F 3/06 5/610 |
| 2011/0107517 A1 | 5/2011 | Lamb et al. | |
| 2011/0197361 A1 * | 8/2011 | Hornbach | A61G 7/012 5/618 |
| 2012/0005832 A1 * | 1/2012 | Turner | A61G 7/015 5/600 |
| 2012/0144589 A1 | 6/2012 | Skripps et al. | |
| 2012/0174319 A1 | 7/2012 | Menkedick | |
| 2012/0198625 A1 * | 8/2012 | Jackson | A61G 7/001 5/601 |
| 2012/0246829 A1 | 10/2012 | Lamb et al. | |
| 2012/0246830 A1 | 10/2012 | Hornbach | |
| 2013/0111666 A1 * | 5/2013 | Jackson | A61G 13/0036 5/601 |
| 2013/0133137 A1 * | 5/2013 | Jackson | A61G 13/08 5/617 |
| 2013/0198958 A1 | 8/2013 | Jackson et al. | |
| 2013/0205500 A1 | 8/2013 | Jackson | |
| 2013/0219623 A1 | 8/2013 | Jackson | |
| 2013/0254995 A1 | 10/2013 | Jackson | |
| 2013/0254996 A1 | 10/2013 | Jackson | |
| 2013/0269710 A1 | 10/2013 | Hight et al. | |
| 2013/0282234 A1 | 10/2013 | Roberts et al. | |
| 2013/0312181 A1 | 11/2013 | Jackson et al. | |
| 2013/0312187 A1 | 11/2013 | Jackson | |

(56) References Cited

U.S. PATENT DOCUMENTS

| | | | |
|---|---|---|---|
| 2013/0312188 A1* | 11/2013 | Jackson | A61G 7/015 5/618 |
| 2013/0326813 A1 | 12/2013 | Jackson | |
| 2014/0007349 A1 | 1/2014 | Jackson | |
| 2014/0020181 A1 | 1/2014 | Jackson | |
| 2014/0033436 A1 | 2/2014 | Jackson | |
| 2014/0068861 A1 | 3/2014 | Jackson et al. | |
| 2014/0082842 A1 | 3/2014 | Jackson | |
| 2014/0109316 A1 | 4/2014 | Jackson et al. | |
| 2014/0173826 A1 | 6/2014 | Jackson | |
| 2014/0196212 A1 | 7/2014 | Jackson | |
| 2014/0201913 A1 | 7/2014 | Jackson | |
| 2014/0201914 A1 | 7/2014 | Jackson | |
| 2014/0208512 A1 | 7/2014 | Jackson | |
| 2014/0317847 A1 | 10/2014 | Jackson | |
| 2015/0007391 A1 | 1/2015 | Xu | |
| 2015/0059094 A1 | 3/2015 | Jackson | |
| 2015/0113733 A1 | 4/2015 | Diel et al. | |
| 2015/0150743 A1 | 6/2015 | Jackson | |
| 2016/0000620 A1 | 1/2016 | Koch | |
| 2016/0000621 A1 | 1/2016 | Jackson et al. | |
| 2016/0000626 A1 | 1/2016 | Jackson et al. | |
| 2016/0000627 A1 | 1/2016 | Jackson et al. | |
| 2016/0000629 A1 | 1/2016 | Jackson et al. | |
| 2016/0008201 A1 | 1/2016 | Jackson et al. | |
| 2016/0038364 A1 | 2/2016 | Jackson | |
| 2016/0136027 A1 | 5/2016 | Jackson | |
| 2016/0166452 A1 | 6/2016 | Jackson et al. | |
| 2016/0213542 A1 | 7/2016 | Jackson | |

FOREIGN PATENT DOCUMENTS

| | | |
|---|---|---|
| GB | 569758 | 6/1945 |
| GB | 810956 | 3/1959 |
| JP | S53763 | 1/1978 |
| JP | 2000-060995 | 2/2000 |
| JP | 2000-116733 | 4/2000 |
| WO | WO99/07320 | 2/1999 |
| WO | WO 00/07537 | 2/2000 |
| WO | WO00/62731 | 10/2000 |
| WO | WO01/60308 | 8/2001 |
| WO | WO 02/078589 A1 | 10/2002 |
| WO | WO03/070145 | 8/2003 |
| WO | WO 2007/130679 A2 | 11/2007 |
| WO | WO2009/054969 | 4/2009 |
| WO | WO2009/100692 | 8/2009 |
| WO | WO2010/051303 A1 | 5/2010 |

OTHER PUBLICATIONS

Complaint for Patent Infringement, *Jackson v. Mizuho Orthopedic Sys., Inc.*, No. 4:12-CV-01031 (W.D. Mo. Aug. 7, 2012).
First Amended Complaint for Patent Infringement and Correction of Inventorship, *Jackson v. Mizuho Orthopedic Sys., Inc.*, No. 4:12-CV-01031 (W.D. Mo. Sep. 21, 2012).
Defendant Mizuho Orthopedic Systems, Inc.'s Answer to First Amended Complaint and Counterclaims, *Jackson v. Mizuho Orthopedic Sys., Inc.*, No. 4:12-CV-01031 (W.D. Mo. Nov. 1, 2012).
Plaintiff Roger P. Jackson, MD's, Reply to Counterclaims, *Jackson v. Mizuho Orthopedic Sys., Inc.*, No. 4:12-CV-01031 (W.D. Mo. Nov. 26, 2012).
Roger P. Jackson's Disclosure of Asserted Claims and Preliminary Infringement Contentions, *Jackson v. Mizuho Orthopedic Sys., Inc.*, No. 4:12-CV-01031 (W.D. Mo. Jan. 4, 2013).
Second Amended Complaint for Patent Infringement, for Correction of Inventorship, for Breach of a Non-Disclosure and Confidentiality Agreement, and for Misappropriation of Dr. Jackson's Right of Publicity, *Jackson v. Mizuho Orthopedic Sys., Inc.*, No. 4:12-CV-01031 (W.D. Mo. Jan. 28, 2013).
Defendant Mizuho Orthopedic Systems, Inc.'s Answer to Second Amended Complaint and Counterclaims, *Jackson v. Mizuho Orthopedic Sys., Inc.*, No. 4:12-CV-01031 (W.D. Mo. Feb. 19, 2013).
Defendant Mizuho Osi's Invalidity Contentions Pursuant to the Parties' Joint Scheduling Order, *Jackson v. Mizuho Orthopedic Sys., Inc.*, No. 4:12-CV-01031 (W.D. Mo. Feb. 22, 2013).
Plaintiff Roger P. Jackson, MD's, Reply to Second Counterclaims, *Jackson v. Mizuho Orthopedic Sys., Inc.*, No. 4:12-CV-01031 (W.D. Mo. Mar. 12, 2013).
Roger P. Jackson, MD's Disclosure of Proposed Terms to Be Construed, *Jackson v. Mizuho Orthopedic Sys., Inc.*, No. 4:12-CV-01031 (W.D. Mo. Apr. 5, 2013).
Defendant Mizuho Orthopedic Systems, Inc.'s Disclosure of Proposed Terms and Claim Elements for Construction, *Jackson v. Mizuho Orthopedic Sys., Inc.*, No. 4:12-CV-01031 (W.D. Mo. Apr. 5, 2013).
Mizuho Orthopedic Systems, Inc.'s Disclosure of Proposed Claim Constructions and Extrinsic Evidence, *Jackson v. Mizuho Orthopedic Sys., Inc.*, No. 4:12-CV-01031 (W.D. Mo. May 13, 2013).
Plaintiff Roger P. Jackson, MD's Disclosure of Preliminary Proposed Claim Constructions, *Jackson v. Mizuho Orthopedic Sys., Inc.*, No. 4:12-CV-01031 (W.D. Mo. May 13, 2013).
Defendant Mizuho Osi's Amended Invalidity Contentions Pursuant to the Parties' Joint Scheduling Order, *Jackson v. Mizuho Orthopedic Sys., Inc.*, No. 4:12-CV-01031 (W.D. Mo. May 15, 2013).
Joint Claim Construction Chart and Joint Prehearing Statement, *Jackson v. Mizuho Orthopedic Sys., Inc.*, No. 4:12-CV-01031 (W.D. Mo. Jun. 7, 2013).
Defendant Mizuho Orthopedic Systems, Inc.'s Objections and Responses to Plaintiff's First Set of Interrogatories, *Jackson v. Mizuho Orthopedic Sys., Inc.*, No. 4:12-Cv-01031 (W.D. Mo. Jun. 24, 2013).
Defendant Mizuho Orthopedic Systems, Inc.'s Opening Claim Construction Brief, *Jackson v. Mizuho Orthopedic Sys., Inc.*, No. 4:12-CV-01031 (W.D. Mo. Jul. 31, 2013).
Plaintiff Roger P. Jackson, MD's Opening Claim Construction Brief, *Jackson v. Mizuho Orthopedic Sys., Inc.*, No. 4:12-CV-01031 (W.D. Mo. Jul. 31, 2013).
Appendix A Amended Infringement Contentions Claim Chart for Mizuho's Axis System Compared to U.S. Pat. No. 7,565,708, *Jackson v. Mizuho Orthopedic Sys., Inc.*, No. 4:12-CV-01031 (W.D. Mo. Aug. 12, 2013).
Appendix B Amended Infringement Contentions Claim Chart for Mizuho's Axis System Compared to U.S. Pat. No. 8,060,960, *Jackson v. Mizuho Orthopedic Sys., Inc.*, No. 4:12-CV-01031 (W.D. Mo. Aug. 12, 2013).
Appendix C Amended Infringement Contentions Claim Chart for Mizuho's Proaxis System Compared to U.S. Pat. No. 7,565,708, *Jackson v. Mizuho Orthopedic Sys., Inc.*, No. 4:12-CV-01031 (W.D. Mo. Aug. 12, 2013).
Appendix D Amended Infringement Contentions Claim Chart for Mizuho's Proaxis System Compared to U.S. Pat. No. 8,060,960, *Jackson v. Mizuho Orthopedic Sys., Inc.*, No. 4:12-CV-01031 (W.D. Mo. Aug. 12, 2013).
Plaintiff Roger P. Jackson, MD's Responsive Claim Construction Brief, *Jackson v. Mizuho Orthopedic Sys., Inc.*, No. 4:12-CV-01031 (W.D. Mo. Aug. 16, 2013).
Defendant Mizuho Orthopedic Systems, Inc's Brief in Response to Plaintiff's Opening Claim Construction Brief, *Jackson v. Mizuho Orthopedic Sys., Inc.*, No. 4:12-CV-01031 (W.D. Mo. Aug. 16, 2013).
Plaintiff Roger P. Jackson, MD's Suggestions in Support of His Motion to Strike Exhibit a of Mizuho's Opening Claim Construction Brief, *Jackson v. Mizuho Orthopedic Sys., Inc.*, No. 4:12-CV-01031 (W.D. Mo. Aug. 16, 2013).
Defendant Mizuho Orthopedic Systems, Inc.'s Opposition to Plaintiff's Motion to Strike, *Jackson v. Mizuho Orthopedic Sys., Inc.*, No. 4:12-CV-01031 (W.D. Mo. Sep. 3, 2013).
Transcript of Claim Construction Hearing, *Jackson v. Mizuho Orthopedic Sys., Inc.*, No. 4:12-CV-01031 (W.D. Mo. Oct. 11, 2013).
Plaintiff Roger P. Jackson, MD's Claim Construction Presentation for U.S. District Judge Nanette K. Laughrey, *Jackson v. Mizuho Orthopedic Sys., Inc.*, No. 4:12-CV-01031 (W.D. Mo. Oct. 11, 2013).

(56) References Cited

OTHER PUBLICATIONS

Mizuho's Claim Construction Argument, *Jackson* v. *Mizuho Orthopedic Sys., Inc.*, No. 4:12-CV-01031 (W.D. Mo. Oct. 11, 2013).
Order, *Jackson* v. *Mizuho Orthopedic Sys., Inc.*, No. 4:12-CV-01031 (W.D. Mo. Apr. 4, 2014).
European Search Report, EP11798501.0, dated Mar. 30, 2015.
Canadian Office Action, CA2803110, dated Mar. 5, 2015.
Chinese Office Action, CN 201180039162.0, dated Jan. 19, 2015.
Japanese Office Action, JP 2014-142074, dated Jun. 18, 2015.
Japanese Office Action, JP 2014-132463, dated Jun. 18, 2015.
Quayle Action, U.S. Appl. No. 14/792,216, dated Sep. 9, 2015.
Australian Patent Examination Report No. 2, AU2014200274, dated Oct. 9, 2015.
Brochure of OSI on Modular Table System 90D. pp. 1-15, date of first publication: Unknown.
Pages from website http://www.schaerermayfieldusa.com, pp. 1-5, date of first publication: Unknown.
European Examination Report, EP11798501.0, dated Nov. 12, 2015.
Japanese Final Rejection (English version), JP 2014-142074, dated Dec. 6, 2015.
International Search Report and Written Opinion of the International Searching Authority, PCT/US2015/039400, dated Dec. 7, 2015, 13 pages.
Japanese Office Action, JP 2016-041088, dated Apr. 12, 2016.
U.S. Appl. No. 15/189,862, filed Jun. 22, 2016, Jackson et al.
U.S. Appl. No. 15/189,890, filed Jun. 22, 2016, Jackson et al.
U.S. Appl. No. 15/207,599, filed Jul. 12, 2016, Jackson.
U.S. Appl. No. 15/210,339, filed Jul. 14, 2016, Jackson et al.
U.S. Appl. No. 15/234,209, filed Aug. 11, 2016, Jackson et al.
U.S. Appl. No. 15/234,556, filed Aug. 11, 2016, Jackson et al.

\* cited by examiner

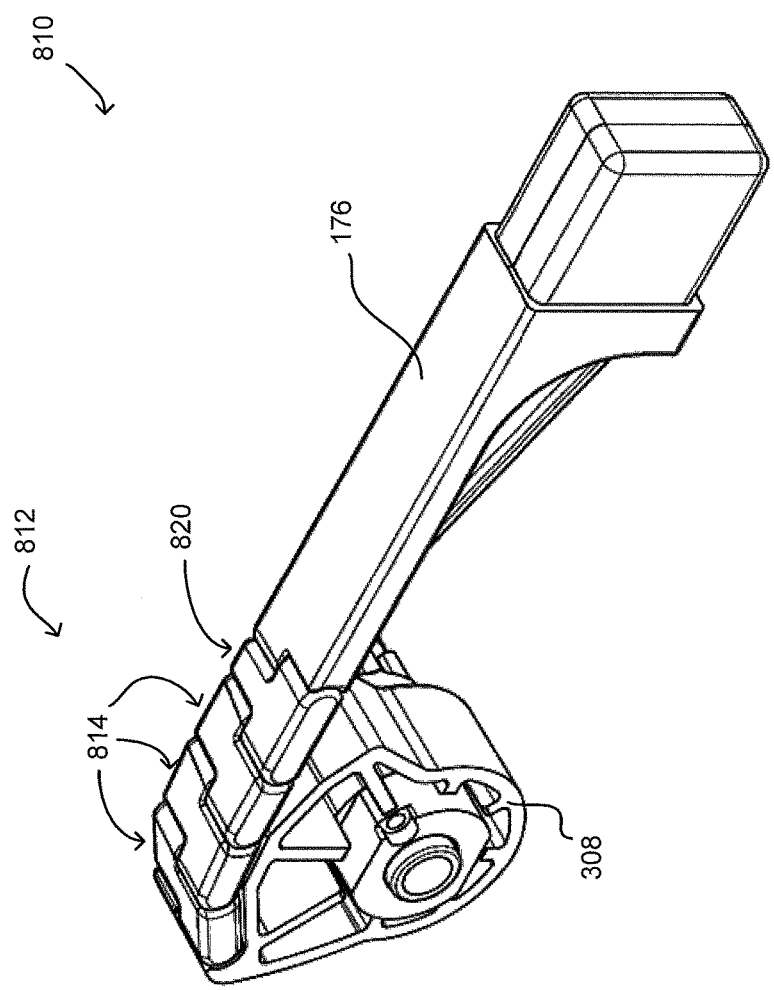

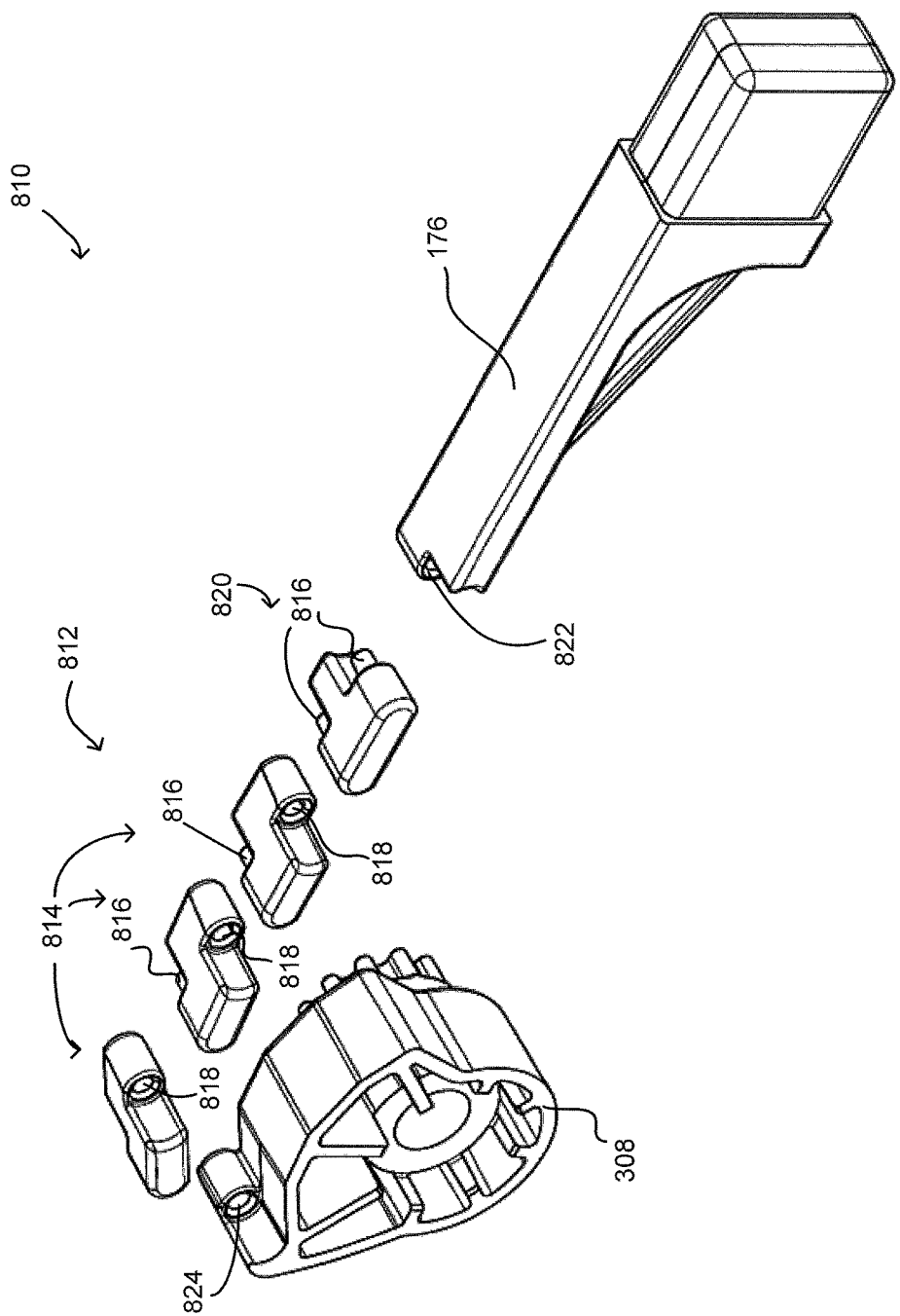

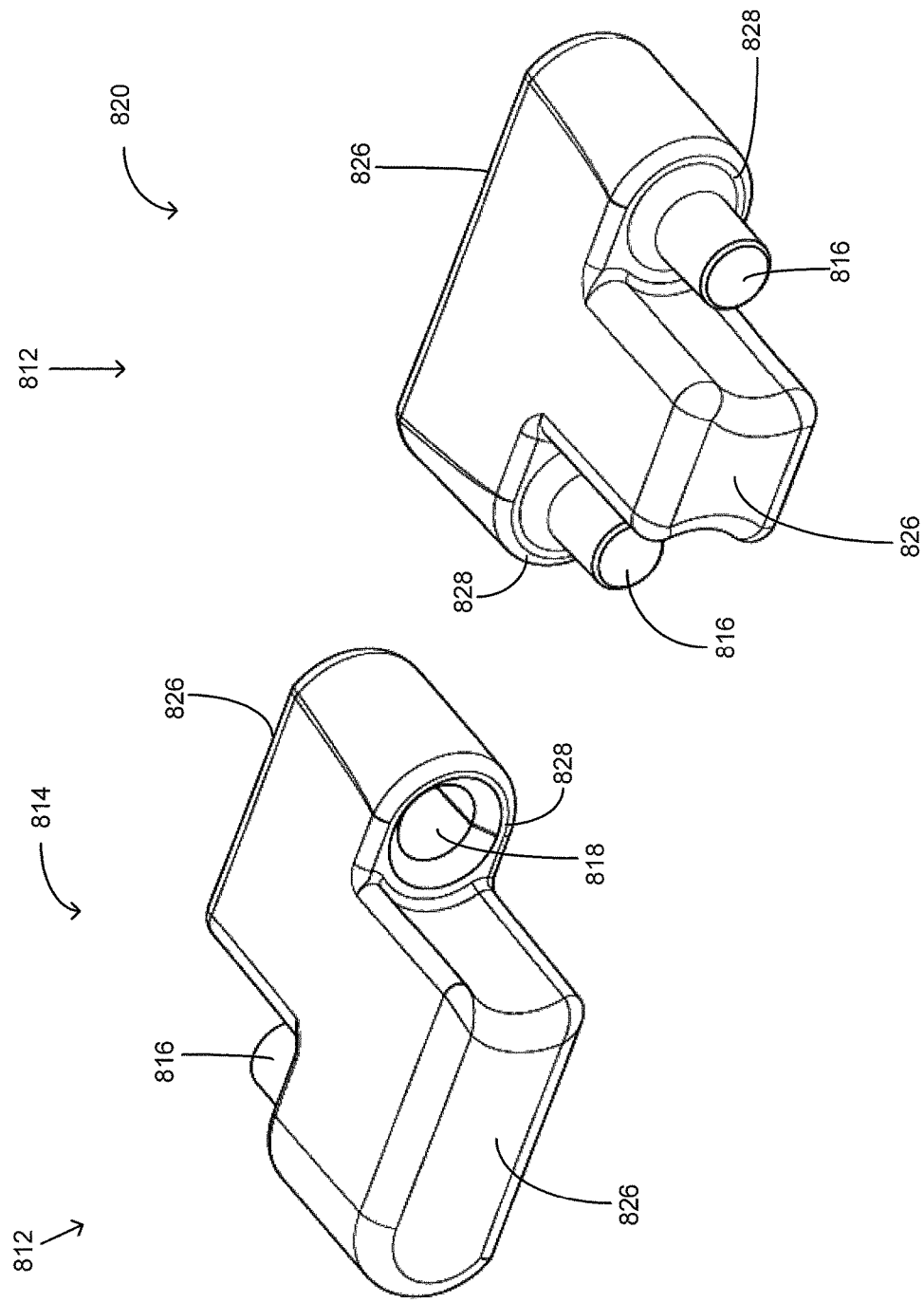

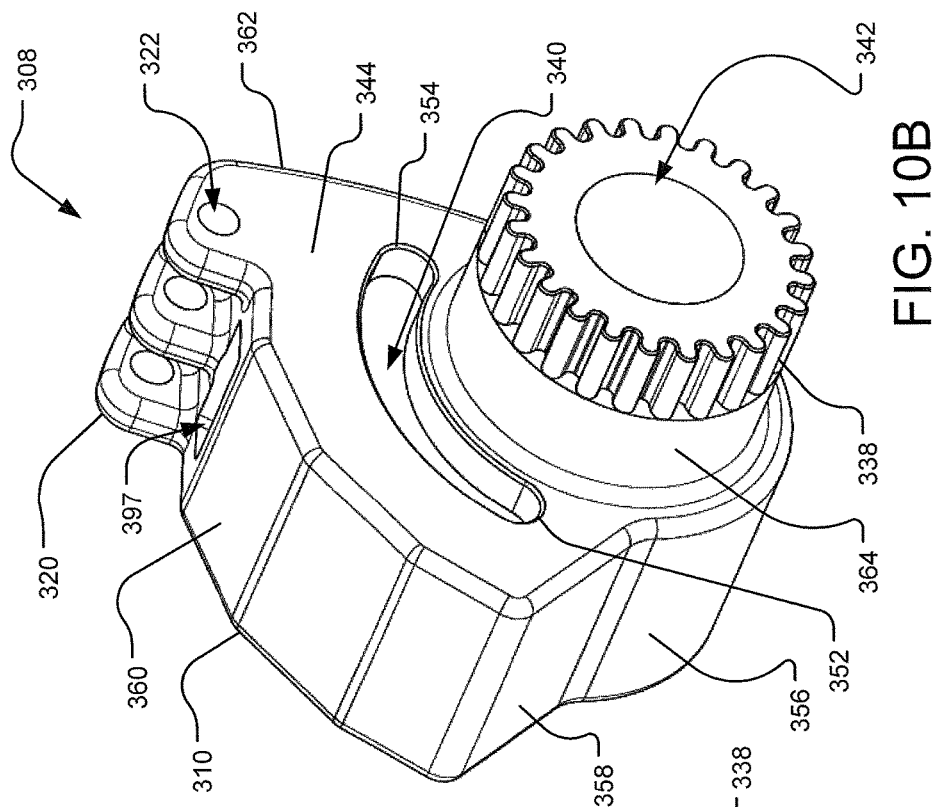
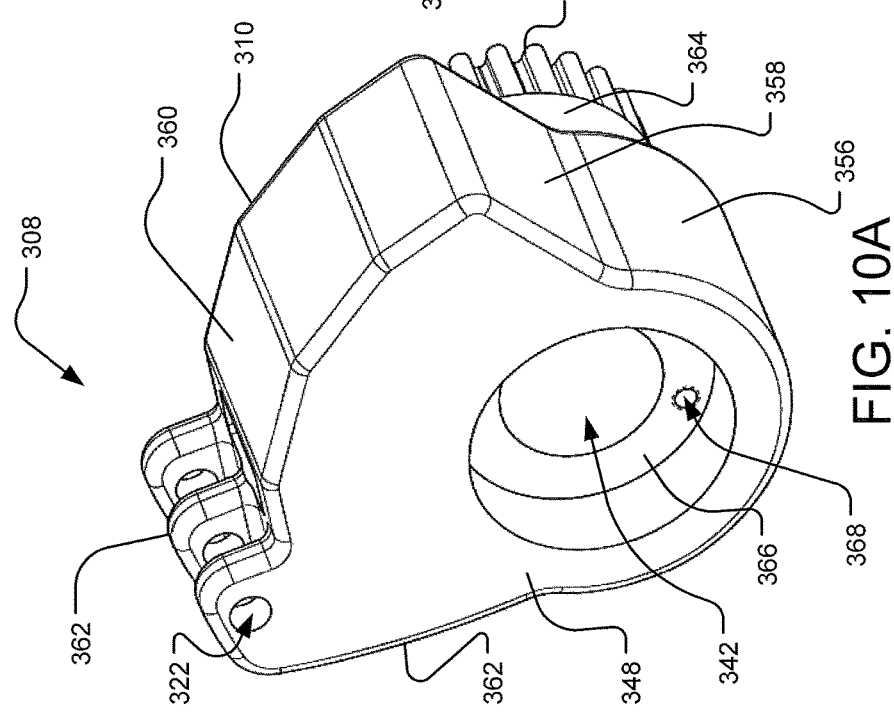
FIG. 10B
FIG. 10A

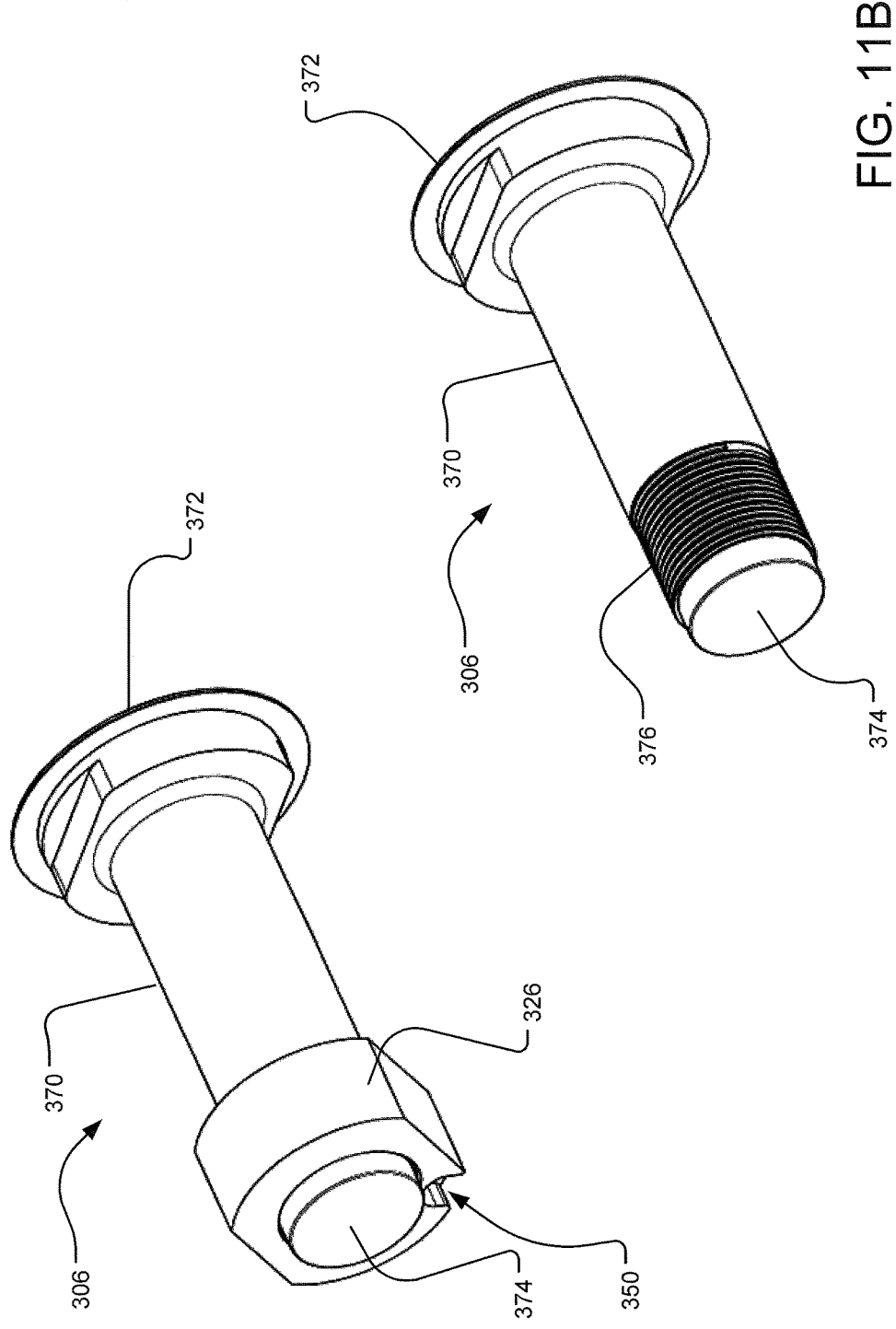

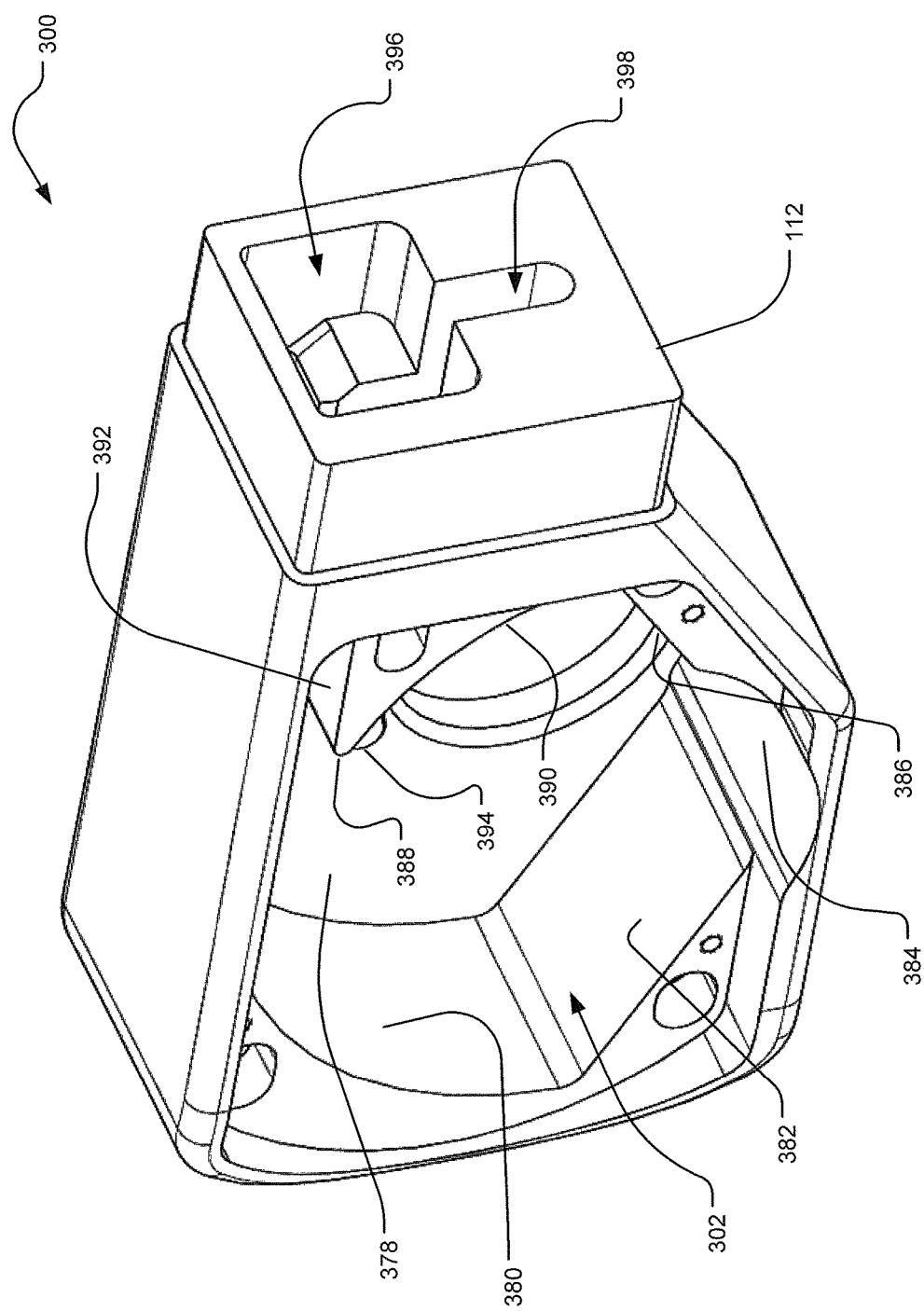

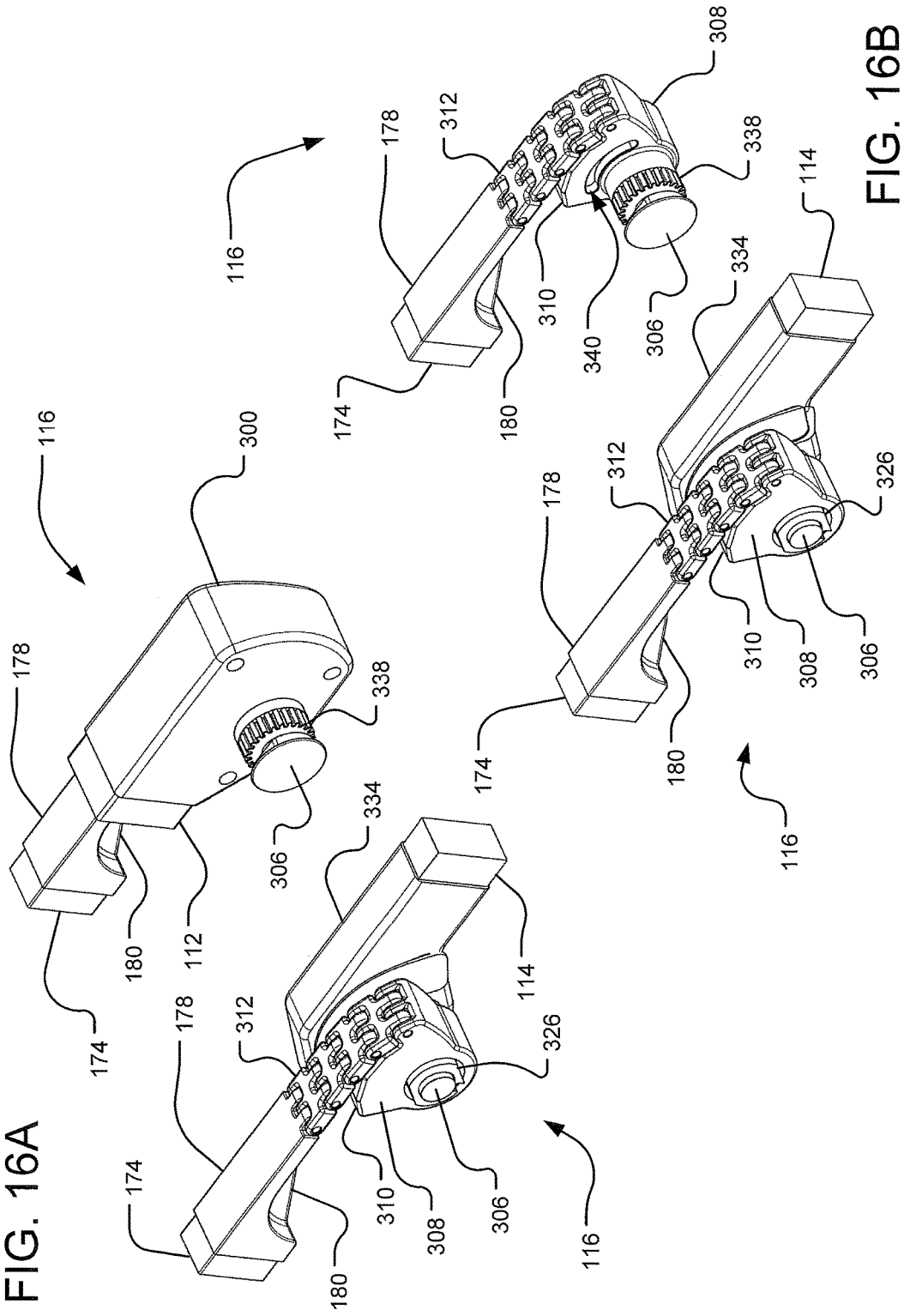

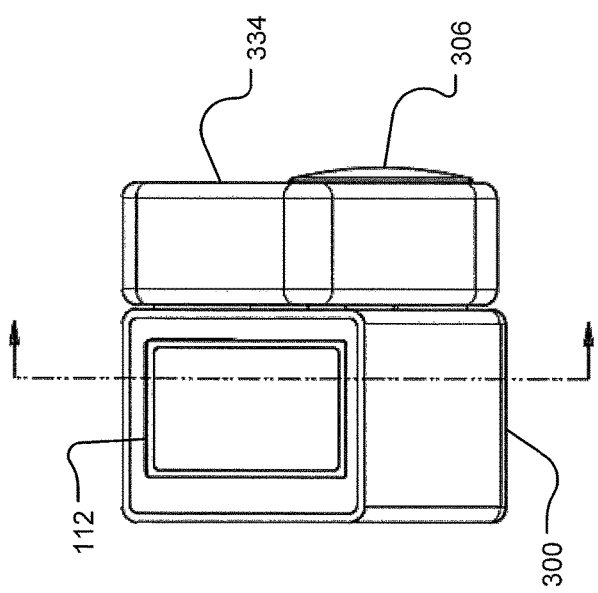
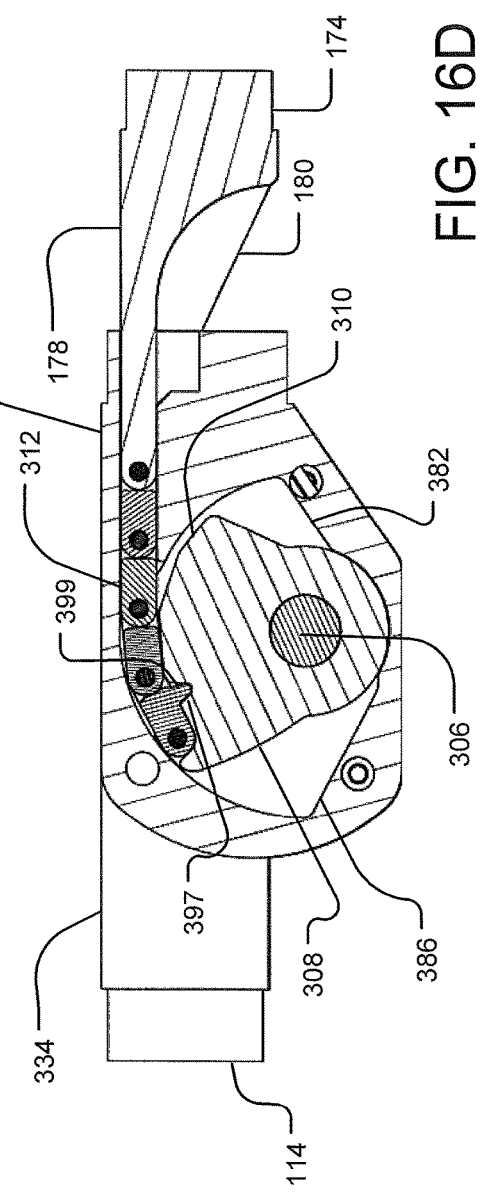

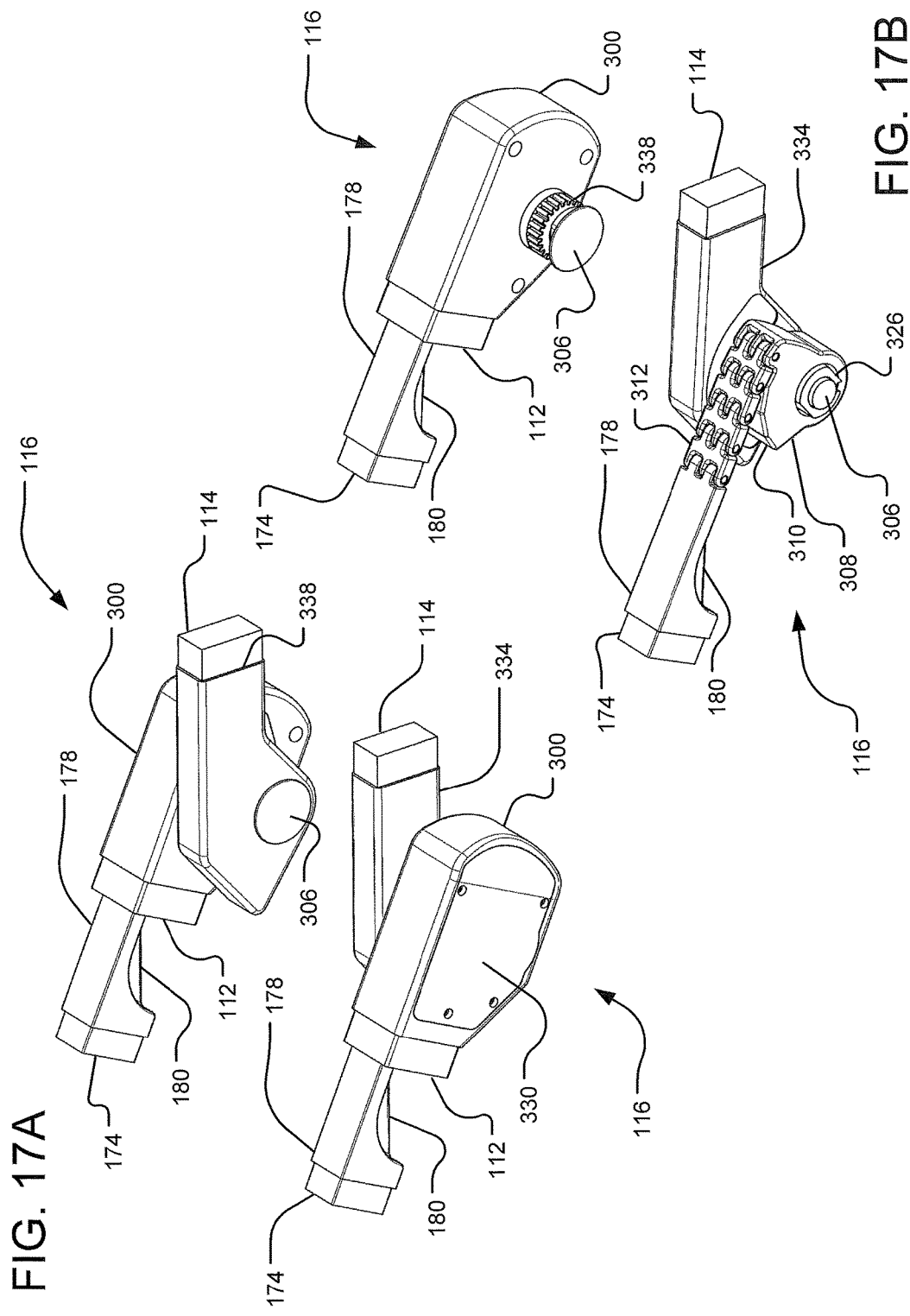

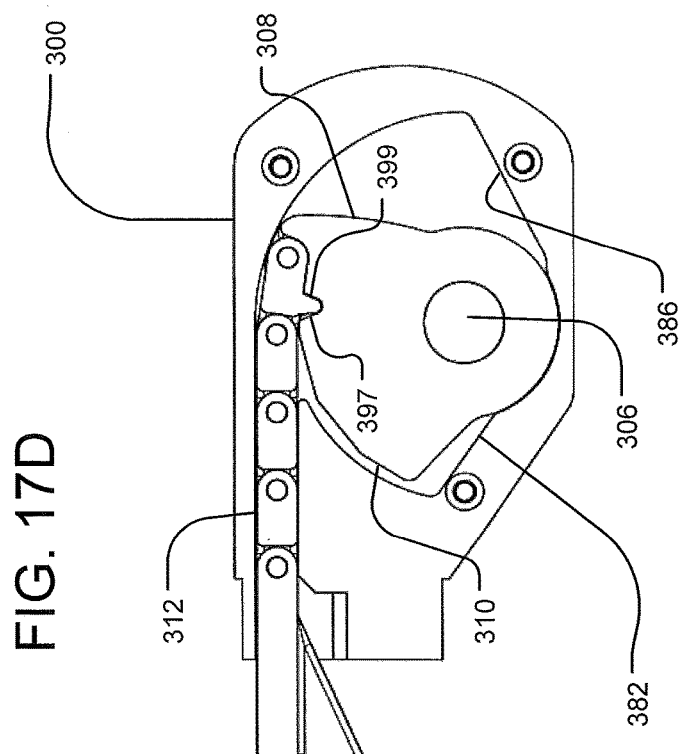
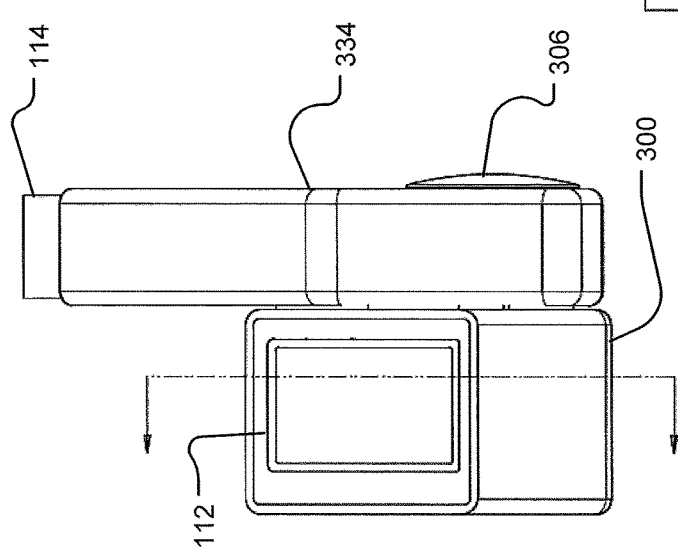
FIG. 17D
FIG. 17C

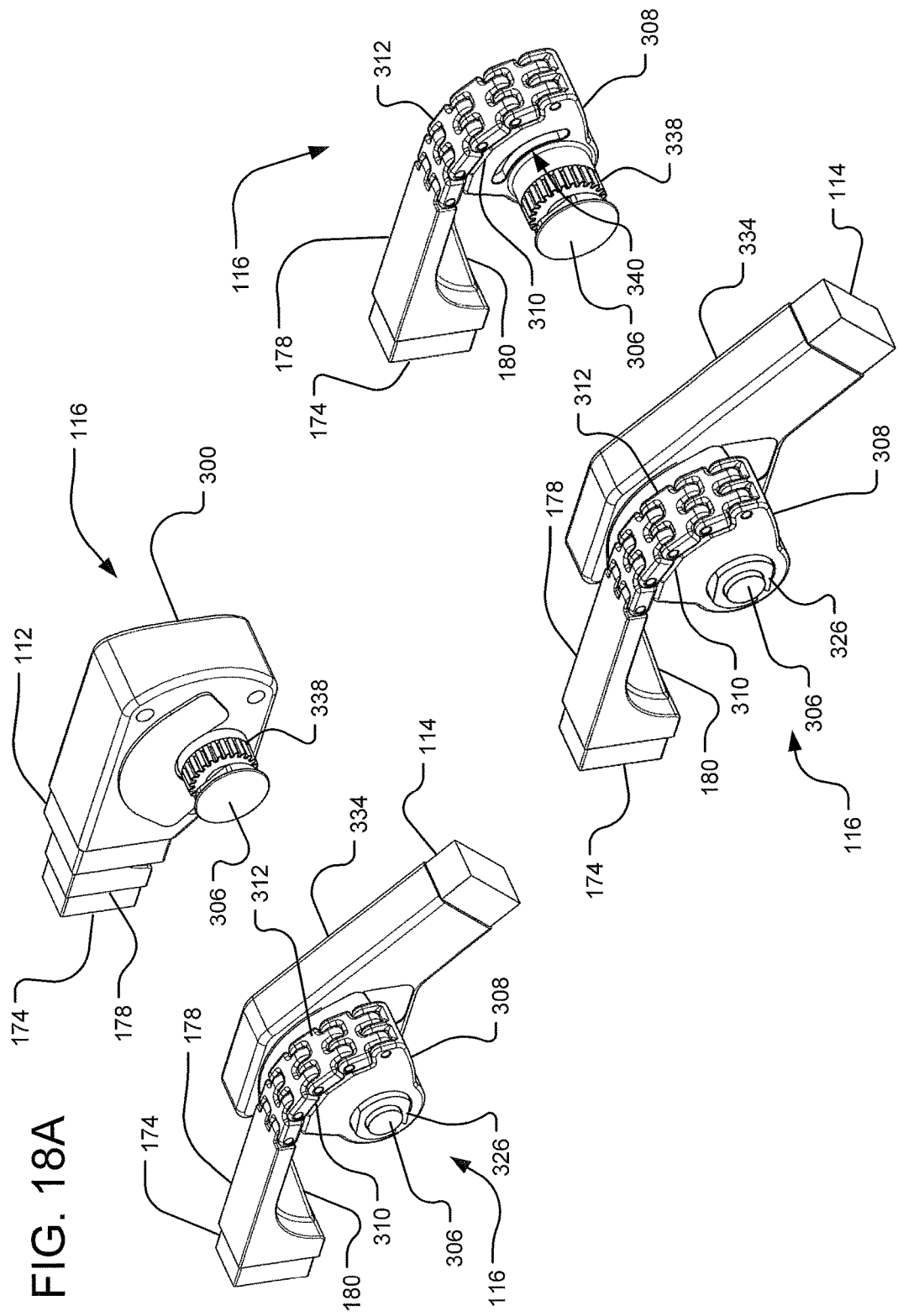

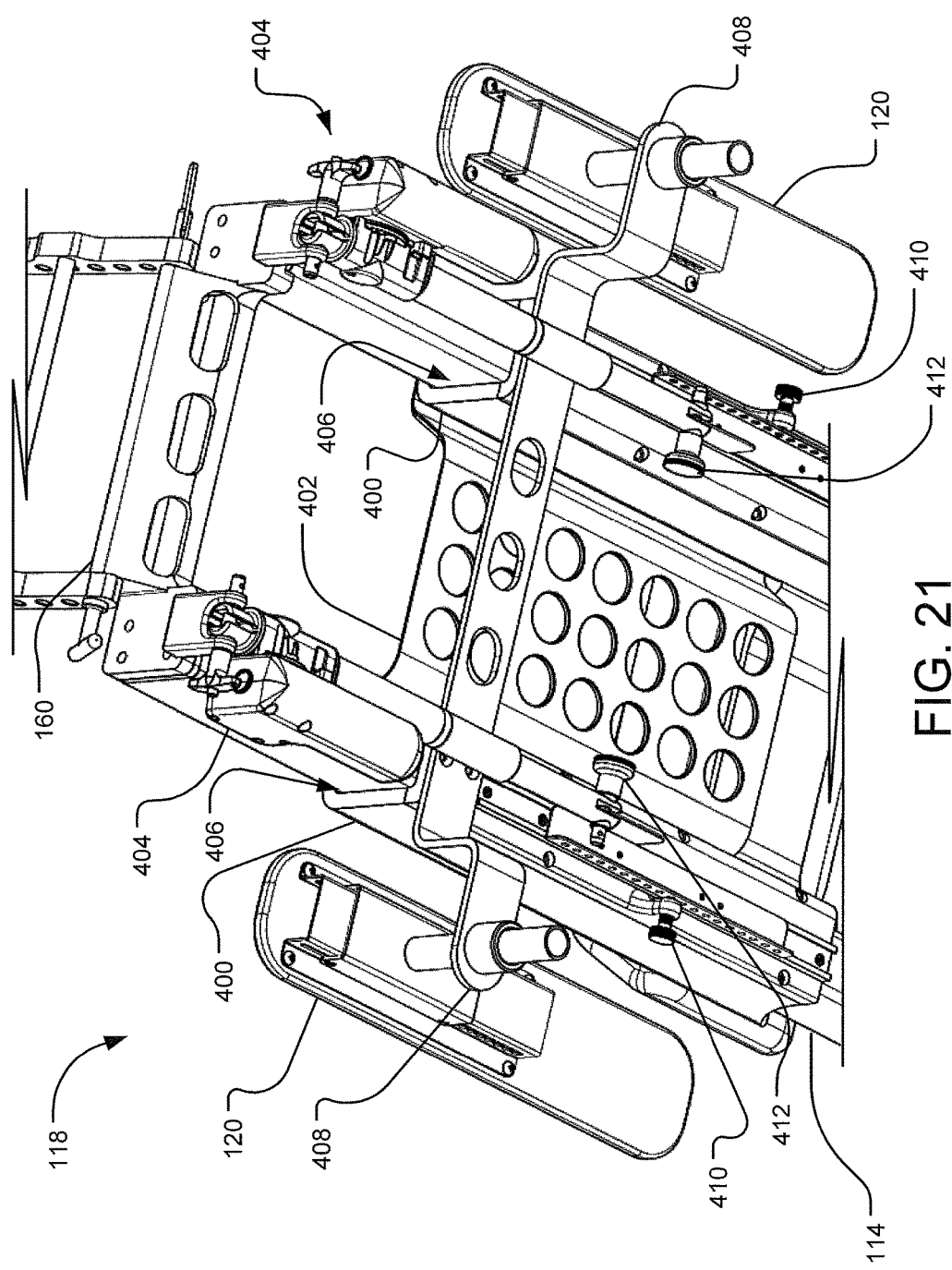

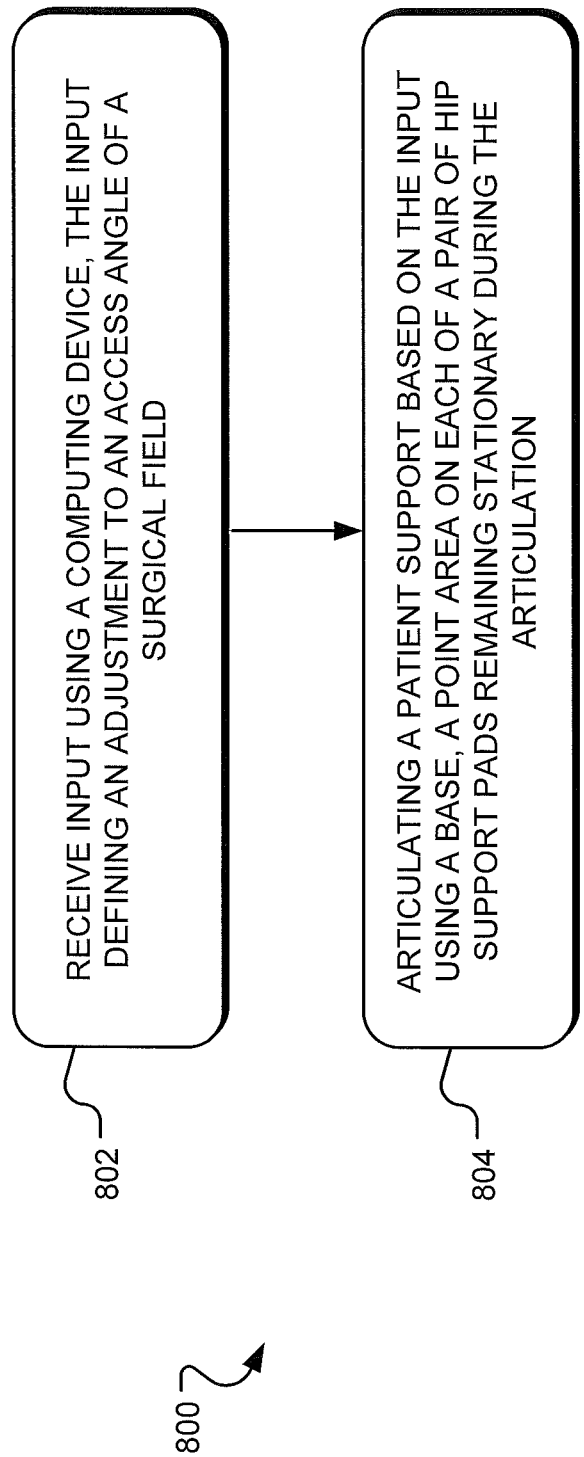

RADIOLUCENT HINGE FOR A SURGICAL TABLE

CROSS-REFERENCE TO RELATED APPLICATIONS

The present application claims priority under 35 U.S.C. §119 to U.S. Provisional Patent Application No. 62/021,481, filed on Jul. 7, 2014, titled "RADIOLUCENT HINGE FOR A SURGICAL TABLE", which is hereby incorporated by reference in its entirety into the present application.

The present application claims priority under 35 U.S.C. §119 to U.S. Provisional Patent Application No. 62/118,282, filed on Feb. 19, 2015, titled "RADIOLUCENT HINGE FOR A SURGICAL TABLE", which is hereby incorporated by reference in its entirety into the present application.

The present application claims priority under 35 U.S.C. §119 to U.S. Provisional Patent Application No. 62/118,305, filed on Feb. 19, 2015, titled "SINGLE COLUMN PATIENT POSITIONING AND SUPPORT STRUCTURE", which is hereby incorporated by reference in its entirety into the present application.

The present application claims priority under 35 U.S.C. §119 to U.S. Provisional Patent Application No. 62/021,630, filed on Jul. 7, 2014, titled "SURGICAL TABLE WITH PATIENT SUPPORT HAVING FLEXIBLE INNER FRAME SUPPORTED ON RIGID OUTER FRAME", which is hereby incorporated by reference in its entirety into the present application.

The present application claims priority under 35 U.S.C. §119 to U.S. Provisional Patent Application No. 62/021,643, filed on Jul. 7, 2014, titled "SINGLE COLUMN PATIENT POSITIONING SUPPORT STRUCTURE", which is hereby incorporated by reference in its entirety into the present application.

The present application claims priority under 35 U.S.C. §119 to U.S. Provisional Patent Application No. 62/021,595, filed on Jul. 7, 2014, titled "PATIENT SUPPORT STRUCTURE WITH PIVOTING AND TRANSLATING HINGE", which is hereby incorporated by reference in its entirety into the present application.

TECHNICAL FIELD

Aspects of the present disclosure relate to systems and methods for supporting a patient during examination and treatment, including medical procedures such as imaging and surgery, and more particularly to a radiolucent hinge that facilitates articulation of a surgical table to various positions while keeping a surgical field stable.

BACKGROUND

Current surgical approaches often utilize medical imaging (e.g., Magnetic Resonance Imaging ("MRI"), fluoroscopy, Computerized Tomography (CT)) of a surgery site in a patient at various times before, during, and/or after surgical procedures for planning, navigation, analysis, and the like. For example, minimally invasive surgical procedures, such as those involving the percutaneous insertion of spinal implants, utilize repeated intra-operative imaging to navigate through small incisions to the implant location and to deploy the spinal implant. However, many surgical tables are not compatible with or otherwise obstruct imaging technologies, resulting in periodic interruptions of a surgery to transfer the patient to and from a separate structure for imaging.

These challenges are further exacerbated with surgical procedures involving multiple access angles to a surgical site. For example, some surgical procedures move the patient to different positions (e.g. Trendelenburg, reverse Trendelenburg, supine, prone, lateral-decibitus, etc.) throughout the procedure to access the surgical site from different angles. Further, some surgical procedures, such as spinal surgery, may involve access through more than one surgical site. Because these sites may not be in the same plane or anatomical location, the patient needs to be moved to and supported in different positions throughout the procedure. However, many conventional tables providing adjustable positions fail to maintain the patient's head in a location conducive to facilitating anesthesia and/or inflict stretching or compression of the patient's spine, skin, and/or other anatomy. Many of these adjustable tables include one or more components, particularly at pivot points, that are susceptible to failure, which risks the patient falling during a procedure should one of the components fail.

It is with these observations in mind, among others, that various aspects of the present disclosure were conceived and developed.

SUMMARY

Implementations described and claimed herein address the foregoing problems, among others, by providing a radiolucent hinge that facilitates articulation of a surgical table to various positions while keeping a surgical field stationary. In one implementation, the radiolucent hinge is driven from a foot end of a base by a motor driving a plurality of pulleys via a drive belt to articulate a patient support of the table to neutral, extension, and flexion positions. To actuate the radiolucent hinge, the pulleys drive a screw-drive within a foot end frame that moves a tube attached to a drive link longitudinally within the frame towards and away from a head end of the base. The drive link is connected to a chain drive with a plurality of links. The chain drive is connected to a faceted sprocket, which has a male spline configured to engage a female spline in a head end spar attachment. To articulate the patient support to the flexion position, the screw-drive moves the tube, actuating the faceted sprocket towards the head end, and to articulate the patient support to the extension position, the screw-drive moves the tube, actuating the faceted sprocket towards the foot end. Under loading, the chain drive is in compression, so if there is a failure of one of the links, the hinge would not fail.

Implementations described and claimed herein address the foregoing problems, among others, by providing a surgical table including a patient support including a first end section including a pair of first end frames joined with a second end section including a pair of second end frames, each of the first end frames is inwardly joined with one of the second end frames at a hinge. Each of the hinges including a drive chain positioned within the foot end frame and including a plurality of drive links coupled together, the drive chain coupled at opposite ends to a sprocket and a drive link, the sprocket being rotatably coupled with the first end section via a hinge pin. The drive link operably coupled with a motor to move the drive link within the second end frame so as to move the drive chain and cause the sprocket to rotate such that the first end section articulates relative to the second end section about the hinge pins. In this implementation, the first end section may be the head end section and the pair of first end frames may be a pair of head end frames. Also in this implementation, the second section may be the foot end section and the pair of second end frames may be a pair of foot end frames. In this or other implementations, the first end section may be the foot end section and the pair of first end frames may be a pair of foot end frames. Also, in this or other implementations, the second end section may be the head end section and the pair of second end frames may be a pair of head end frames.

Implementations described and claimed herein address the foregoing problems, among others, by providing a system for facilitating articulation of a surgical table to various positions while keeping a surgical field stationary. The system includes a motor, a translational driver, and a chain driver. The motor configured to drive a plurality of pulleys connected with a drive belt. The translational driver positioned within a first table frame member and coupled with one of the plurality of pulleys and a drive link, the translational driver configured to translate the drive link within the first table frame member along a longitudinal length of the first table frame member. The chain driver including a plurality of links, the chain driver coupled to the drive link and a faceted sprocket rotatably coupled with a second table frame member, such that when the motor drives the pulleys, the driver moves the driver link and causes the faceted sprocket to rotate while maintaining the chain driver in compression under loading.

Implementations described and claimed herein address the foregoing problems, among others, by providing a surgical table including a patient support that includes a first end section including a pair of first end frames joined with a second end section including a pair of second end frames. Each of the first end frames is inwardly joined with one of the second end frames at a hinge constructed of a radiolucent material. The hinges are actively driven at the hinges to cause the first end section to articulate relative to the second end section.

Implementations described and claimed herein address the foregoing problems, among others, by providing a surgical table having a patient support and a base. The patient support includes a first end section including a pair of first end frames joined with a second end section including a pair of second end frames. Each of the first end frames is inwardly joined with one of the second end frames at a hinge constructed of a radiolucent material. The base includes a pair of opposed end supports operably coupled with outer ends of the patient support, at least one of the end supports comprising a roll assembly configured to rotate the patient support about a roll axis.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

BRIEF DESCRIPTION OF THE DRAWINGS

FIG. 9F is a side perspective view of another example of a radiolucent hinge with the housing among other components hidden from view.

FIG. 9G is an exploded side perspective view of the radiolucent hinge of FIG. 9F.

FIG. 9H is a side perspective view of the links of the radiolucent hinge of FIG. 9F.

FIGS. 10A and 10B illustrate side perspective views of the faceted sprocket of the radiolucent hinge.

FIGS. 11A and 11B show a threaded pin of the radiolucent hinge with and without a nut, respectively.

FIG. 12A shows the housing of the radiolucent hinge with a cover removed.

FIG. 16A is a perspective view of right and left radiolucent hinges in the neutral position, shown with a head end spar attachment of the left radiolucent hinge removed and with a housing of the right radiolucent hinge removed.

FIG. 16B shows the right and left radiolucent hinges of FIG. 16A with the housing of the left radiolucent hinge removed.

FIG. 16C shows a foot end view of the radiolucent hinge in the neutral position.

FIG. 16D illustrates a longitudinal cross-section taken along the section line shown in FIG. 16C.

FIG. 17A is a perspective view of right and left radiolucent hinges in the extension position.

FIG. 17B shows the right and left radiolucent hinges of FIG. 17A shown with a head end spar attachment of the left radiolucent hinge removed and with a housing of the right radiolucent hinge removed.

FIG. 17C shows a foot end view of the radiolucent hinge in the extension position.

FIG. 17D illustrates a longitudinal cross-section taken along the section line shown in FIG. 17C.

FIG. 18A is a perspective view of right and left radiolucent hinges in the flexion position, shown with a head end spar attachment of the left radiolucent hinge removed and with a housing of the right radiolucent hinge removed.

FIG. 18B shows the right and left radiolucent hinges of FIG. 18A with the housing of the left radiolucent hinge removed.

FIG. 21 is a detailed bottom perspective view of the trunk translator of FIGS. 20A.

FIG. 37 illustrates example operations for articulating a patient support in a surgical table.

DETAILED DESCRIPTION

Figure 1A:
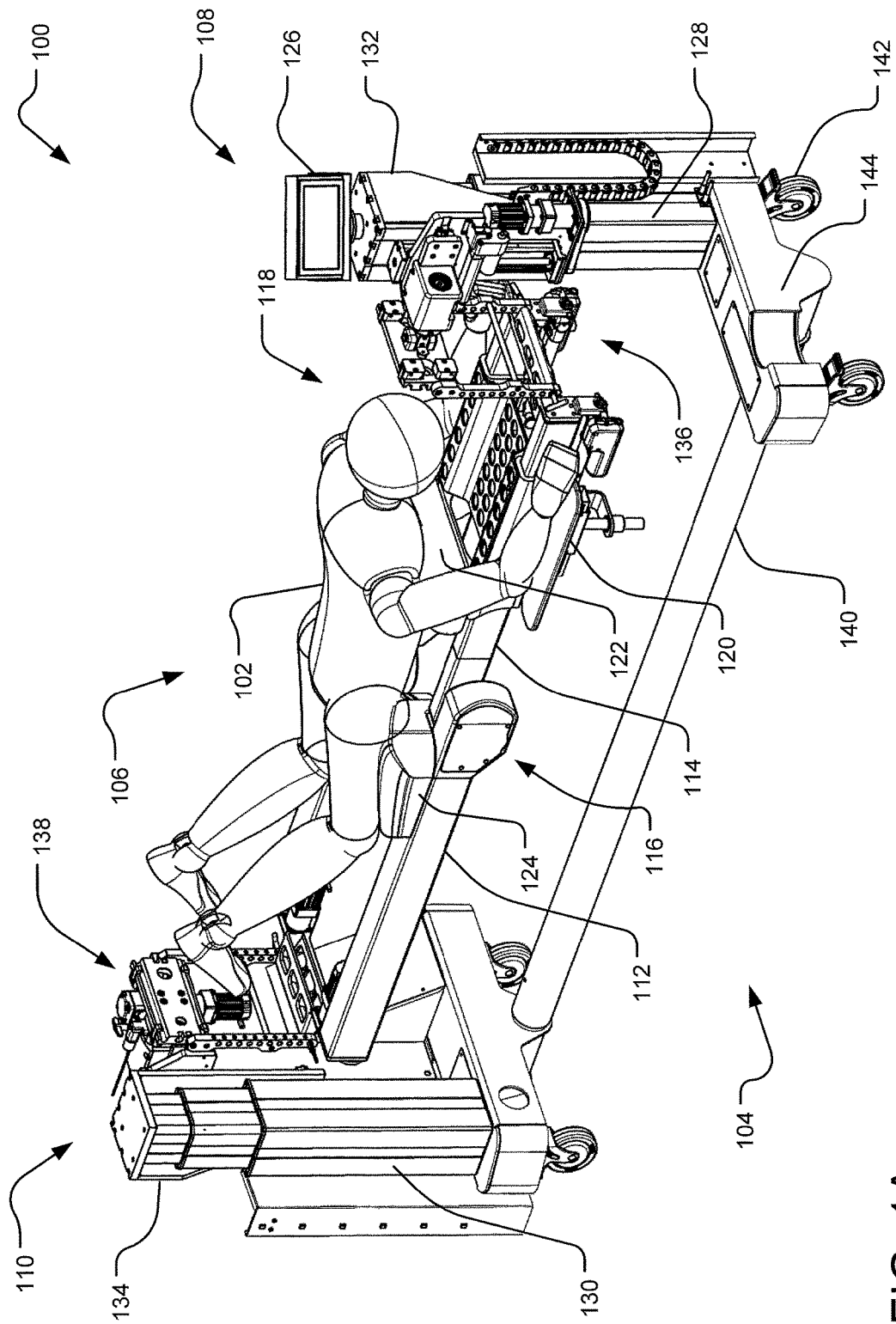
FIG. 1A is an isometric view of a patient in a prone position on an example surgical table with a patient support having a radiolucent hinge, wherein the surgical table is shown in a neutral position.
Figure 1B:
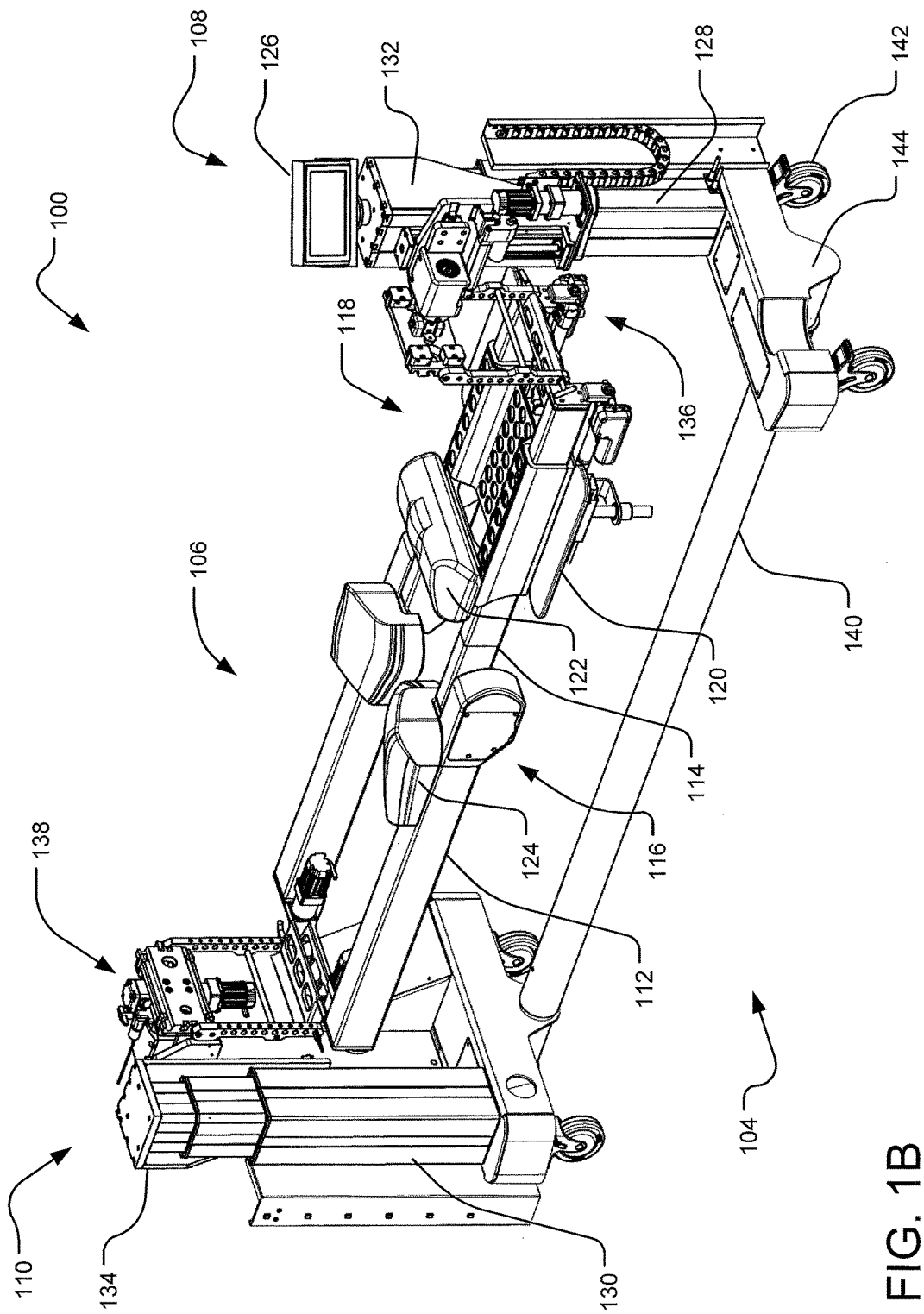
FIG. 1B shows the surgical table of FIG. 1A without the patient.
Figure 1C:
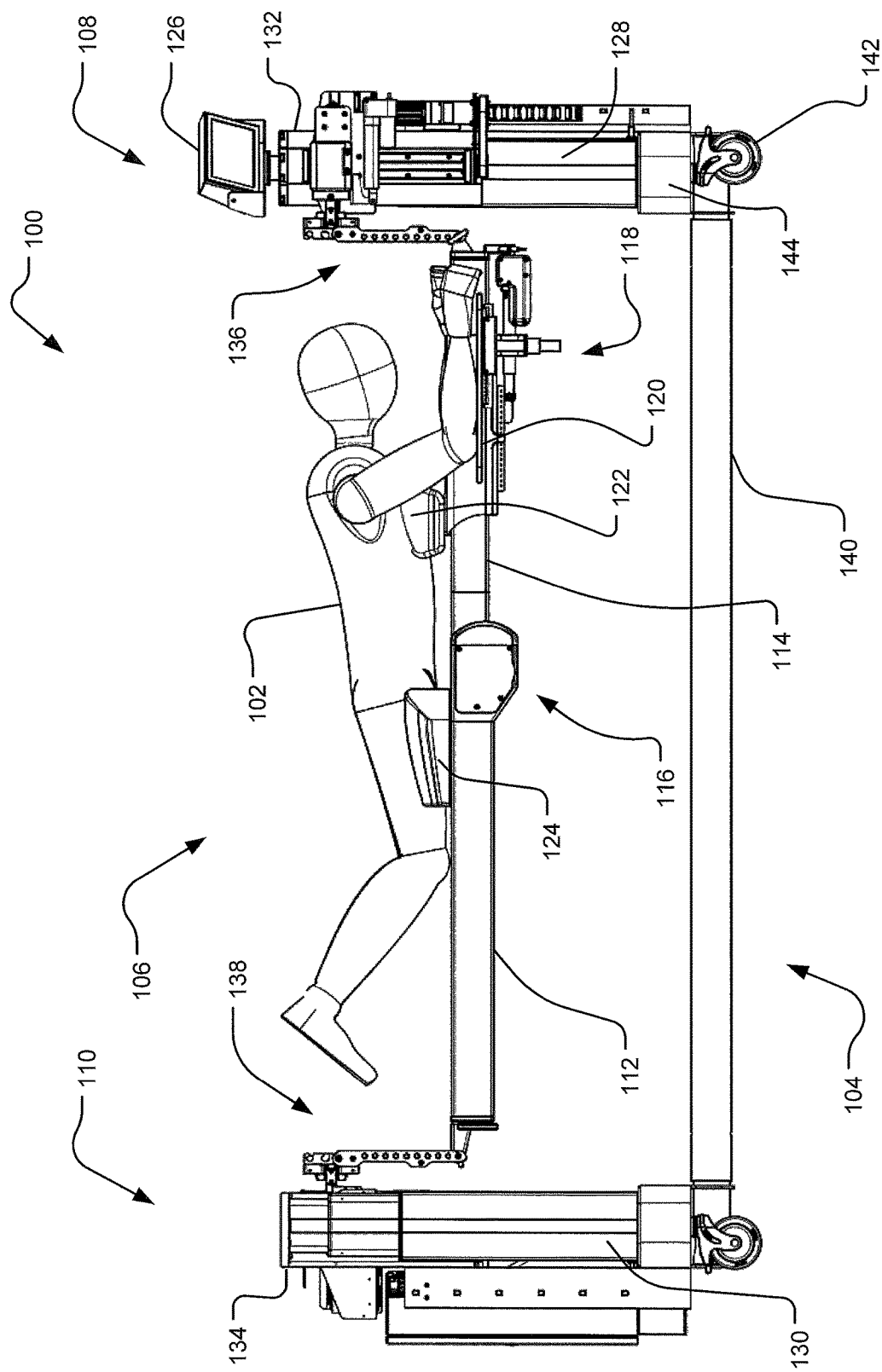
FIG. 1C is a side view of the surgical table of FIG. 1A.
Figure 1D:
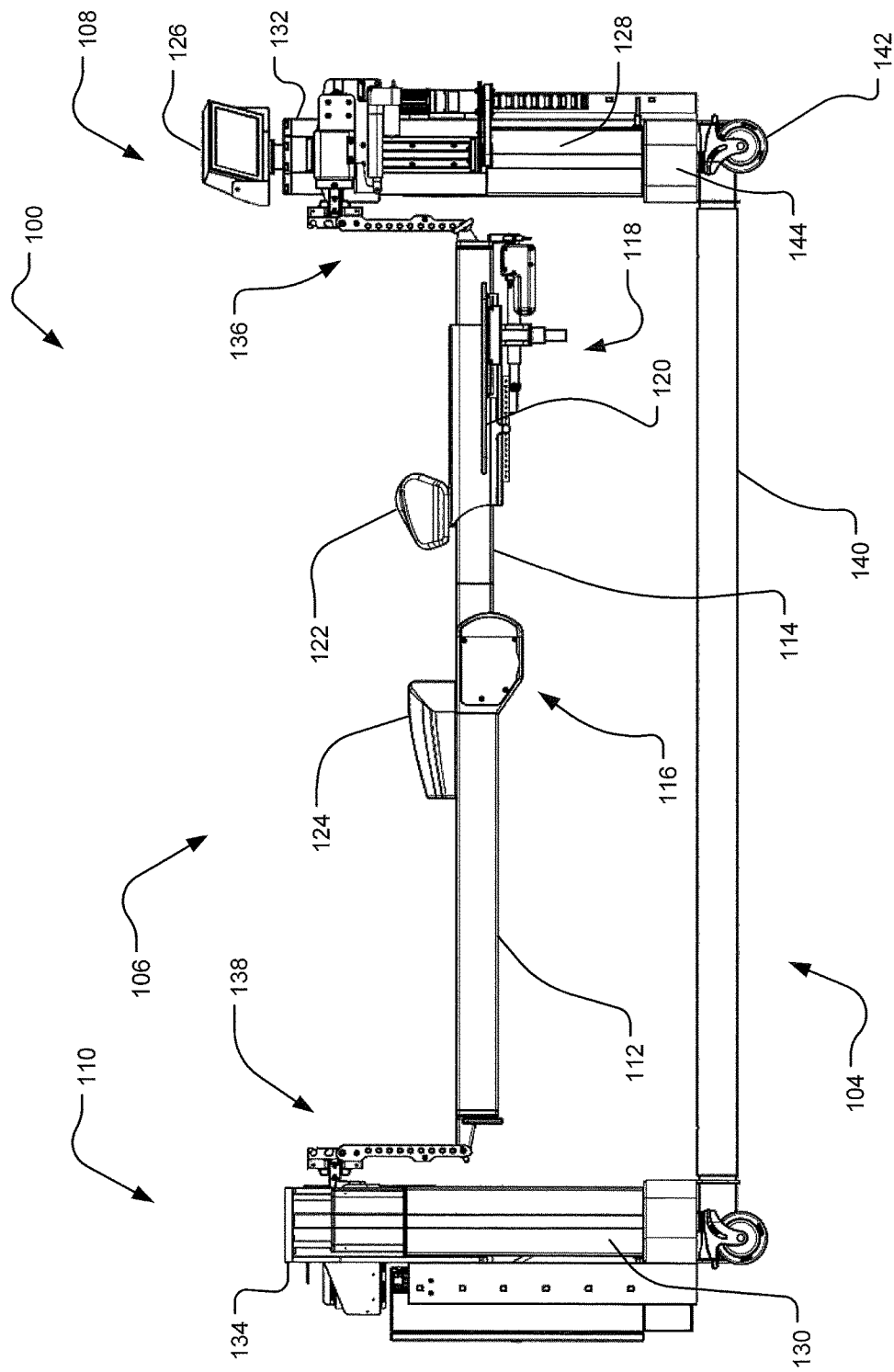
FIG. 1D shows the view of FIG. 1C without the patient.
Figure 2A:
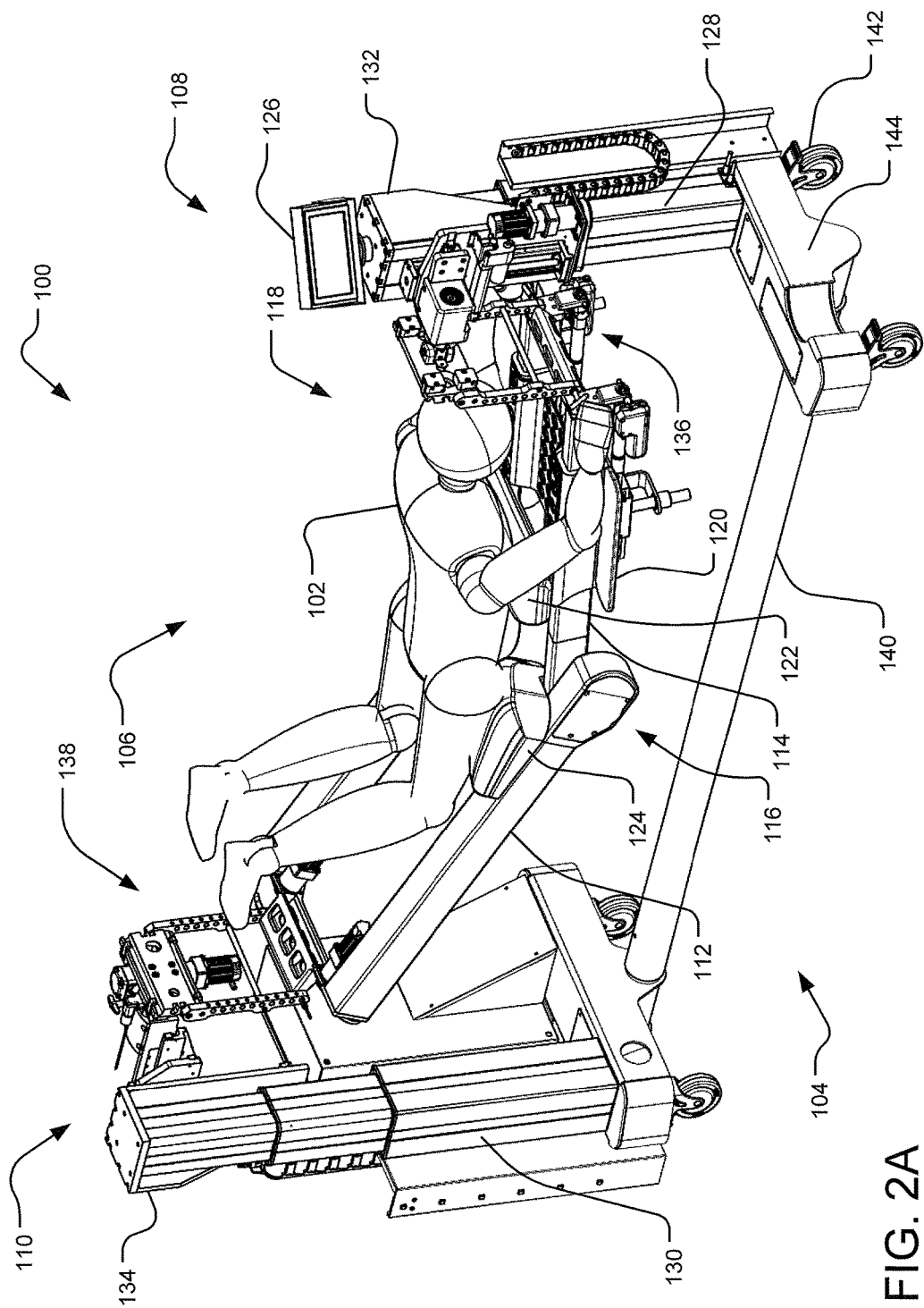
FIG. 2A is an isometric view of the patient in a prone position on the surgical table in an extension position.
Figure 2B:
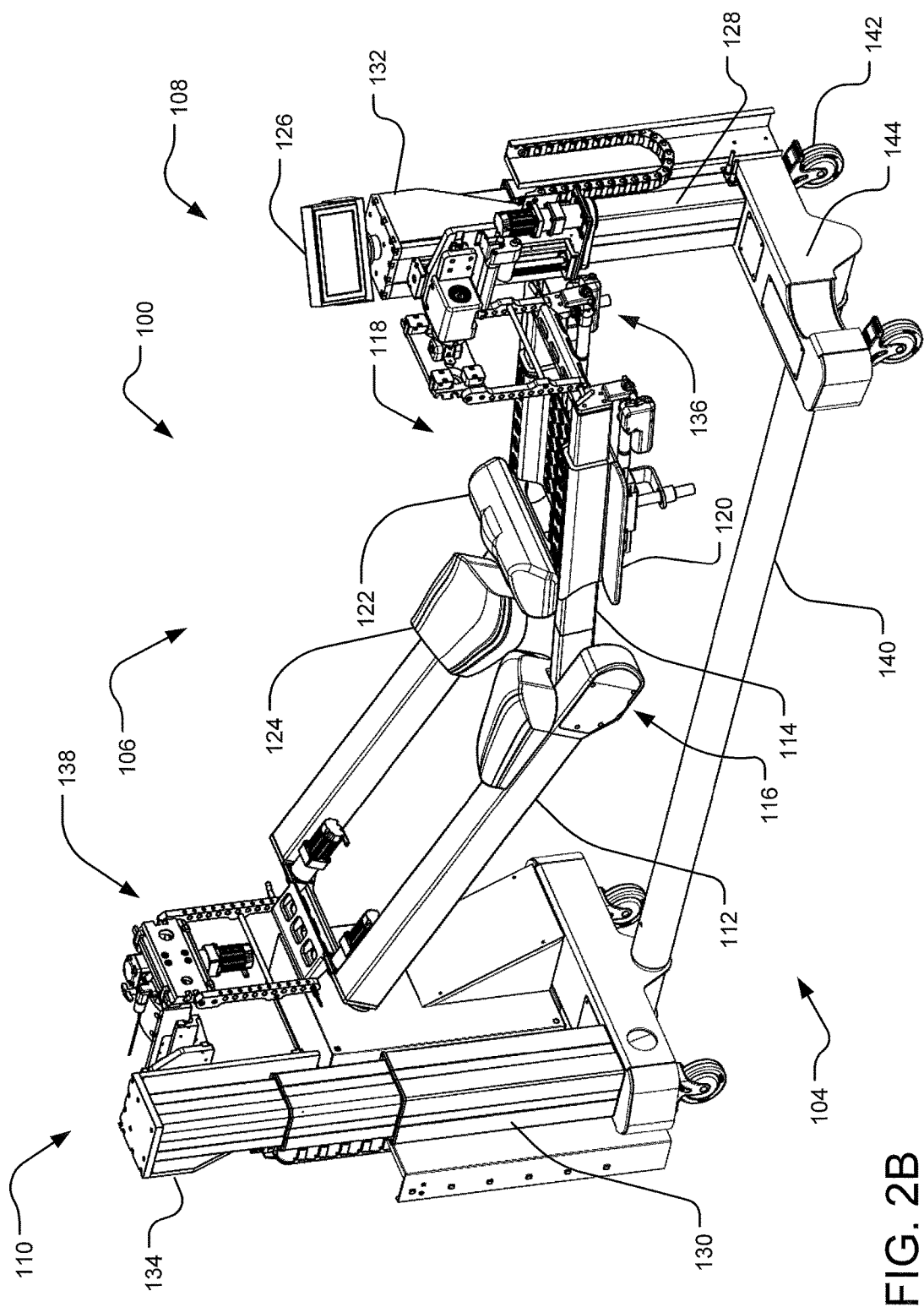
FIG. 2B shows the surgical table of FIG. 2A without the patient.
Figure 2C:
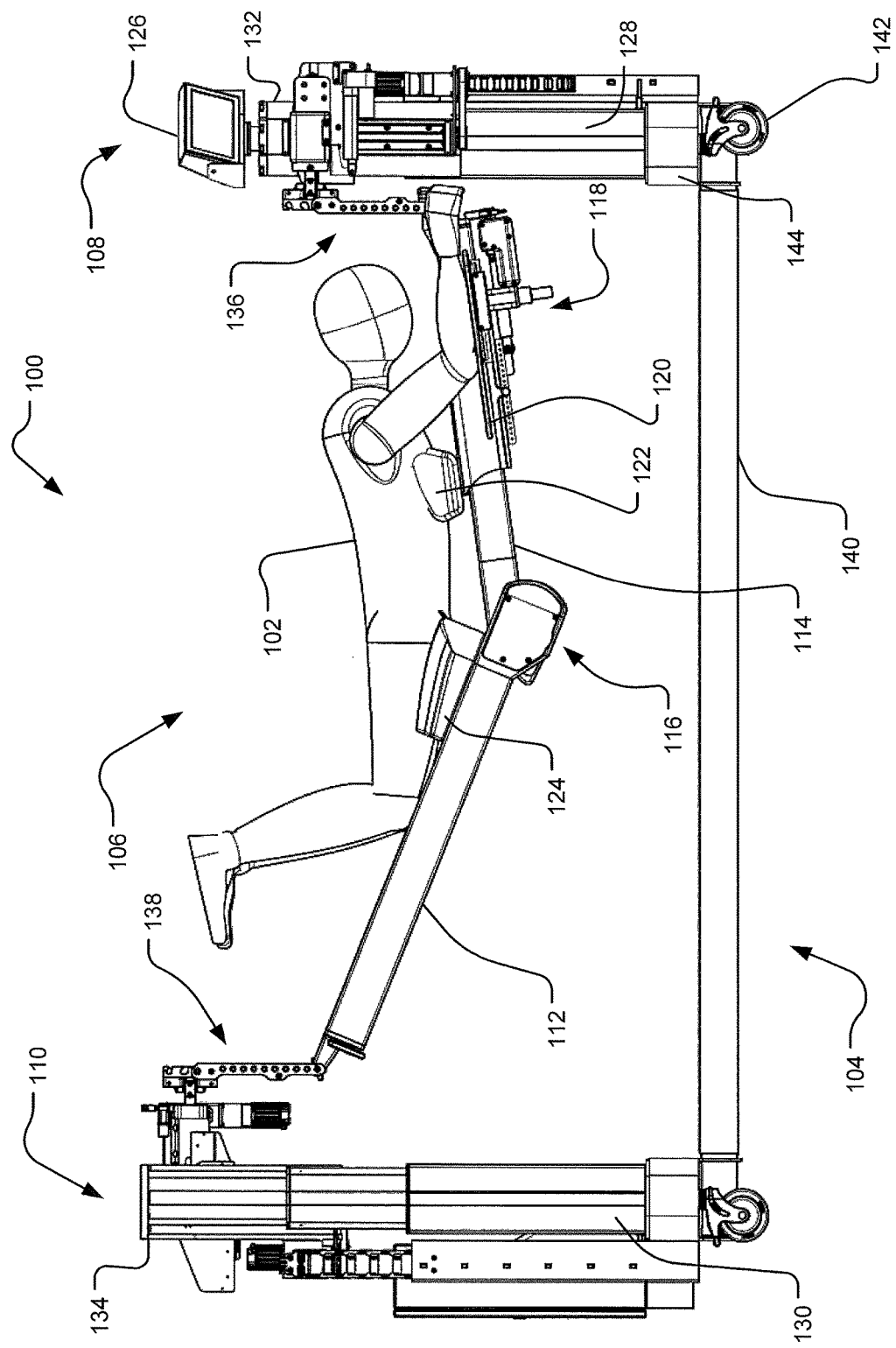
FIG. 2C is a side view of the surgical table of FIG. 2A.
Figure 2D:
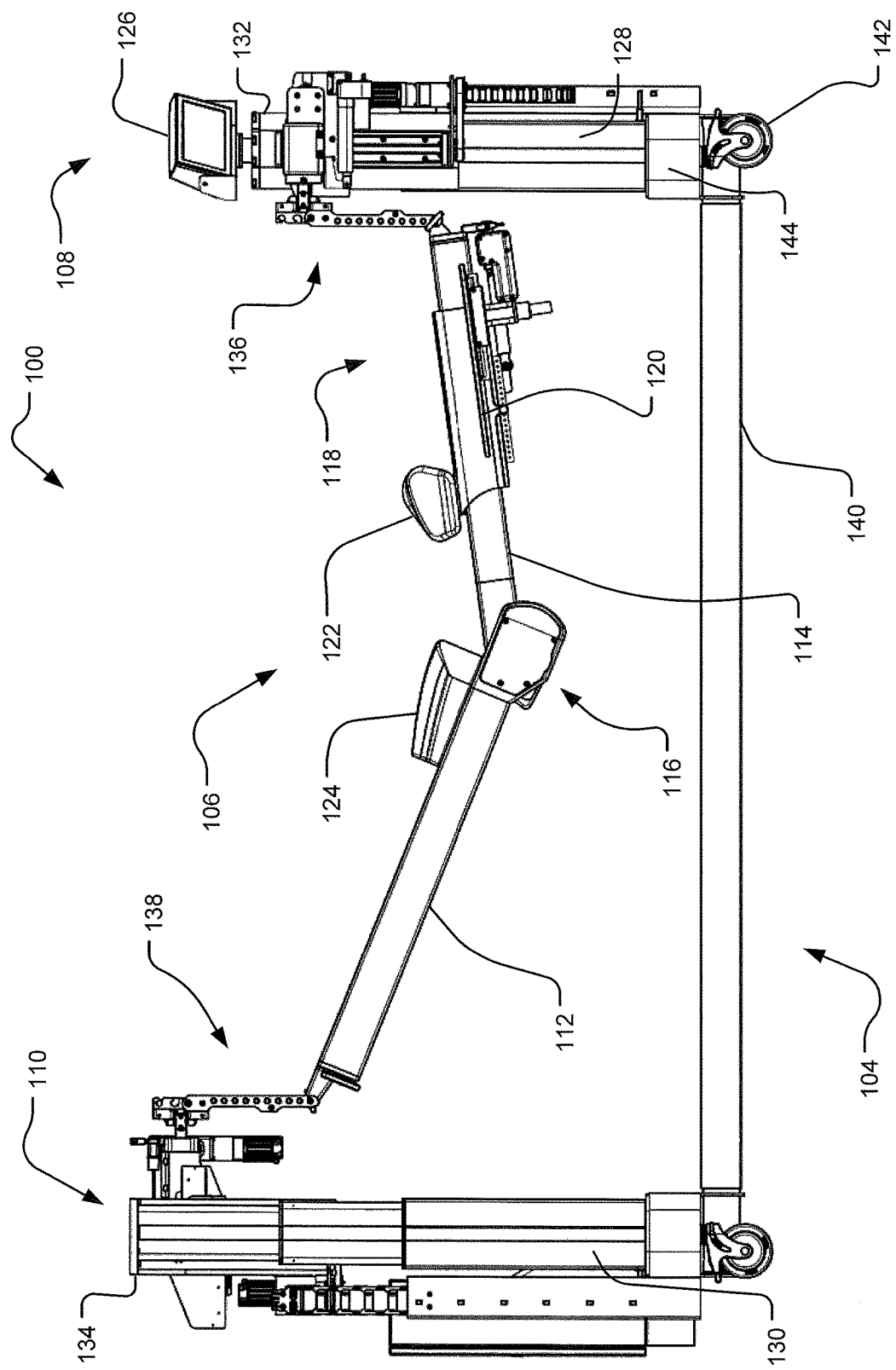
FIG. 2D shows the view of FIG. 2C without the patient.

Aspects of the present disclosure involve a radiolucent hinge that facilitates articulation of a surgical table to various positions while keeping a surgical field stationary. Generally, the surgical table is configured to support the patient in various positions while permitting tilting, swiveling, and/or rolling of the patient with respect to the floor, along a horizontal axis, and while simultaneously maintaining the patient's head in a suitable location for anesthesia, without substantial horizontal translation, and also while preventing undesired spinal distraction or compression. In some aspects, the surgical table includes a base and a patient support.

The base includes dual offset uprights with primary and secondary elevation capabilities at a head end and at a foot end. The base provides dual offset bilateral elevators that are each laterally positioned with respect to each other. The secondary elevator is positioned laterally and medially to the primary elevator to increase space for user-friendly anesthesia administration. Stated differently, the base provides easy access to the patient's head by anesthesia. The head end has a user device configured to control the motion of the surgical table to adjust access to one or more surgical sites or other areas of a patient by medical personnel and equipment. The motion may include, without limitation, vertical movement, rotation, tilting, swiveling, pivoting, angulation, articulation, and the like. The head end and the foot end each provide translation compensation via slides mounted to roll blocks, and the head end further includes an actuator for active translation compensation. As such, the base is sized, shaped, and configured to provide vertical translation or height adjustment of the patient support, as well as provide three degrees of freedom with respect to movement of the patient support relative to a roll axis, a pitch axis, and a yaw axis.

The patient support is connected to the base suspended above the floor and is configured to support the patient in various positions, including, but not limited to, a prone position (i.e., a body position in which the patient lies flat with the chest down and back up), a supine position (i.e., a body position in which the patient lies flat with the chest up and back down), a lateral-decibitus position (i.e., a body position in which the patient lies on his or her side), a Trendelenburg position (i.e., a body position with the feet higher than the head), a reverse Trendelenburg position (i.e., a body position with the head higher than the feet), and the like. In addition to supporting a flex frame patient support, the base supports the use of fixed frames and fixed imaging tops, which are generally used for sandwich-and-roll movement. However, the surgical table facilitates continued sandwich- and roll patient positioning with an actively driven hinge, thereby providing a flex frame with sandwich-and-roll capabilities, wherein the patient is rolled over 180-degrees between supine and prone positions. The patient support structure may also provide for a length adjustment with respect to the base when the structure is angulated (e.g., extended or flexed) or the ends are pivoted so as to put the structure into a Trendelenburg or reverse Trendelenburg position.

In one particular aspect, the patient support includes at least one hinge that is driven from the foot end of the base by a motor driving a plurality of pulleys via a drive belt to articulate the patient support to neutral, extension, and flexion positions. The hinge and some or all regions of the patient support are made from a radiolucent material (e.g., carbon fiber, polyether ether ketone, etc.) to prevent interference with imaging while the patient is positioned on the patient support. To actuate the hinge, the pulleys drive a driver within a foot end frame that moves a tube attached to a drive link longitudinally within the frame towards and away from the head end of the base. The drive link is connected to a chain drive having a plurality of links. The chain drive is connected to a faceted sprocket, which has a male spline configured to engage a female spline in a head end spar attachment of a head end frame. To articulate the patient support to the flexion position, the driver moves the tube, actuating the faceted sprocket towards the head end, and to articulate the patient support to the extension position, the driver moves the tube, actuating the faceted sprocket towards the foot end. When articulating to the extension position, primary and secondary elevators of the foot end and the head end of the base move vertically up away from the floor while the actuator in the head end extends. When articulating to the flexion position, the primary and secondary elevators of the foot end and the head end of the base move vertically down towards the floor while the actuator in the head end moves for active linear translation compensation. In other words, the head end and the foot end are fixed relative to each other, so as the patient support articulates between extension, flexion, and neutral, the overall length of the frame changes. The surgical table is configured to articulate to various positions while keeping the surgical field stationary. Stated differently, a point area on each of a pair of hip support pads remains stationary while the surgical table moves around the point area.

Under loading, the hinge is in compression, as opposed to tension, so if there is a failure of one of the links, the hinge would not fail. In addition to the compression of the hinge, the surgical table may also include a fail-safe connection mechanism for connecting the patient support to the base while simultaneously preventing incorrect disconnection of the patient support from the base, which could cause the patient support to collapse, potentially resulting in patient injury. In one implementation, the table is rated for 600 pounds of weight. Accordingly, the table simultaneously incorporates radiolucent materials and is configured to support and position a heavy load capacity.

For a detailed description of an example table 100 for positioning and supporting a patient 102 during medical procedures, such as surgery and imaging, reference is made to FIGS. 1A to 5C. In one implementation, the table 100 includes a base 104 suspending a patient support 106 above a floor surface on which the base 104 rests. The patient support 106 extends longitudinally between a head end 108 and a foot end 110 of the base 104. It will be appreciated, however, that the patient support 106 may be suspended above the floor using other bases, mobile structures, permanent structures (e.g., ceiling, walls, or other building structures), and/or the like. Furthermore, the patient support 106 may include one or more additional patient support structures adapted to hold patients of various sizes and shapes (e.g., pediatric patients, tall patients, obese patients, etc.), to provide support for a particular medical procedure, or the like. The patient support 106 may additionally include more or more removable, replaceable, and/or interchangeable portions. The table 100 may include systems and methods similar to those described in U.S. patent application Ser. No. 14/012,434, filed on Aug. 28, 2013 and entitled "Patient Positioning Support Apparatus with Virtual Pivot-Shift Pelvic Pads, Upper Body Stabilization and Fail-Safe Attachment Mechanism" and/or U.S. patent application Ser. No. 11/788,513, filed on Apr. 20, 2007 and entitled "Patient Positioning Support Structure," both of which is specifically incorporated by reference in its entirety herein.

It will be appreciated that throughout this Detailed Description, designations, such as right, left, top, bottom, front, back, and the like have no meaning other than for purposes of facilitating the discussion herein. For example, reference may be made herein to right and left sides of the table 100 corresponding to a respective adjacent side of the patient 102 when the patient 102 is lying in the prone position on the patient support 106, as shown in FIG. 1A.

In one implementation, the patient support 106 includes a frame having a foot end section 112 and a head end section 114 connected or joined inwardly at a pair of hinges 116. The frame of the patient support 106 includes right and left sides spaced relative and opposed to one another and extending longitudinally between the head end 108 and the foot end 110. As such, the head end frames or frame members 114 are mounted to the head end 108 of the base 104, and the foot end frames or frame members 112 are mounted to the foot end 110 of the base 104. Accordingly, the head end section 114 may include a pair of head end frames 114 and the foot end section 112 may include a pair of foot end frames 112, wherein inward ends of the frames 112, 114 are joined at the hinges 116.

The foot end frames 112, the head end frames 114, and the hinges 116 are substantially strong to withstand forces applied to the patient support 106 during movement and while supporting the patient 102. Furthermore, the hinges 116 and at least a portion of the head end frames 114, the foot end frames 112, and/or other components of the patient support 106 are made from radiolucent materials to prevent or otherwise reduce interference with imaging.

The patient support 106 includes one or more pads or supports for positioning the patient 102. For example, when the patient 102 is lying on the patient support 106 in the prone position, as shown in FIG. 1A, the patient support 106 includes arm supports 120 and a chest pad 122 disposed on a trunk translator 118 and hip pads 124 disposed on the foot end frames 112. In one implementation, the foot end frame 112 includes a sling or other support for the lower limbs of the patient 102 and a pillow or similar support under the shins.

The base 104 includes a user device 126, which may be generally any form of computing device capable of interacting with the table 100 and controlling the various operations of the table 100, such as a personal computer, workstation, terminal, portable computer, mobile device, mobile phone, tablet, multimedia console, and the like. The base 104 includes a control box housing one or more electrical components, such as electrical wiring, junctions, circuitry, and the like, associated with the operation and control of the table 100 as directed by the user device 126 based on input from a user, such as a surgeon, technician, nurse, or other medical personnel. The user device 126 may receive the input from the user, for example, via a graphical user interface (GUI) using an input device, such as a mouse, keyboard, touch screen, or the like. In one implementation, the user device 126 is mounted to an upright in the head end 108, and the foot end 110 includes the control box housing the one or more electrical components for controlling the operations of the table 100, including the articulation of the patient support 106 to various positions. The user device 126 may further receive input from and communicates with one or more sensors (e.g., motion sensors) to facilitate control of the operations of the table 100. In one implementation, the roll assemblies 136 and 138 include "hot plates" that are wired with plugs to provide power to the trunk translator 11 and the various patient support 106 motors and components at the head end 108 and/or the foot end 110.

In one implementation, the base 102 includes: moveable base ends 144 with castors 142; offset uprights including secondary elevator mount assemblies 132 and 134 and linear actuators 128 and 130 configured to provide vertical translation or height adjustment of the patient support 106; and roll assemblies 136 and 138 configured to provide three degrees of freedom with respect to movement of the patient support 106 relative to a roll axis, a pitch axis, and a yaw axis. Further, in one implementation, both the head end 108 and the foot end 110 provide translation compensation via slides mounted to the roll assemblies 136, 138, and the head end 108 includes an actuator providing active translation compensation.

In one implementation, the head end 108 and the foot end 110 of the base 102 are opposed to and fixed relative to each other. Stated differently, the moveable base ends 144 are coupled together with a base frame member 140 extending longitudinally between the moveable base end 144 of the head end 108 and the moveable base end 144 of the foot end 110. The base frame member 140 may be tubular, rectangular, or any other structural shape. The moveable base ends 144 are supported above the floor surface by respective castors 142, which facilitate moving the base 104 by rolling along the floor surface. The castors 142 may including one or more locking mechanisms for fixing a location of the base 104 on the floor surface. In one implementation, the base frame member 140 is permanently fixed with respect to the overall length. In another implementation, the base frame member 140 is adjustable relative to the overall length allowing the moveable base ends 144 to be moved closer together, thereby facilitating the storage of the base 104. Further, the base frame member 140 may be telescopically configured to adjust the length of the base 104. The length of the base frame member 140 may be manually adjusted and/or adjusted using a powered drive mechanism controlled by the user device 126. In one implementation, the base 104 and the patient support 106 are configured to move the patient 102 to various positions without the opposed moveable base ends 144 and their associated uprights displacing relative to each other. In other words, as the patient 102 is moved through a range of positions on the surgical table 100, the uprights, including the secondary elevator mount assemblies 132, 134 and the linear actuators 128, 130, will remain fixed relative to each other.

Figure 3A:
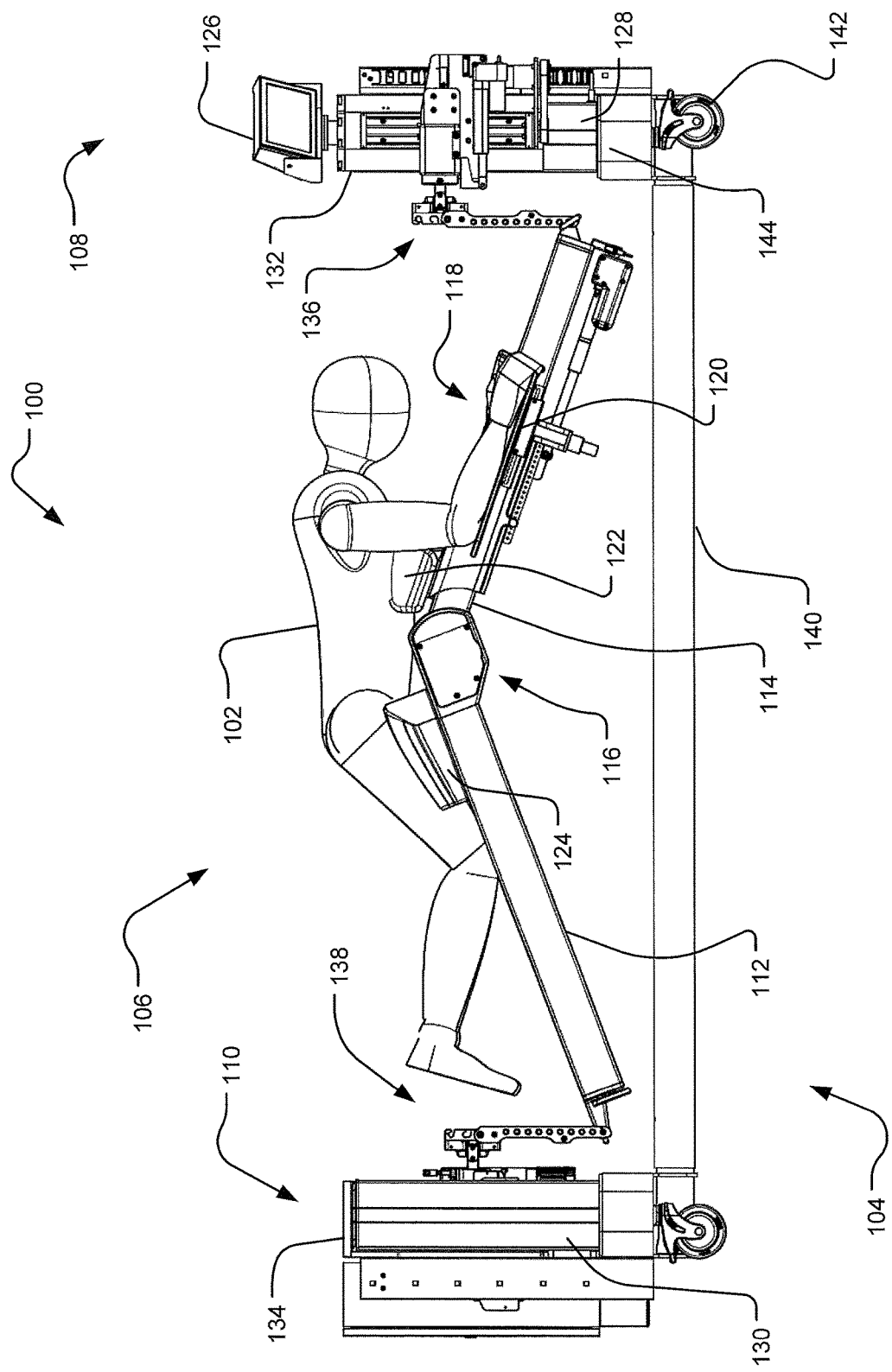
FIG. 3A is a side view of the patient in a prone position on the surgical table in a flexion position.
Figure 3B:
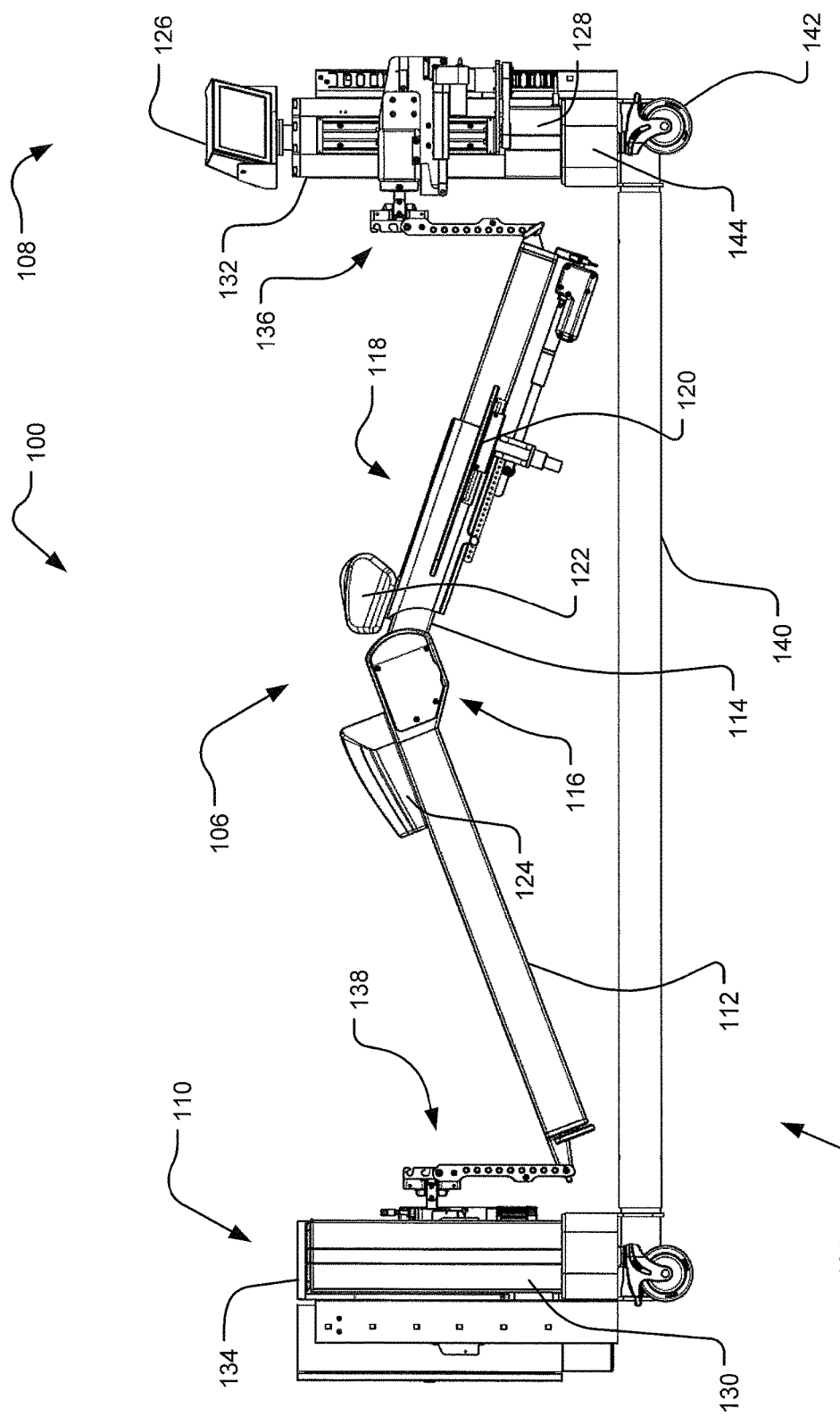
FIG. 3B shows the surgical table of FIG. 3A without the patient.

As can be understood from FIGS. 1A-3B, the user device 126 may be used to articulate the table 100 to and from a neutral position as shown in FIGS. 1A-1D, an extension position illustrated in FIGS. 2A-2D, and a flexion position as shown in FIGS. 3A-3B. As will be detailed herein, the articulation of the table 100 between the various positions while keeping the surgical field stationary is facilitated by the hinges 116.

In one implementation, the patient support 106 includes a plurality of pivot points each on a pitch axis for articulating the table 100 to and from a neutral position, an extension position, and a flexion position. The plurality of pitch axes are substantially parallel to each other and run substantially perpendicular to the longitudinal length of the frame of the patient support 106. Depending on the orientation of the patient support 106, the pitch axes may be parallel with or intersection the plane of the floor. The patient support 106 is configured for movement about each of the pitch axes. In one implementation, a first pitch axis intersects a pair of virtual pivot points located at the points of contact between the skin of the patient 102 and the hip pads 124. The first pitch axis enables the movement to and from the neutral position, the extension position, and the flexion position.

A second pitch axis may be located at a connection point of the foot end frame 112 to the foot end 110 of the base 104, and a third pitch axis may be located at a connection point of the head end frame 114 to the head end 108 of the base 104. The second and third pitch axes enable movement of the patient support 106 relative to the base 104, for example, to and from the Trendelenburg and reverse Trendelenburg positions. The maximum movement relative to the second and third axes depends on a minimum height and a maximum height of the roll assemblies 136, 138.

In one implementation, the hinges 116 are located relative to the first pitch axis and configured to move the patient support 106 to and from the neutral position, the extension position, and the flexion position. The hinges 116 are generally centrally located along a length of the patient support 106, connecting the foot end frames 112 to the head end frames 114. In one implementation, each of the hinges 116 provides an arc of motion with a radius extending from a pivot point along a plane substantially perpendicular to the first pitch axis.

The patient support 106 is configured to drive the hinge 116 along the arc of motion to move the patient support 106 between a maximum extension position and a maximum flexion position. The maximum positions are determined based on the biomechanics of the patient 102, such that the spine of the patient 102 and additionally or alternatively the hips of the patient 102 may be flexed and extended a maximum amount. In one implementation, the maximum amounts of flexion and extension are selected to prevent injury of the patient 102 while provided an appropriate lordosis for a spinal surgery. For example, the maximum flexion may be approximately 40 degrees, and the maximum extension may be approximately 30 degrees. However, other amounts are contemplated based on the needs of one or more of the medical procedure, the patient 102, safety and industry operating standards, and the like.

In one implementation, each of the hinges 116 is actuated by a driver disposed relative to the foot end frame 112. As will be discussed in greater detail herein, the driver for the hinge 116 moves a tube longitudinally within the foot end frame 112 to displace a drive link towards and away from the head end 108. Displacing the drive link moves a chain drive, thereby moving a faceted surface of a sprocket along the arc of motion. The movement of the faceted sprocket causes the patient support 106 to articulate to the neutral, extension, and flexion positions. To articulate the patient support 106 to the flexion position as shown in FIGS. 3A-3B, the driver moves the tube, actuating the faceted sprocket towards the head end 108, and to articulate the patient support 106 to the extension position as shown in FIGS. 2A-2D, the driver moves the tube, actuating the faceted sprocket towards the foot end 110.

In one implementation, the surgical table 100 is configured to articulate to various positions while keeping the surgical field stationary. Stated differently, the virtual pivot points intersected by the first pitch axis remain stationary while the surgical table 100 moves around them. The virtual pivot points have a height above the base frame member 140 that is substantially constant throughout movement of the hinge 116 to the various illustrated in FIGS. 1A-3B.

Referring to FIGS. 1A-1D, in one implementation, when the patient support 106 is positioned with the hinges 116 in the neutral position, such that neither the spine nor hips of the patient 102 are flexed or extended, the virtual pivot point is located at a selected height from the base frame member 140 or the floor. The selected height may be determined based on convenience or comfort for the medical personnel performing the medical procedure on the patient 102. For example, the selected height may be approximately 48 inches.

Turning to FIGS. 2A-2D, when the hinges 116 are actuated from the neutral position to the extension position, extending the hips and spine of the patient 102, the selected height of the virtual pivot points remains substantially unchanged. Similarly, referring to FIGS. 3A-3B, when the hinges 116 are actuated from the neutral position to the flexion position, flexing the hips and spine of the patient 102, the selected height of the virtual pivot points remains substantially unchanged. In one implementation, the selected height of the virtual pivot points remains substantially unchanged when moving the patient support 106 to the Trendelenburg and reverse Trendelenburg positions.

To keep the virtual pivot points stationary during the articulation of the table 100 between the extension, neutral, and flexion positions, the overall length of the patient support 106 and/or the orientations of the various components of the head end 108 and the foot end 110 may change to compensate for the movement of the patient support 106. Stated differently, because the base 104 is fixed in position by the base frame member 140, such that the movable base ends 144 are fixed relative to each other, a change in a height in one or both of the linear actuators 128, 130 and/or the secondary elevator mount assemblies 132, 134 changes the distance between the roll assemblies 136 and 138. When the distance between the roll assemblies 136 and 138 increases or decreases, the length of the patient support 106 changes a complementary amount using various components providing lateral translation compensation.

As such, in one implementation, when articulating to the extension position, the primary and secondary elevators 130, 134 of the foot end 110 and the primary and secondary elevators 128, 132 of the head end 108 of the base 104 move vertically upwards from the base frame member 140 while the actuator in the head end 108 extends the head end frame 114. When articulating to the flexion position, the linear actuators 128, 130 and the secondary elevator mount assemblies 132, 134 of the foot end 110 and the head end 108 of the base 104 move vertically downwards towards the base frame member 140 while the actuator in the head end 108 moves for active linear translation compensation. In other words, the head end 108 and the foot end 110 are fixed relative to each other, so as the patient support articulates between extension, flexion, and neutral, the overall length of the patient support 106 changes.

In one implementation, as described herein, a lateral translation compensation subassembly is positioned at the head end frames 114. The lateral translation compensation subassembly includes a drive mount plate 168 connected to the right and left head end frames 114 that is configured to telescope outwardly and inwardly from the head end frames 114 to lengthen and shorten the head end frames 114 when the patient support 106 is moved to various positions. The lateral translation compensation subassembly also includes a translation driver disposed within or next to the head end frames 114 and configured to actuate the telescoping of the drive mount plate 168.

Figure 4A:
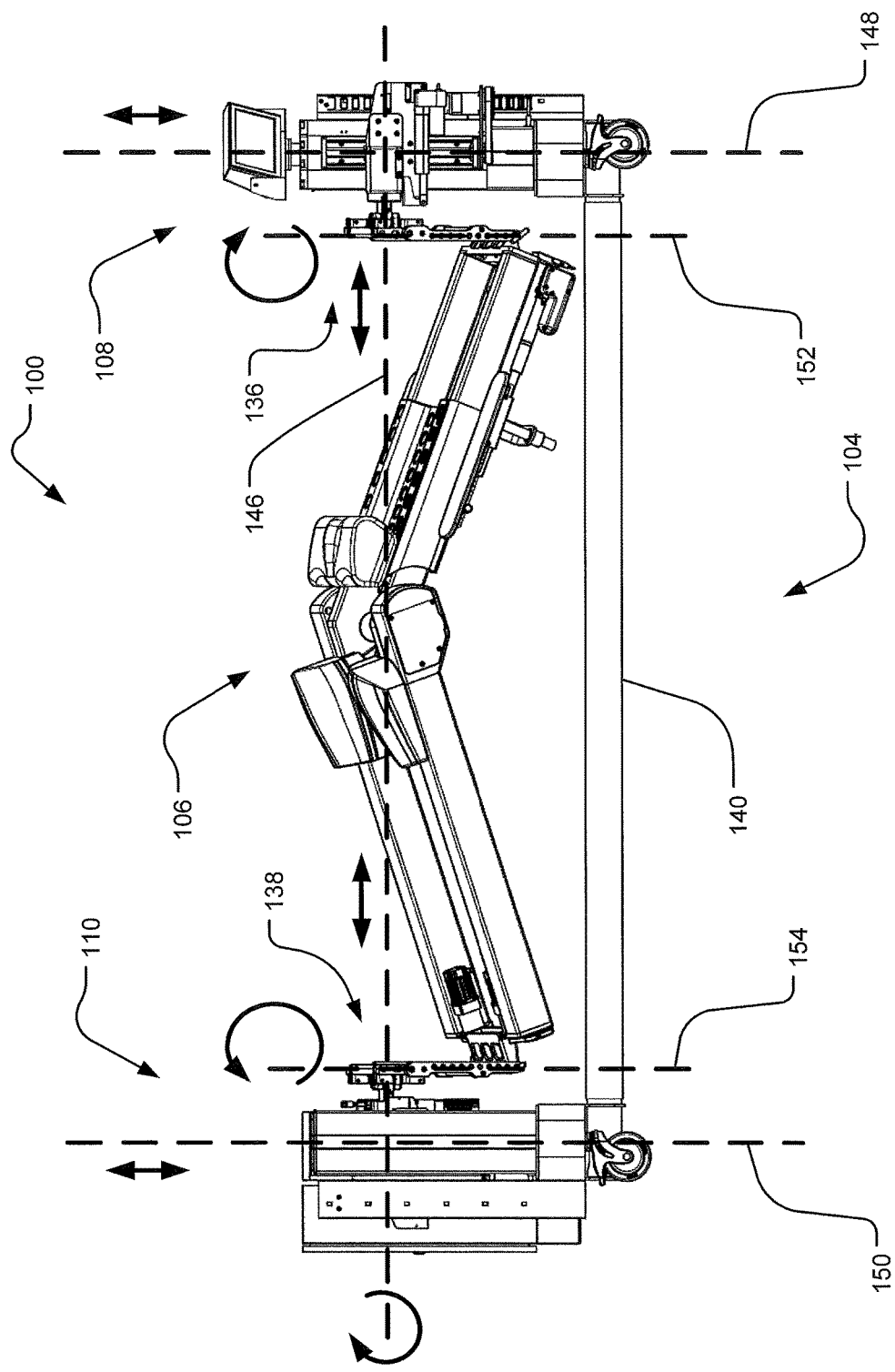
FIG. 4A is a side view of the surgical table with the patient support rolled and illustrating the various motions of the surgical table.
Figure 4B:
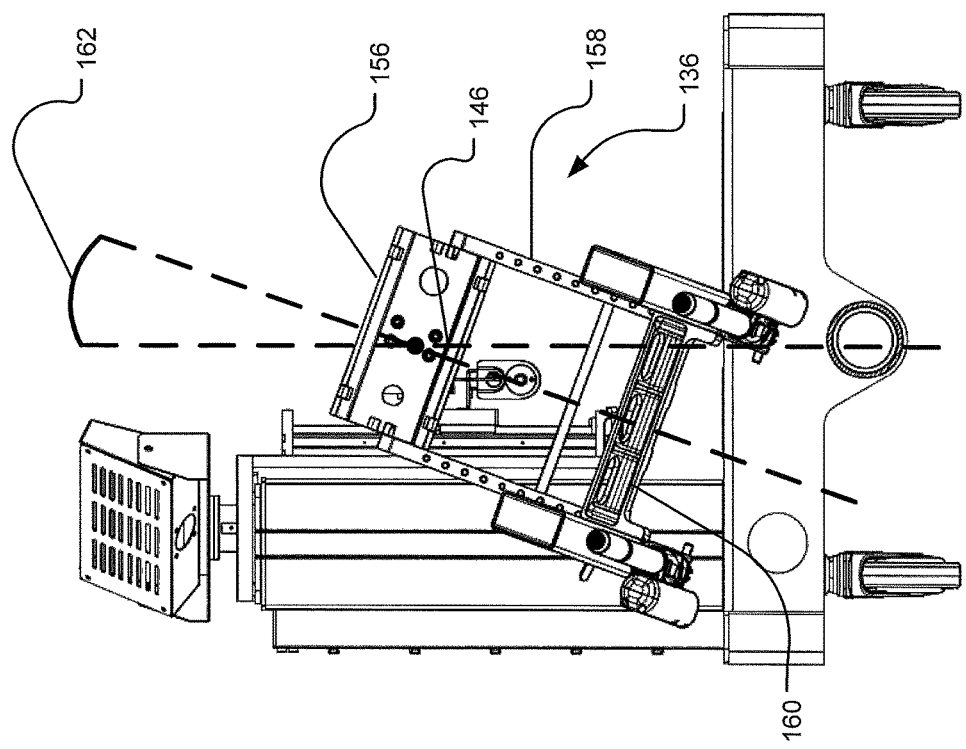
FIG. 4B is a head-end view of the surgical table of FIG. 4A.
Figure 4C:
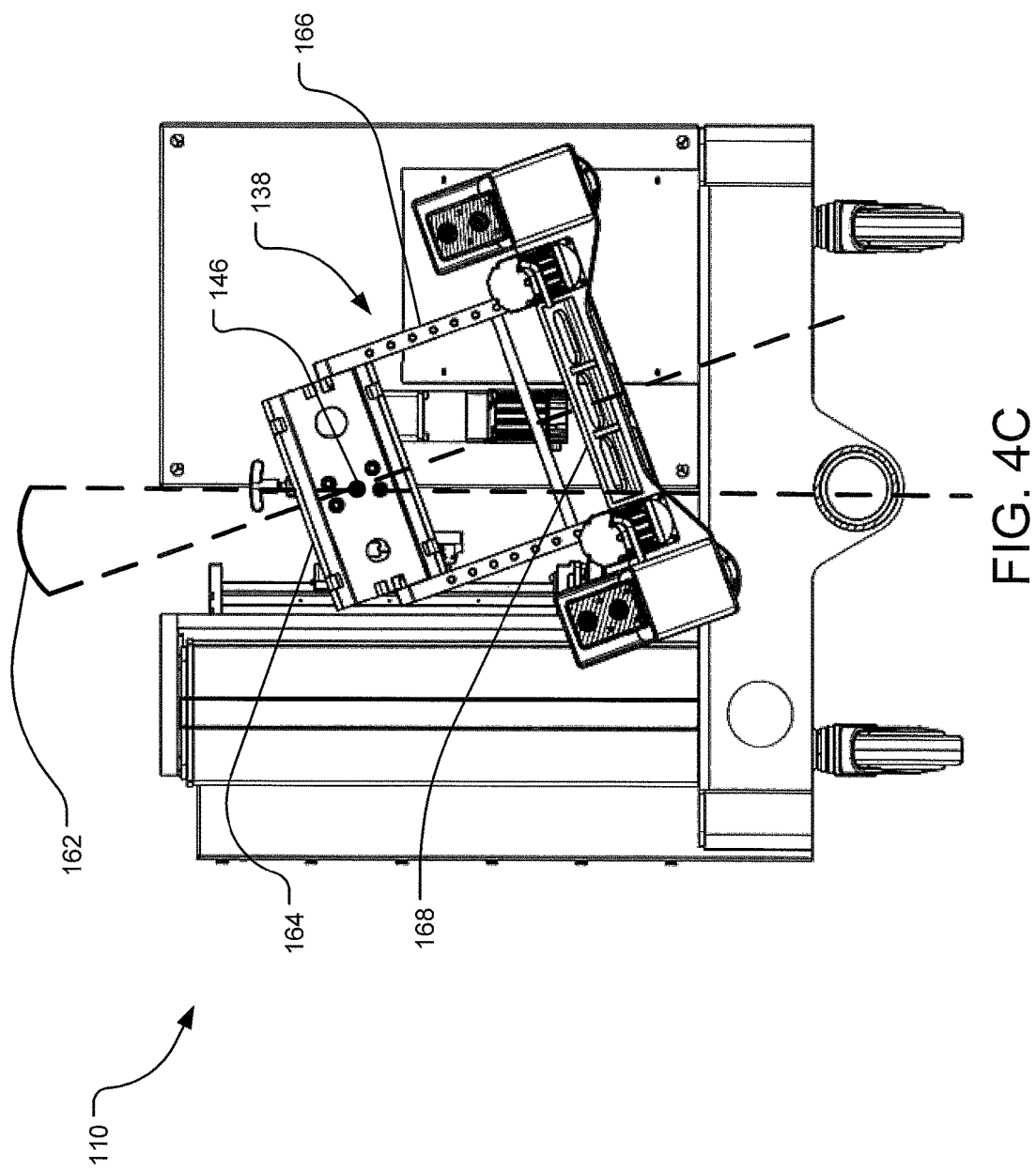
FIG. 4C is a foot-end view of the surgical table of FIG. 4A.

For a detailed description of the movement of the table 100 relative to a plurality of axes reference is made to FIGS. 4A-4C. In one implementation, the plurality of axes includes, without limitation, a longitudinally extending roll axis 146, a head end vertical axis 148, a foot end vertical axis 150, a head end yaw axis 152, and a foot end yaw axis 154.

As can be understood from FIGS. 4A-4C, in one implementation, the roll axis 146 extends longitudinally along a length of the patient support 106 through brackets 156, 164 of the roll assemblies 136, 138 at the head end 108 and the foot end 110, such that the roll axis 146 is substantially coaxial with rotation shafts of the roll assemblies 136, 138. As described in detail herein, in one implementation, the bracket 156 at the head end 108 is connected to a cross bar 160 with a frame 158, and the bracket 164 is connected to a drive mount plate 168 with a frame 166. The cross bar 160 connects to the foot end frames 112, and the drive mount plate 168 connects to the head end frames 114.

In one implementation, the base 104 is configured to tilt, roll, turn, or rotate the patient support 106 about the roll axis 146. As can be understood from FIGS. 4A-4C, to improve access to a surgical site on the patient, the patient support 106 may be power rolled to an angle 162 relative to a plane substantially perpendicular to the base frame member 140 and intersecting the roll axis. The angle 162 may be towards the right or left of the table 100 about the roll axis. In one implementation, the angle 162 is approximately 25 degrees. However, other amounts of roll movement is contemplated. The patient support 106 may be locked into a roll position to provide stability while performing the medical procedure.

The dual offset uprights in the head end 108 and foot end 110 include at least one vertical translation axis. As can be understood from FIG. 4A, the linear actuator 128 and the secondary elevator mount assembly 132 providing vertical translation in the head end 108 along the head end vertical axis 148 and the linear actuator 130 and the secondary elevator mount assembly 134 providing vertical translation in the foot end 110 along the foot end vertical axis 150. Vertical translation of at least a portion of the patient support 106 may occur along one or both of the vertical axes 148, 150. Furthermore, the vertical translation along the vertical axes 148, 150 may be synchronous or asynchronous and/or at different rates of vertical movement. Depending on the positioning of the patient 102, vertical translation along the vertical axes 148, 150 may occur in the same or opposite directions and/or at the same or different distances, thereby moving the orientation of the roll axis 146 relative to the base frame member 140 and positioning the head end 108 and the foot end 110 at different heights.

In one implementation, the head end primary and secondary elevators, including the linear actuator 128 and the secondary elevator mount assembly 132, have a minimum and a maximum translation distance along the head end vertical axis 148, and the foot end primary and secondary elevators, including the linear actuator 130 and the secondary elevator mount assembly 134, have a minimum and a maximum translation distance along the foot end vertical axis 150. The maximum translation distances are the maximum height the head and foot end primary and secondary elevators may be telescoped or otherwise extended in a direction away from the base frame member 140. For example, the maximum translation distances may reflect the highest that the rotation shafts of the roll assemblies 136 and 138 may be positioned above the base frame member 140. The minimum translation distances are the minimum height the head and foot end primary and secondary elevators may be telescoped or otherwise contracted in a direction towards the base frame member 140. For example, the minimum translation distances may reflect the lowest that the rotation shafts of the roll assemblies 136 and 138 may be positioned above the base frame member 140.

The dual offset uprights in the head end 108 and foot end 110 include at least one yaw axis. As can be understood from FIG. 4A, in one implementation, the head end roll assembly 136 includes the head end yaw axis 152, and the foot end roll assembly 138 includes the foot end yaw axis 154. When the patient support 106 is positioned substantially parallel to the base frame member 140 and not rolled about the roll axis 146, the yaw axes are substantially perpendicular to the base frame member 140 and substantially parallel to the vertical axes 148, 150. The table 100 is configured to rotate at least a portion of the patient support 106 about the yaw axes 152 and/or 154 to prevent buckling or collapse of the patient support 106 when positioned, for example, in the Trendelenburg and reverse Trendelenburg positions in conjunction with a roll.

As described herein, the patient support 106 is configured for movement with respect to a plurality of axes, such as the roll axis 146, the vertical axes 148 and 150, and the yaw axes 152 and 154. The movement may occur simultaneously or sequentially with respect to two or more of the axes. Further, the drive mount plate 168 may be connected to the right and left head end frames 114 and configured to telescope outwardly and inwardly from the head end frames 114 to lengthen and shorten the head end frames 114 when the patient support 106 is moved to various positions.

In one implementation, the table 100 is configured for 180 degree sandwich-and-roll movement. The patient 102 is reversibly sandwiched between the patient support 106 and another patient support and rotated about the roll axis 146.

Figure 5A:
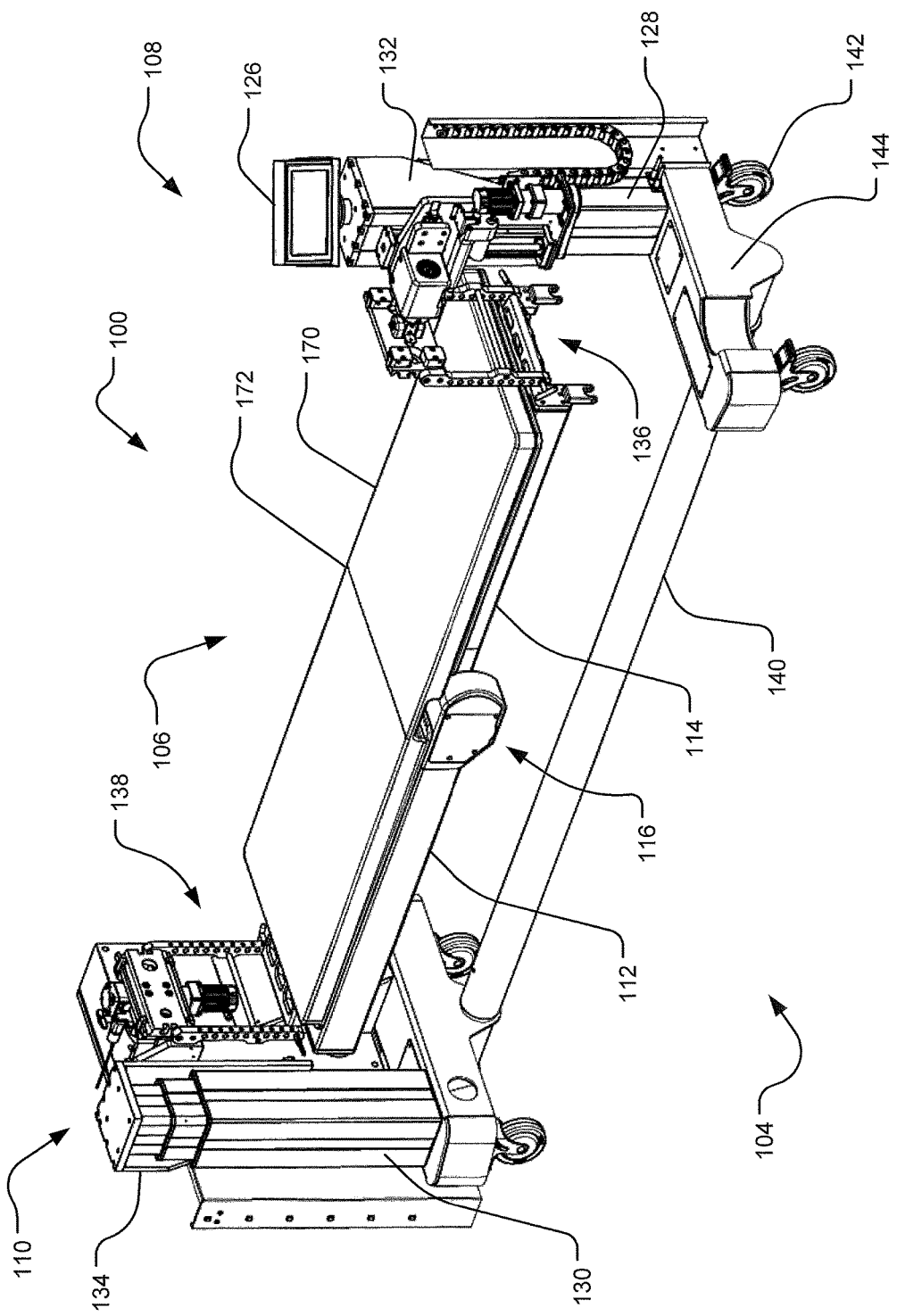
FIG. 5A is an isometric view of the surgical table in the neutral position with a trunk translator and support pads replaced with an imaging pad.
Figure 5B:
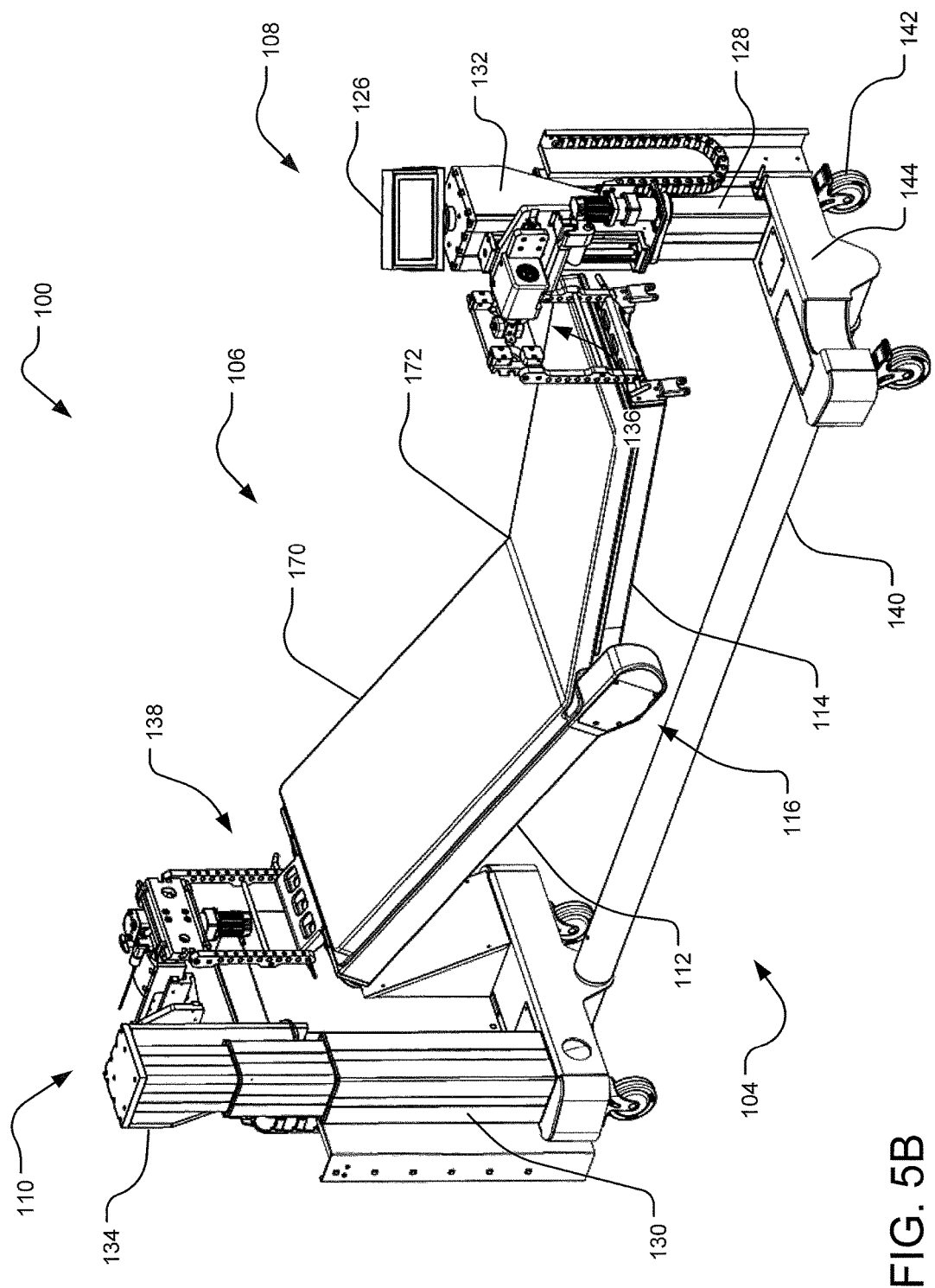
FIG. 5B is the surgical table of FIG. 5A in the extension position.
Figure 5C:
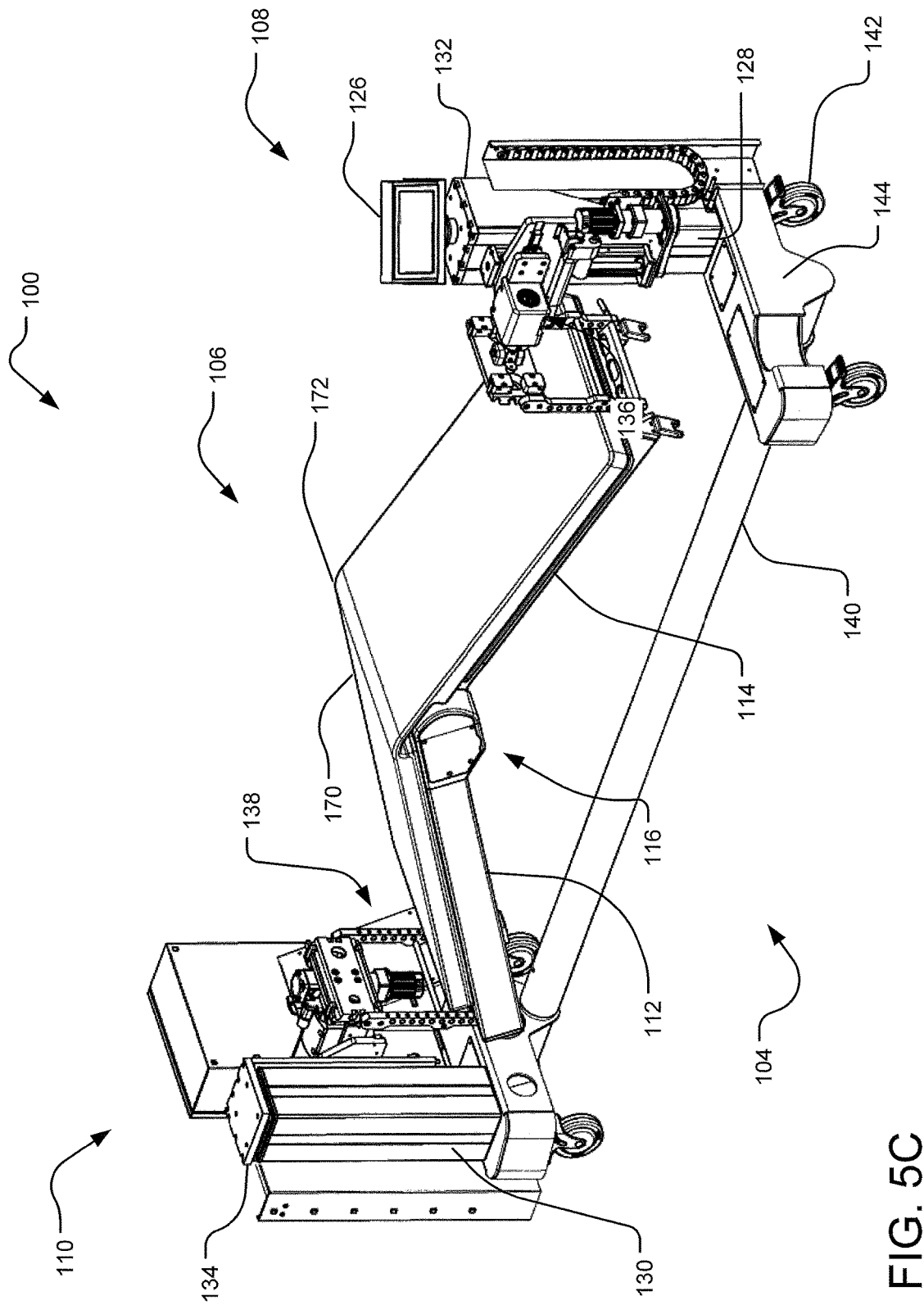
FIG. 5C is the surgical table of FIG. 5A in the flexion position.

Turning to FIGS. 5A-5C, the trunk translator 118 and the support pads 120, 122, and 124 are removed and replaced with a flexing flat top or imaging top 170 that is configured to bend along a line 172 as the patient support 106 is moved to various positions. In one implementation, the patient support 106 illustrated in FIGS. 5A-5C may be used to support the patient 102 in the supine position, lateral decubitus position, etc. The patient support 106 with the imaging pad 170 may be articulated as described herein from the neutral position as shown in FIG. 5A to the extension position depicted in FIG. 5B to the flexion position as shown in FIG. 5C.

In one implementation, the secondary elevator mount assemblies 132 and 134 are located to the medial sides of the dual-column base offset uprights and support the use of a flexing flat top or imaging top 170. The top 170 may be used, for example, for lateral decubitus positioning so the patient 102 can be low enough to operate on and be imaged without being moved.

Figure 6:
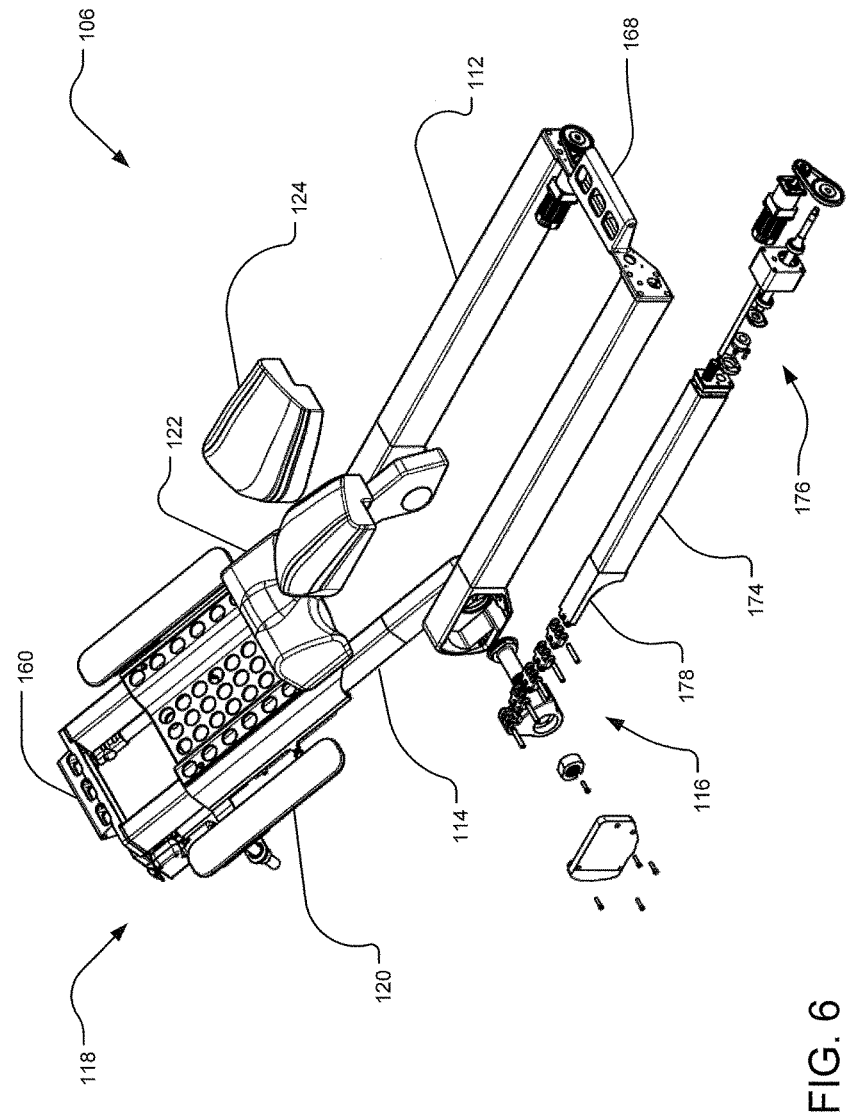
FIG. 6 is an exploded view of the patient support.

To begin a detailed discussion of the patient support 106, reference is made to FIG. 6, which is an exploded view of the patient support 106. In one implementation, the trunk translator 118 includes arms slidably mounted on the head end frames 114. In other words, the arms are hollow with the head end frames 114 extending therethrough, such that the trunk translator may be moved along the length of the head end frames 114 to compensate for the movement to the various positions described herein to keep the upper body of the patient 102 stationary and prevent compression or stretching of the skin or spine of the patient 102. The movement of the trunk translator 118 is driven by a trunk translator linear actuator.

In one implementation, to move the patient support 106 to the neutral, extension, and flexion positions, each of the hinges 116 are actuated using a respective driver 176, which drives a tube 174 extending through a lumen 184 of the foot end frame 112. The tube 174 is configured to move within the foot end frame 112 and may be a variety of shapes including, without limitation, cylindrical, rectangular, and the like. In certain implementations, the tube 174 is rectangular and matches the shape and size of the lumen 184. In one implementation, a drive link 178 extends from the head end of the tube 174, such that when the driver 176 moves the tube 174, the drive link 178 is moved accordingly, thereby actuating the hinge 116.

Figure 7:
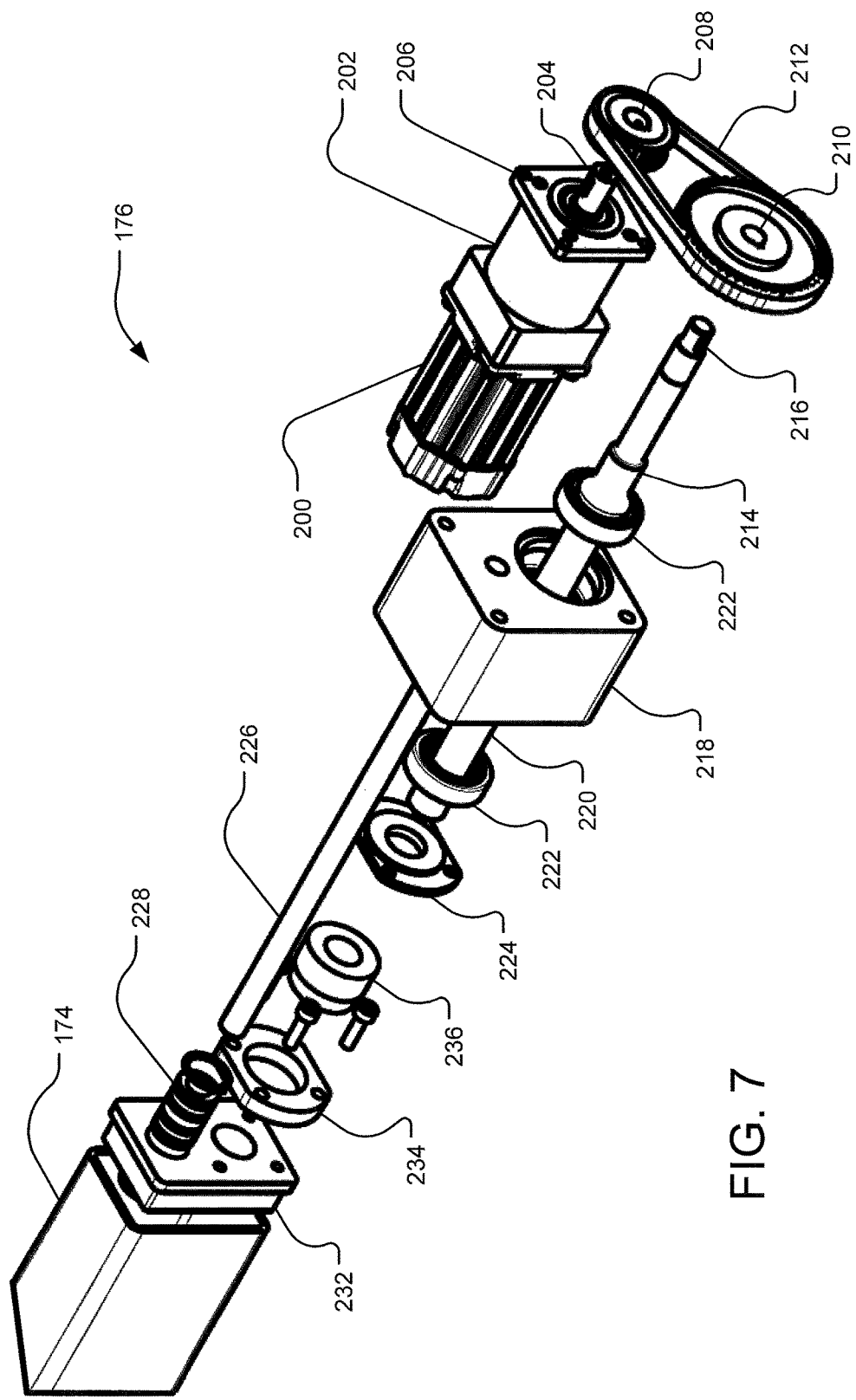
FIG. 7 is a detailed exploded view of a driver of the patient support.
Figure 8A:
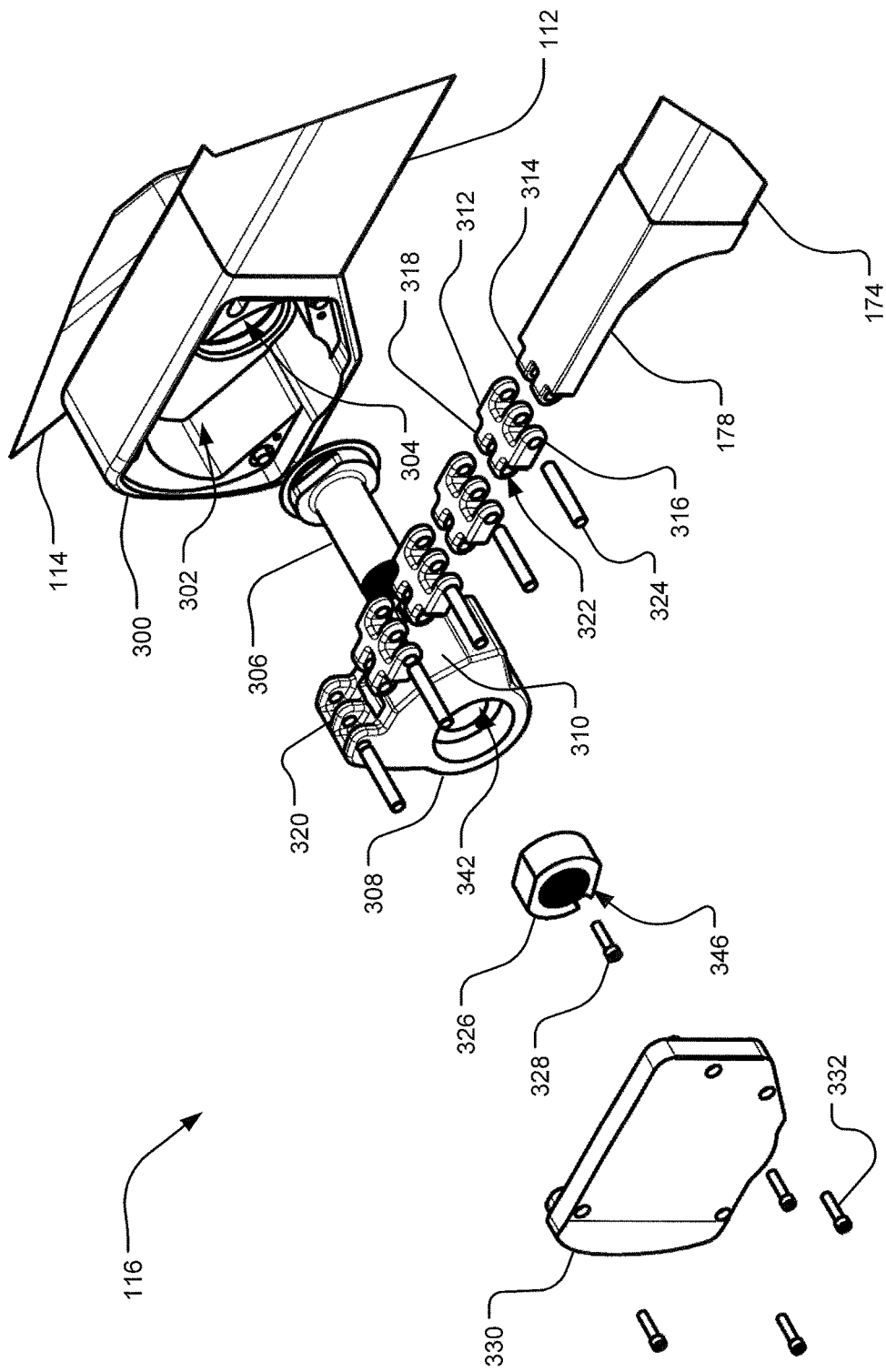
FIGS. 8A and 8B are detailed exploded views of the radiolucent hinge.
Figure 8B:
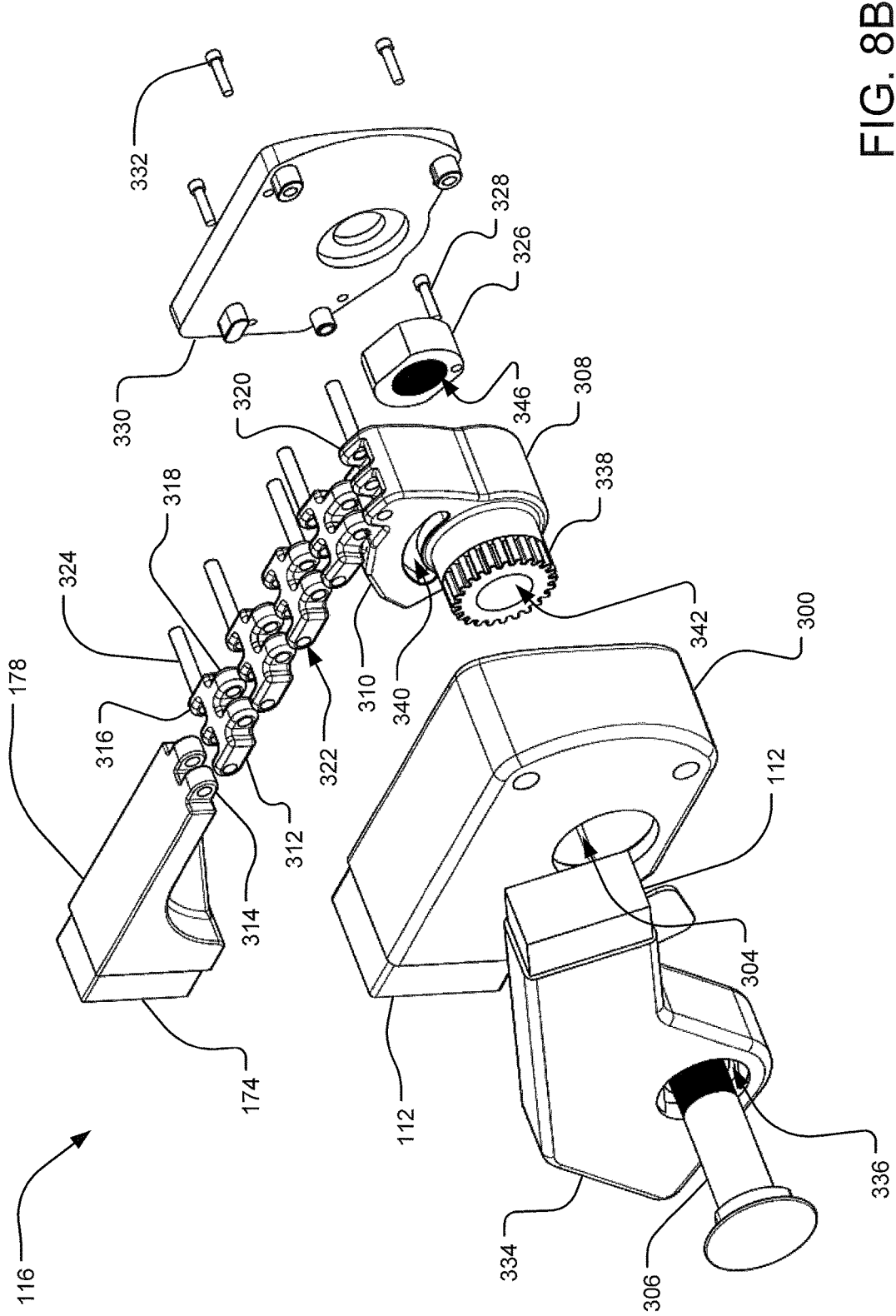

Turning to FIG. 7, an exploded view of the driver 176 is shown. In one implementation, the driver 176 includes a motor 200 extending from a rotation translator 202 having an end 204 extending through a mount 206, which is configured to attach to the foot end roll assembly 136. The end 204 is configured to engage a first pulley 208, which is operably connected to a second pulley 210 via a drive belt 212. The pulleys 208 and 210 may be a variety of sizes with a plurality of teeth. In one implementation, the second pulley 210 is approximately double the size of the first pulley 208. For example, the first pulley 208 may have approximately 25 teeth, and the second pulley 210 may have approximately 50 teeth. The drive belt 212 may be made from a variety of shapes and sizes configured to engage the pulleys 208, 210. For example, the drive belt 212 may be approximately 9 mm in width.

In one implementation, a bearing 214 includes an end 216 configured to engage the second pulley 210. The bearing 214 is sized and shaped to extend into an opening in a bearing housing 218 to drive a lead screw 220. In one implementation, the bearing 214 is a tapered roller having an inner diameter of approximately 15 mm and an outer diameter of approximately 42 mm. Nuts 222 may be used to position and secure the lead screw 220 and the bearing 214. A bearing housing cap 224 secures the lead screw 220 to the bearing housing 218.

A guide shaft 226 is received by and engages a linear bearing 228 extending from a mount 232 attached to the tube 174. The guide shaft 226 positions the lead screw 220 relative to an opening in a mounting flange 234, which is secured to the mount 232 using a lead nut 236. In this way, as the lead nut 236 translates on the rotating lead screw 220, the mount 232, which is coupled with the tube 174, translates within the frame 112 while being prevented from rotating by the guide shaft 226.

During articulation of the patient support 106, in one implementation, the motor 200 rotates the first pulley 208 using the rotation translator 202. Rotation of the first pulley 208 causes the second pulley 210 to rotate simultaneously via the drive belt 212. The rotation of the second pulley 210 causes the lead screw 220 to rotate, while being rotationally supported by the bearing block 218. Rotation of the lead screw 220 causes the nut 236 to longitudinally translate and, thus, translate the tube 174 within the foot end frame 112 towards and away from the head end 114 to actuate the hinge 116. The guide shaft 226 maintains a longitudinal alignment as the nut 236 as it translates along the linear screw 220. In this way, the bearing 214, guide shaft 226, lead screw 220, and nut 236, among other components, act as a translational driver within the foot end frame 112 to cause the tube 174 to longitudinally translate within the foot end frame 112 along a longitudinal length of the foot end frame 112.

To begin a detailed description of the radiolucent hinge 116, reference is made to FIGS. 8A and 8B and FIGS. 9A-9D, which are respectively detailed exploded views of the radiolucent hinge 116 and various views of the assembled hinge 116 shown without the housing or cover. In one implementation, the hinge 116 includes a housing 300 connected to the foot end frame 112. The housing 300 includes a cavity 302 and an opening 304 extending through a wall 378. The cavity 302 may be occluded by a cover 330 and secured with one or more nylon screws 332 to enclose the various internal components of the hinge 116.

In one implementation, the drive link 178 includes a body having protrusions 314 configured to engage a chain driver having a plurality of links 312. Each of the links 312 includes a body having protrusions 318 and indents 316 configured to receive and engage the protrusions 318 of other links and/or the protrusions 314 of the drive link 178, such that openings 322 through the protrusions 314, 318 line up with openings 322 through the indents 316. A sprocket 308 includes indents 320 configured to receive and engage the protrusions 318 of the chain link 312, such that openings 322 through the protrusions 318 line up with openings 322 through the indents 320. Once the openings 322 are lined up at the respective connections of the chain links 312, a drive link pin 324 is inserted through the opening 322 to secure the sprocket 308 to the drive link 178 via the chain driver. In one implementation, each of the links 312 are sized and shaped to lie flat against a faceted surface 310 of the sprocket 308 depending on the actuation of the sprocket 308. Stated differently, the faceted surface 310 is substantially planar and includes a plurality of facets, each configured to abut or contact a bottom surface of one of the links 312 while a top surface of each of the links 312 is configured to abut or contact an inner top surface of the cavity 302, thereby maintaining the chain driver in compression.

It can be difficult to maintain a plurality of links 312 in compression because the links 312 are rotatable at the pins 324 and, therefore, have a tendency to rotate at the pins 324 when a compressive force is acted on the links 312. Thus, the chain driver as described herein is constrained or restricted from certain movements at the pins 324 by the links 312 being sandwiched between the inner top surface of the cavity 302 and the faceted surface 310 of the sprocket 308. In this way, a compressive force along a longitudinal length of the drive links 312 is configured to maintain the links 312 in-line with each other.

In one implementation, the sprocket 308 includes a male spline 338 with an opening 342 extending therethrough. The male spline 338 is configured to engage a female spline 301 of a head end spar attachment 334 connected to the head end frame 114. The female spline 301 is disposed within an opening 336 extending through the head end spar attachment 334. To hold the hinge 116 together, a threaded hinge pin 306 is inserted through the openings 336, 304, 342 and into an opening 346 of a nut 326, which is secured to the sprocket 308 with a nylon screw 328 extending through an cutout 350 in the nut 326.

Figure 9A:
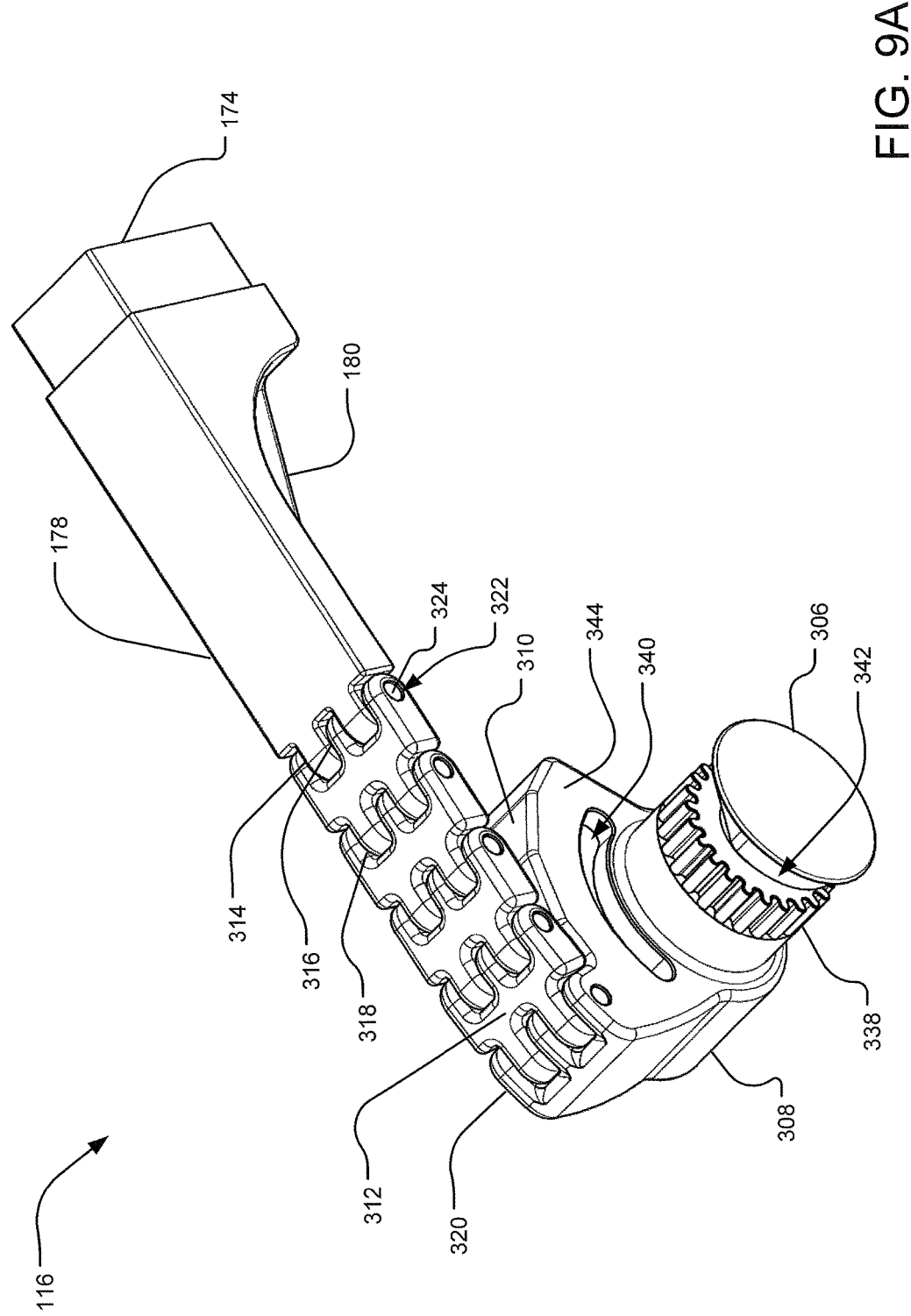
FIG. 9A is a side perspective view of the radiolucent hinge with the housing and foot end frame removed.
Figure 9B:
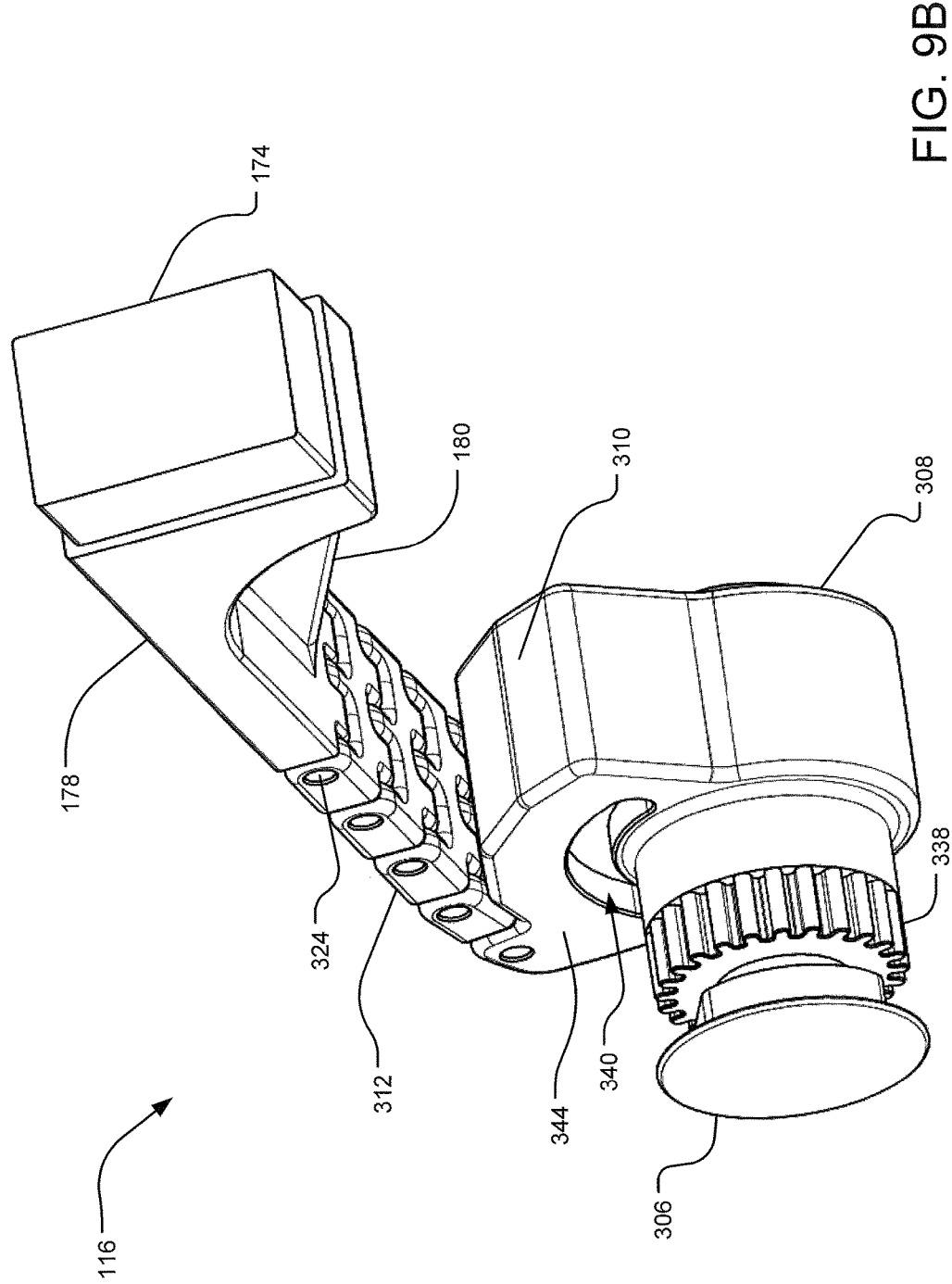
FIG. 9B is a foot end perspective view of the radiolucent hinge of FIG. 9A.
Figure 9C:
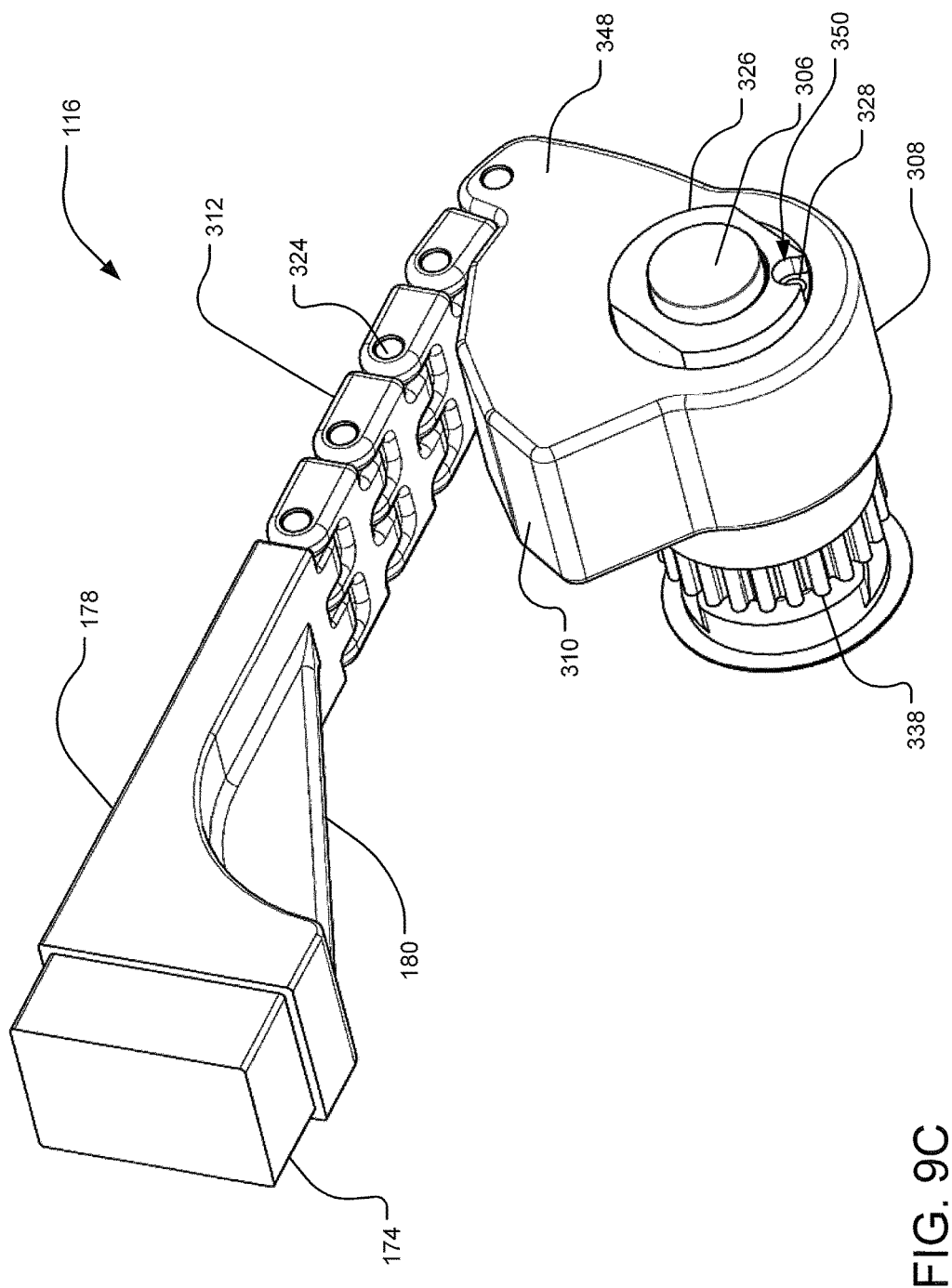
FIG. 9C is another side perspective view of the radiolucent hinge of FIG. 9A.
Figure 9D:
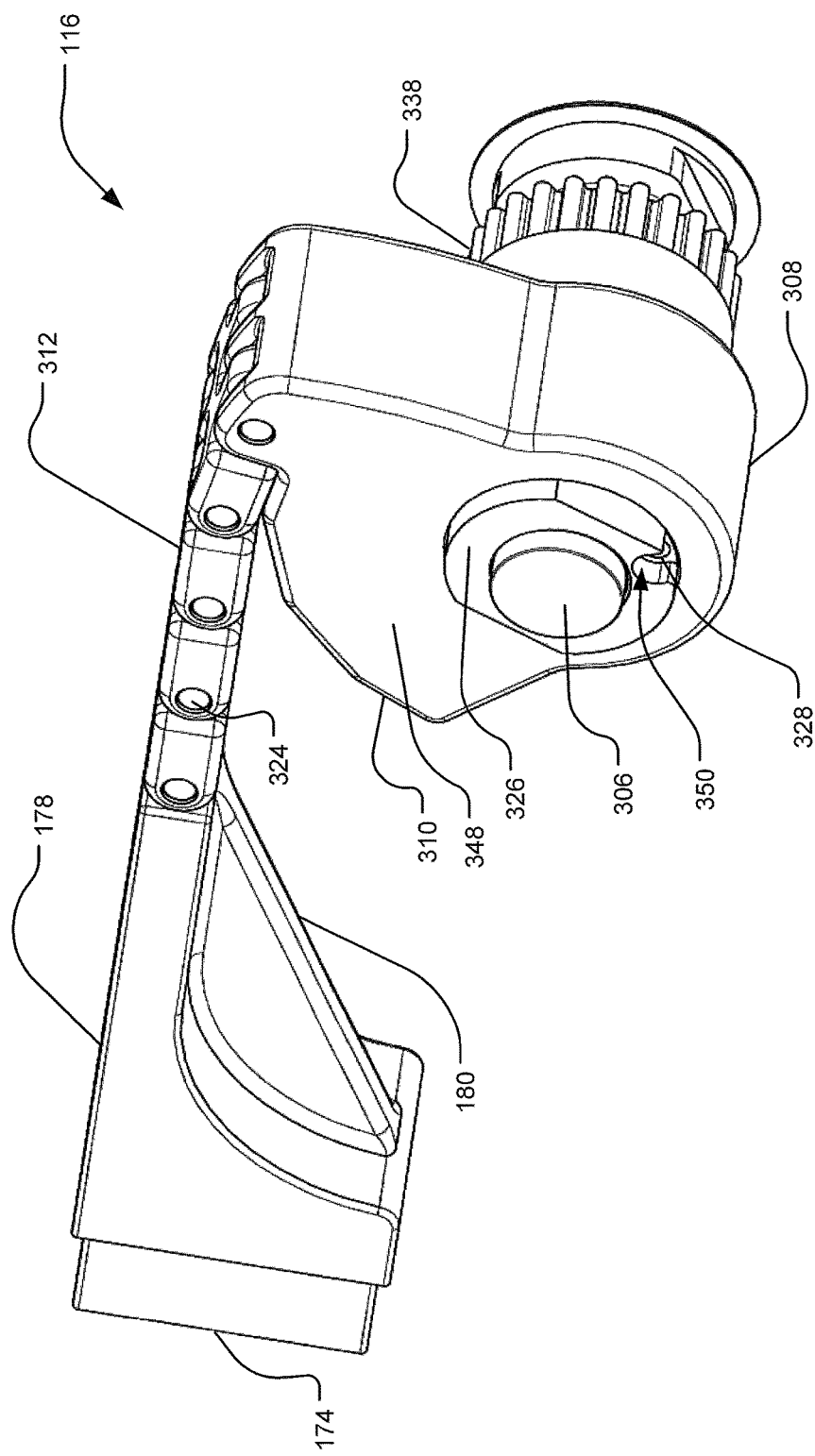
FIG. 9D is a head end perspective view of the radiolucent hinge of FIG. 9A.
Figure 9E:
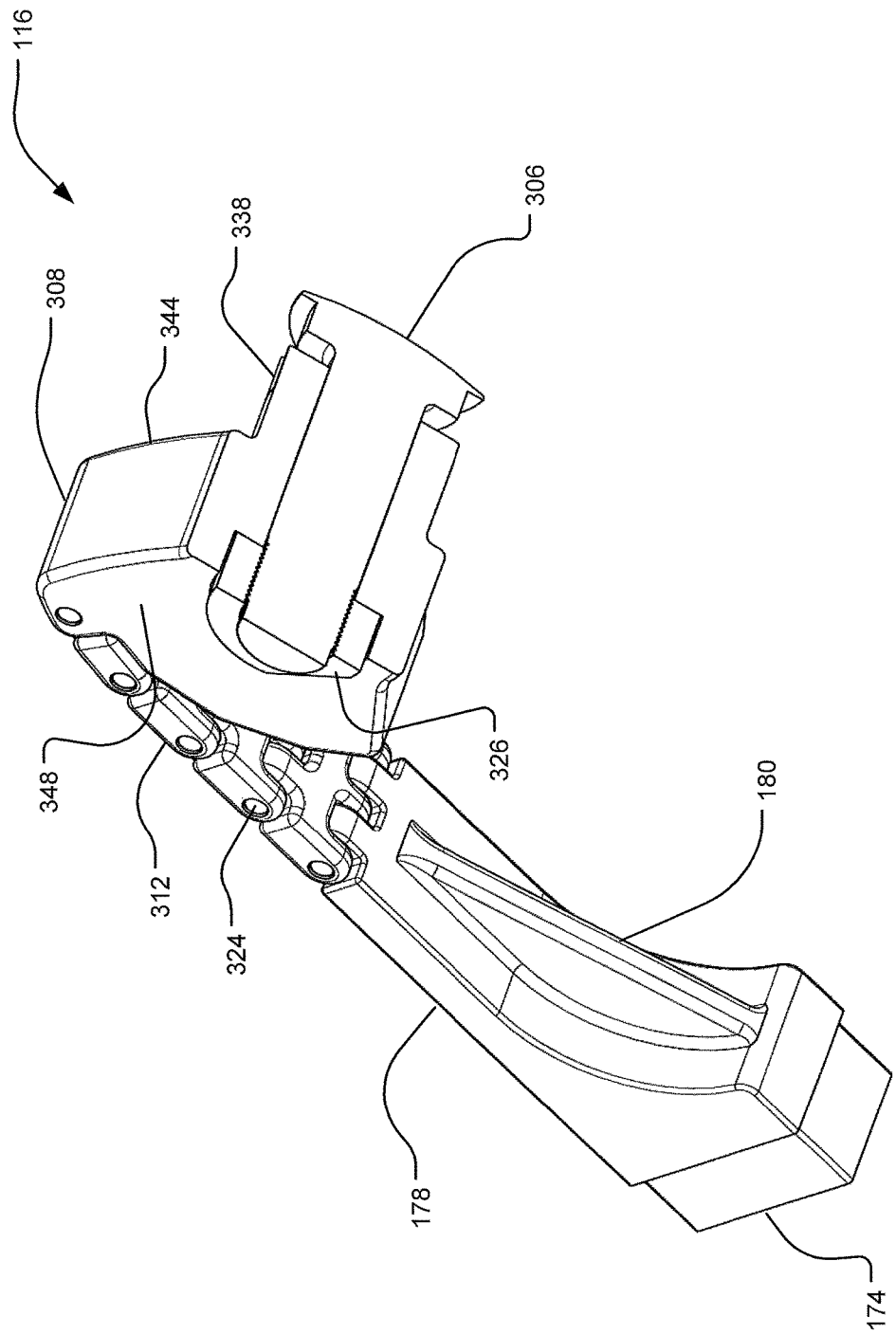
FIG. 9E is a bottom perspective view of the radiolucent hinge of FIG. 9A with a cross section through the faceted sprocket.

Turning to FIGS. 9F-9L, various views of another example radiolucent hinge 810 are shown. As seen in the FIG. 9F, the driver 176 and faceted sprocket 308 remain substantially unchanged from the previously described example of the radiolucent hinge 116 shown in FIGS. 9A-9E, among others. The radiolucent hinge 810 of FIGS. 9F-9L, however, includes a drive chain including drive links 812 that are different from those previously described. More particularly and referring to FIGS. 9F-9G, the drive links 812 are configured to link together without the need for a separate or independent drive link pin to couple the individual drive links 812 together. As seen in FIGS. 9F-9I, there are two types of drive links 812. There is a single male end drive link 814 with a single integrated bearing shaft 816 and a single bearing slot 818. The other type of drive link 812 is a dual-male end drive link 820 with a pair of integrated bearing shafts 816 and no bearing slots. One of the pair of integrated bearing shafts 816 of the dual-male end drive link 820 is configured to pivotally couple with a cylindrical bearing slot 822 formed within the end of the driver 176. The other of the pair of integrated bearing shafts 816 is configured to pivotally couple with a bearing slot 818 of an adjacent single male end drive link 814. Opposite the bearing slot 818 of the single male end drive link 814 is the integrated bearing shaft 816 that is configured to pivotally couple with another, adjacent single male end drive link 814. In total, the radiolucent hinge 810 as shown in FIG. 9F includes one dual-male end drive link 820 and three single male end drive links 814. The integrated bearing shaft 816 of the last of the three single male end drive links 814 is configured to pivotally couple with a bearing slot 824 formed in the faceted sprocket 308.

Figure 9I:
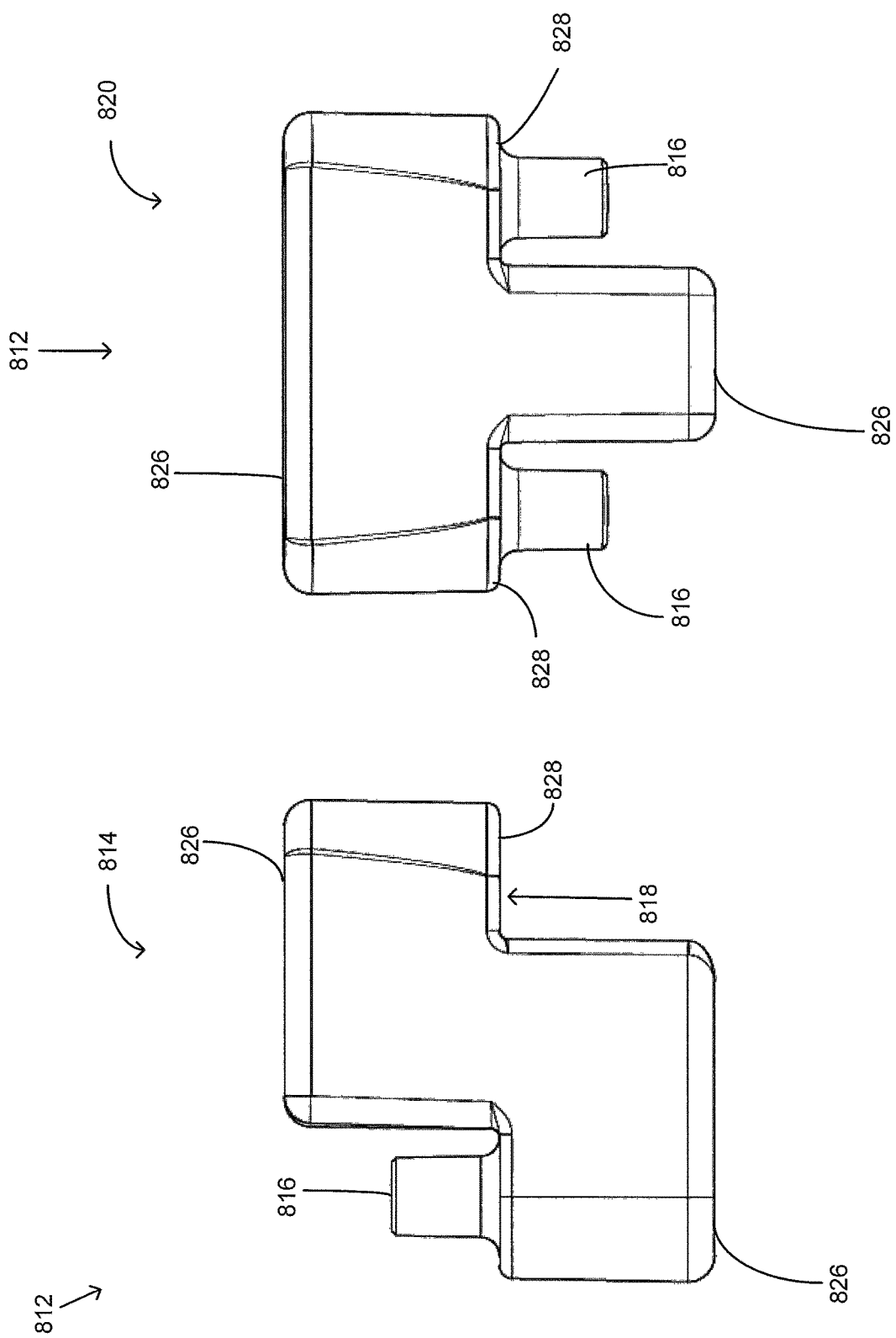
FIG. 9I is a side view of the links of the radiolucent hinge of FIG. 9F.

As seen in FIGS. 9H-9I, which are perspective and side views of the single and dual-male end drive links 814, 820, the integrated bearing shafts 816 are cylindrical and configured to pivot within the reciprocally shaped bearing slots 818 of adjacent drive links 812. The drive links 812 couple together such that end surfaces 826 of adjacent drive links 812 substantially align with each other to form the drive chain. In this orientation, the integrated bearing shafts 816 are matingly received within the bearing slots 818 of adjacent drive links 812. As seen in the figures, the integrated bearing shaft 816 extends from a medial surface 828 about half way to the end surface 826. Correspondingly, the bearing slots 818 extend into the drive link 812 from the medial surface 828 about half way to the end surface 826.

Figure 9J:
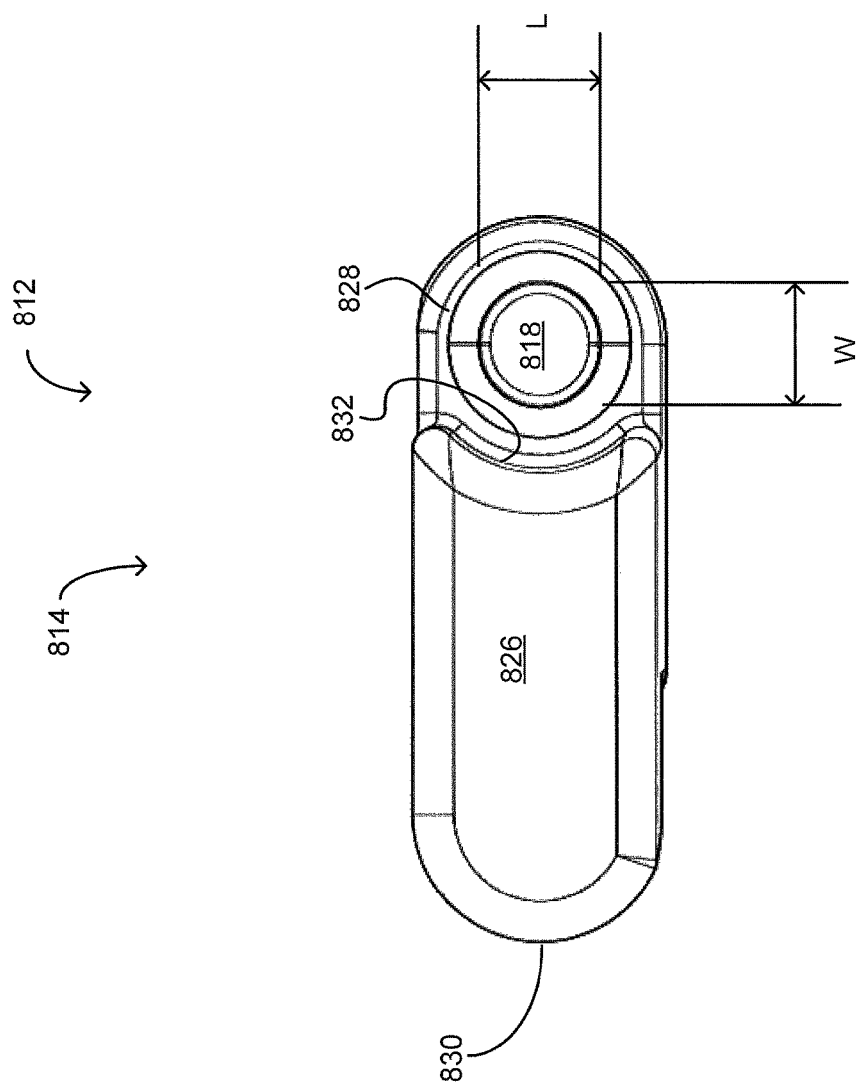
FIG. 9J is a top view of a single male end drive link of the radiolucent hinge of FIG. 9F.
Figure 9K:
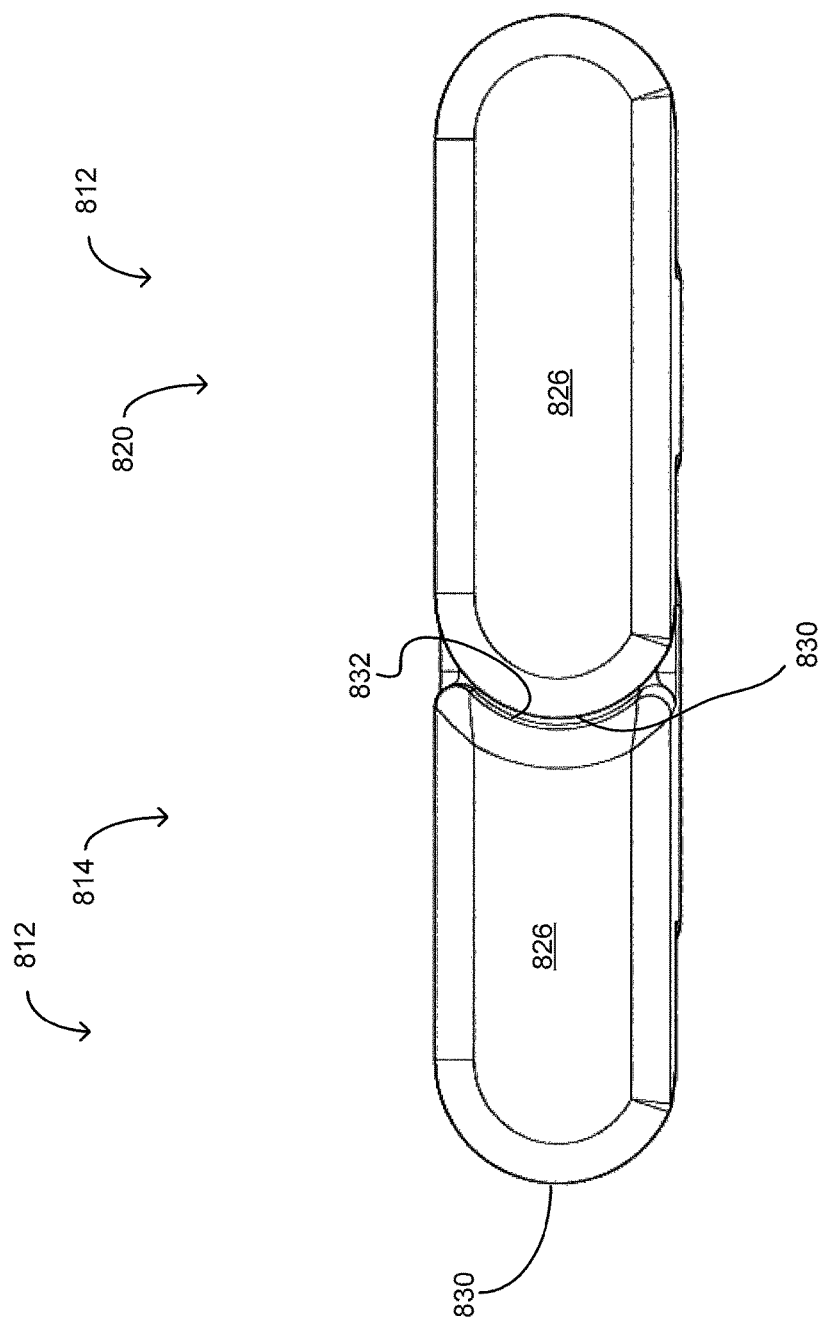
FIG. 9K is a top view of a single male end drive link coupled with a dual male end drive link in an unloaded state.
Figure 9L:
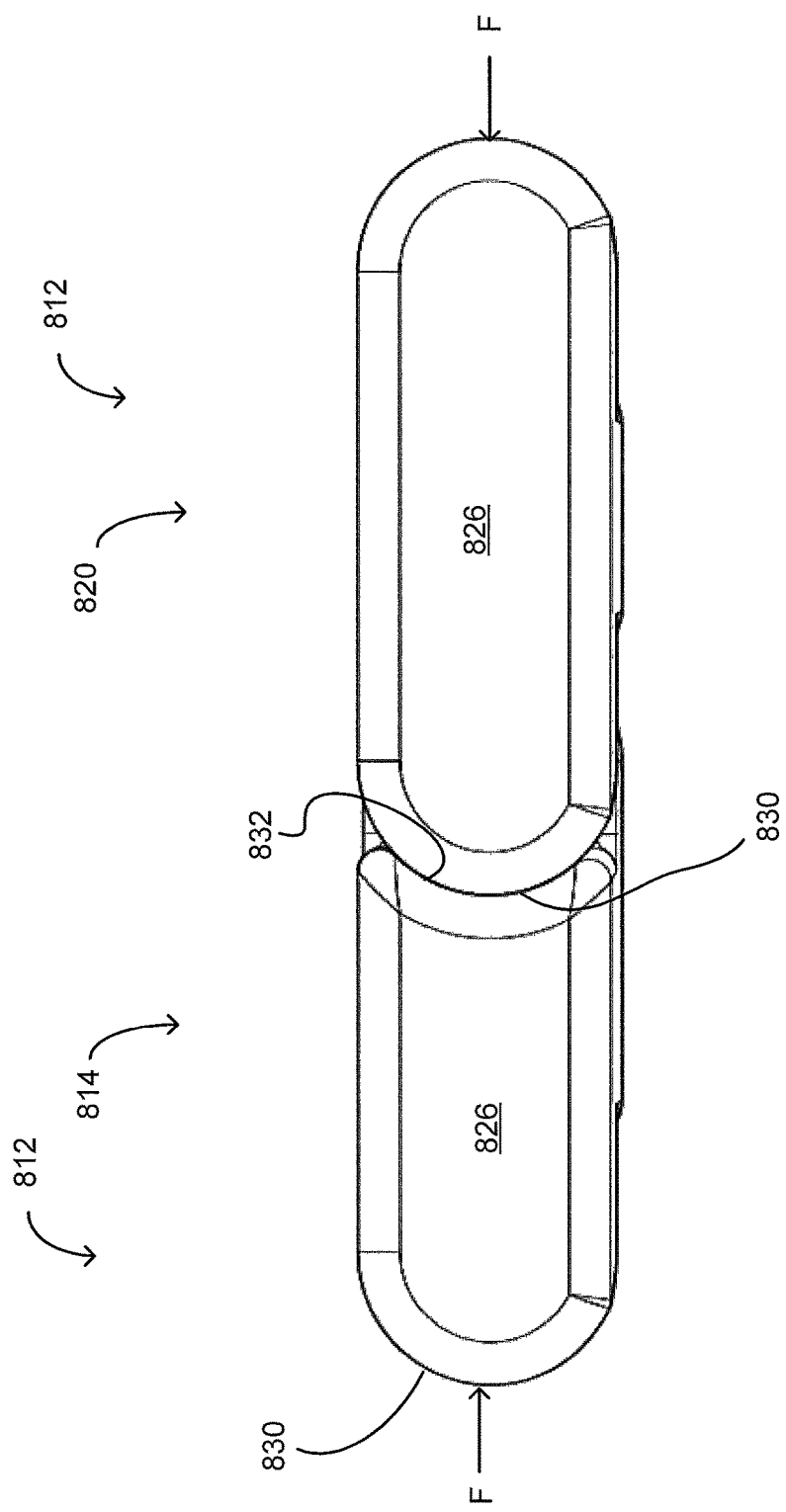
FIG. 9L is a top view of a single male end drive link coupled with a dual male end drive link in a loaded state.

As seen in FIG. 9J, which is top view of a single male end drive link 814, the bearing slot 818 is slotted such that it is not a completely circular bore extending into the medial surface 828; rather, the slot 818 is wider W than it is long L. In this way, the integrated bearing shaft 816 may be received within the bearing slot 818 during assembly, for example, with a small amount of "play", in the direction of the width W, between the shaft 816 and slot 818. This type of unloaded state can be seen in FIG. 9K. More particularly, in the unloaded state, a convex, bullnose surface 830 of the forward end of the drive link 812 is slightly spaced apart from (i.e., small amount of "play") a concave surface 832 of a back end of an adjacent drive link 812. Upon applying a compressive load F, as seen in FIG. 9L, which shows a pair of drive links 812 in a loaded state, the bullnose surface 830 of the forward end of the trailing drive link 812 makes contact with the concave surface 832 of the back end of the adjacent drive link 812. In this way, a compressive force of the drive chain is focused on the pivoting and frictional contact between the opposing convex and concave surfaces 830, 832 of the drive links 812 and not on the bearing shafts 816 and slots 818. This reduces or eliminates potential shear forces that would otherwise be caused by applying the compressive load to the bearing shafts 816 if the slots 818 were cylindrical.

The bearing shafts 816 and slots 818 aid in orienting drive links 812 during assembly and disassembly, but, upon loading, the forces between the drive links 812 are placed on the body of the drive links 812. In this way, using integrated bearing shafts 816 and slots 818 for the drive links 812 reduces the parts required for the hinge 810 by eliminating the need for a separate drive link pin as well as reduces the shear stresses involved by placing the compressive loading on the drive links 812 themselves instead of on a pin. Additionally, when the assemblage of drive links 812 is put in tension, for example, when the patient support 106 is rolled, the drive links 812 maintain their orientation in an assembled chain because the integrated bearing shafts 816 are received within an adjacent drive links 812 bearing slot 818.

Turning to FIGS. 10A and 10B, side perspective views of the faceted sprocket 308 of the radiolucent hinge 116 are shown. In one implementation, the sprocket 308 includes a channel 340 defined in a first surface 344 extending from a foot end edge 352 to a head end edge 354 to set the maximum extension and flexion angles as described herein.

In one implementation, a second surface 348 disposed generally opposite the first surface 344 includes the opening 324 defined therein. The opening 342 is configured to receive the nut 326 against a wall 366 of a protruding member 364 extends from the first surface 344 to the male spline 338. The wall 366 includes a hole 368 configured to receive the nylon screw 328 to secure the nut 326 to the sprocket 308.

As shown in FIGS. 10A and 10B, the sprocket 308 includes various surfaces that are contoured, angled, planar, and/or the like. In one implementation, the first and second walls 344 and 348 are substantially planar and connected by the faceted surface 310, a foot end surface 362, a head end surface 358, and a rotation surface 356. As shown in FIGS. 10A and 10B, in one implementation, the faceted surface 310 is contoured, angling increasingly towards the rotation surface moving along the faceted surface 310 to the head end surface 358. The faceted surface 310 includes a plurality of facets 360 that are substantially planar surfaces, each configured to match and receive a link 312. For example, in the examples shown in FIGS. 9A-9E, there are four links 312 corresponding to four facets 360. In one implementation, the head end surface 358 is generally planar, the foot end surface 362 is contoured, and the rotation surface 356 is rounded to mirror corresponding surfaces in the cavity 302 of the housing 300.

FIGS. 11A and 11B show the pin 306 with and without the nut 326, respectively. In one implementation, the pin 306 includes an elongated body 370 extending between a first end 372 and a second end 374. To hold the hinge 116 together, the second end 374 of the pin 306 is inserted through the openings 336, 304, 342 and into the opening 346 of the nut 326. The first end 372 engages the head end spar attachment 334, and the second end 374 includes threaded features 376 to engage the nut 326, which is secured to the sprocket 308 with the nylon screw 328 extending through the cutout 350 in the nut 326.

Figure 12B:
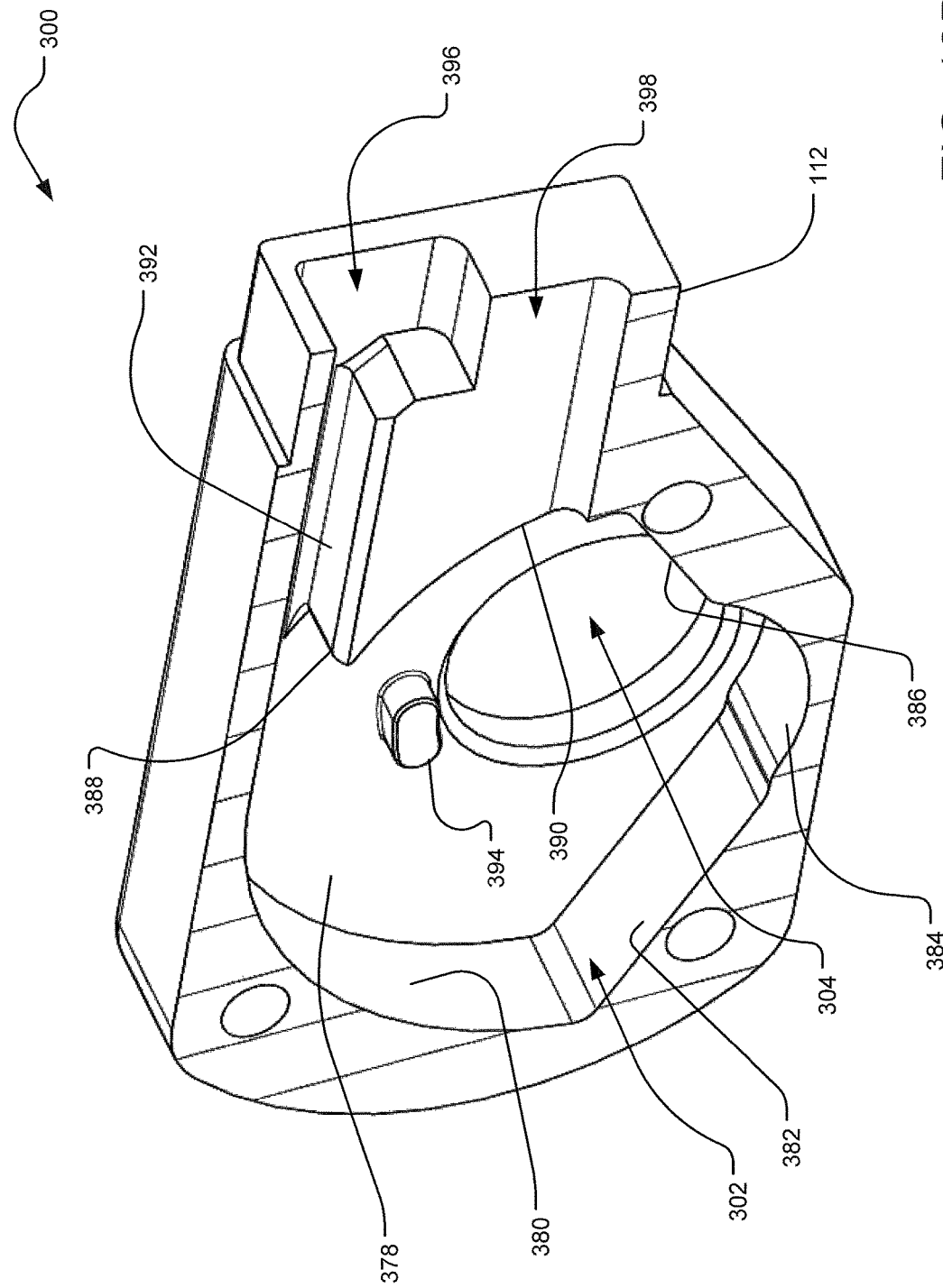
FIG. 12B is longitudinal cross section through the housing of FIG. 12A.

Turning to FIGS. 12A and 12B, which show the housing 300 with the cover 330 removed and a longitudinal cross section through the housing 300 of FIG. 12A, respectively. In one implementation, the housing 300 includes a male connector 395 configured to be received in the lumen 184 to engage the foot end frame 112. The head end spar attachment 334 may have a similar male connector configured to be received in a lumen 182 of the head end frame 114. The male connector 395 includes an opening 396 sides and shaped to permit the drive link 178 to move therethrough along a surface 392 of a protrusion 388. The male connector 395 further includes a channel 398 configured to receive an angled surface 180 of the drive link 178. In one implementation, the surface 392 is generally planar to guide the chain driver as the drive link 178 actuates the sprocket 308 and to maintain the chain link in compression as a failsafe.

In one implementation, the cavity 302 includes various surfaces configured to mirror respective surfaces of the sprocket 308. For example, the surfaces may include a foot end actuation surface 380 and a head end actuation surface 390, which are each configured to mirror the faceted surface 310 alone or in combination with the links 312 depending on the position. The surfaces may further include a foot end surface 386, a rotation surface 384, and a head end surface 382 configured to mirror the foot end surface 362, the rotation surface 356, and the head end surface 358 of the sprocket 308, respectively.

As can be best understood from FIG. 12B, in one implementation, the housing 300 includes a key 394 projecting from the wall 378. When the sprocket 308 is positioned within the cavity 302, the key projects into the channel 340 defined in the first surface 344 of the sprocket 308, such that when the sprocket 308 actuates, the key moves within the channel 340 between the foot end edge 352 to the head end edge 354 to set the maximum flexion and extension angles, respectively.

Figure 13A:
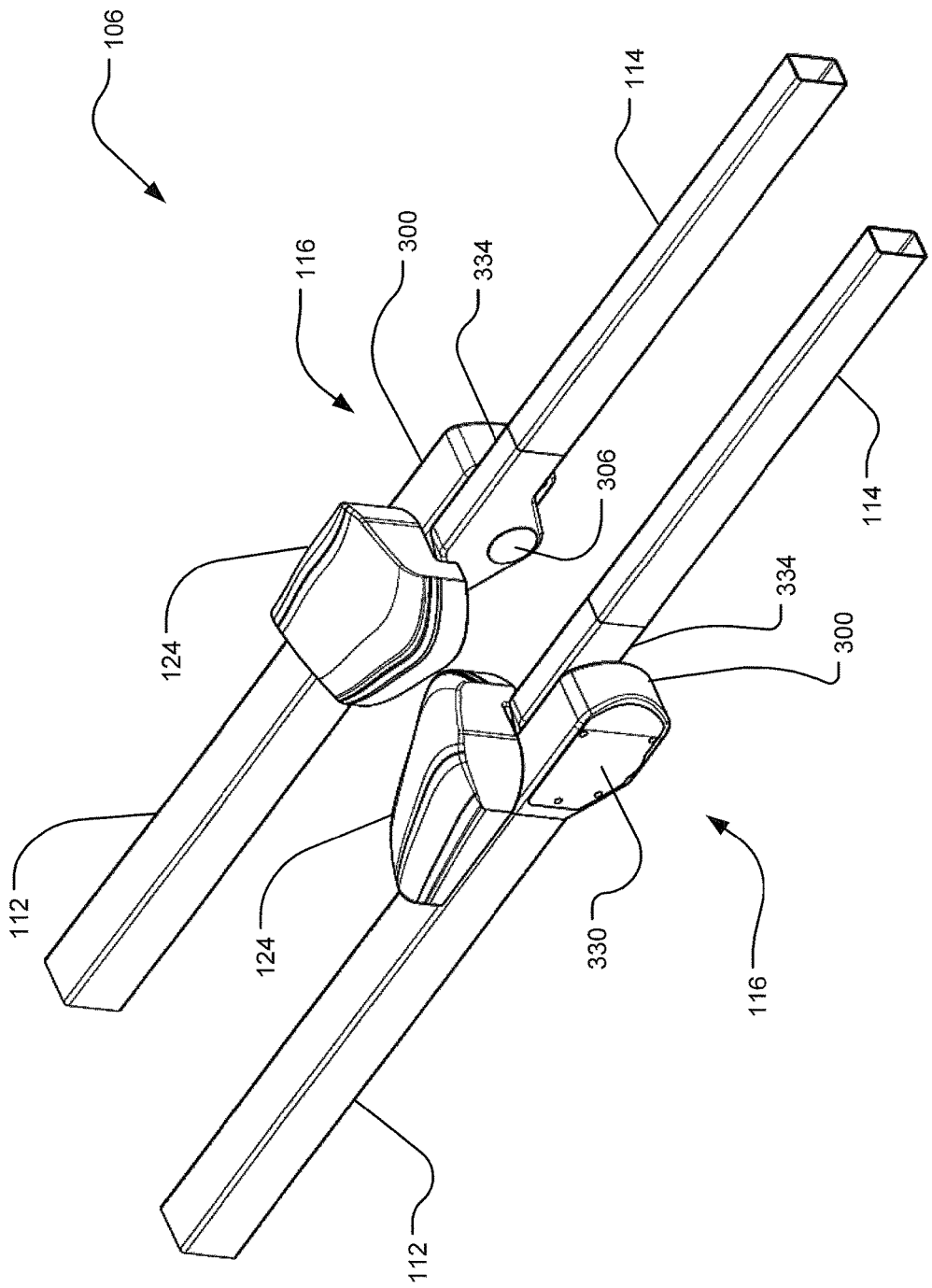
FIG. 13A illustrates a perspective view of a frame of the patient support in the neutral position.
Figure 13B:
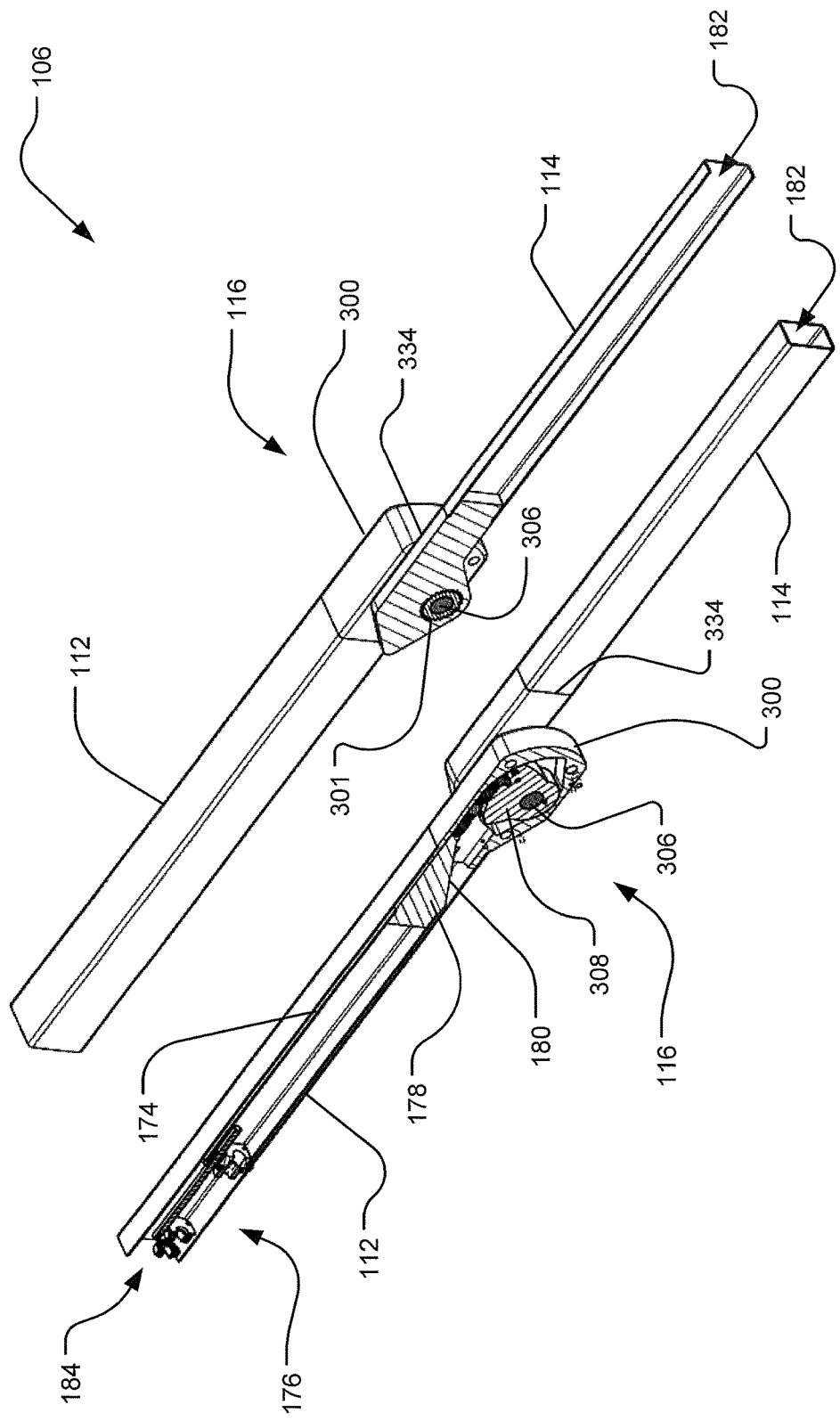
FIG. 13B shows a longitudinal cross section of a right foot end section of the frame and a longitudinal cross section of a left head end section of the frame of FIG. 13A.
Figure 14A:
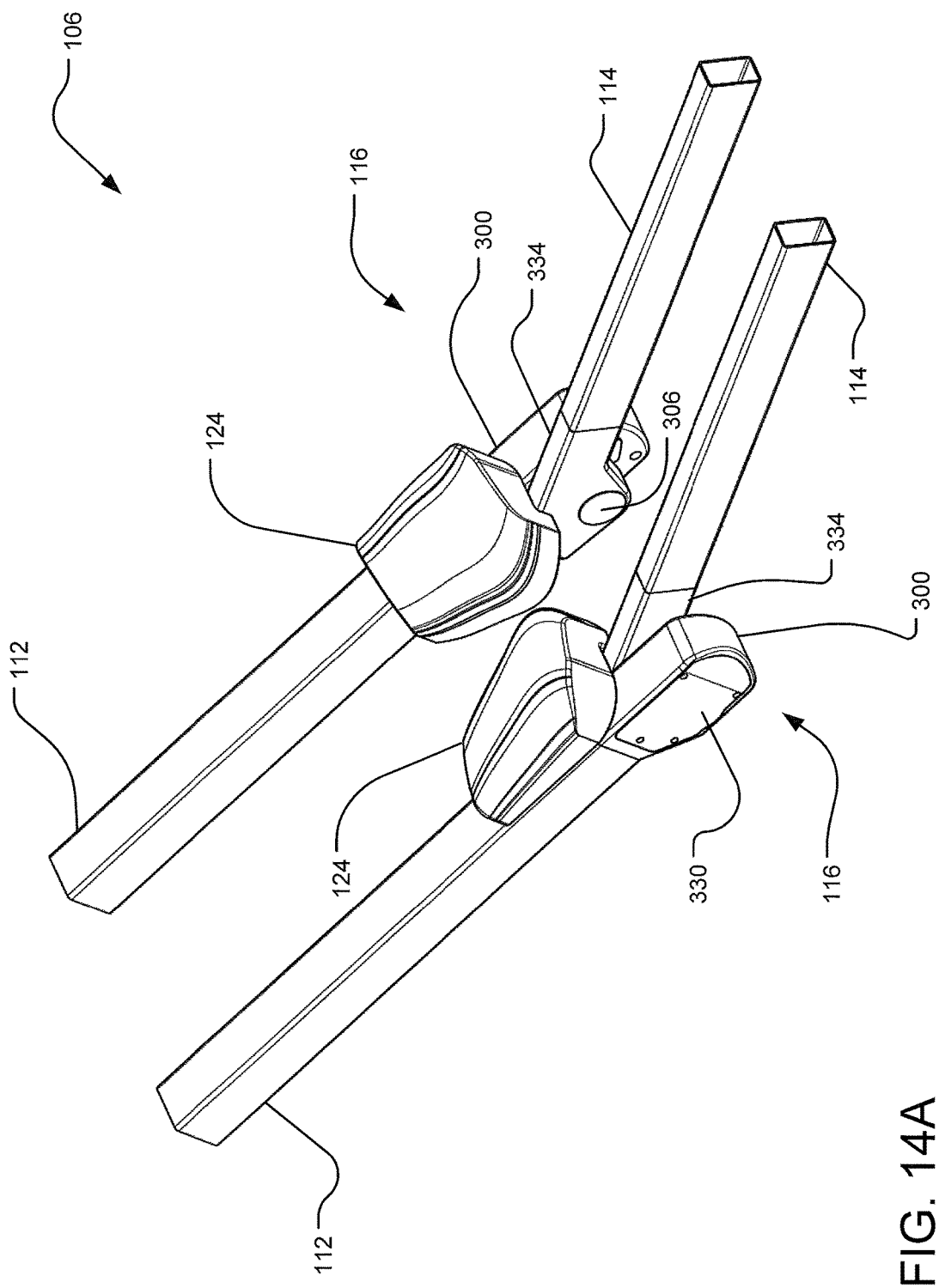
FIG. 14A illustrates a perspective view of a frame of the patient support in the extension position.
Figure 14B:
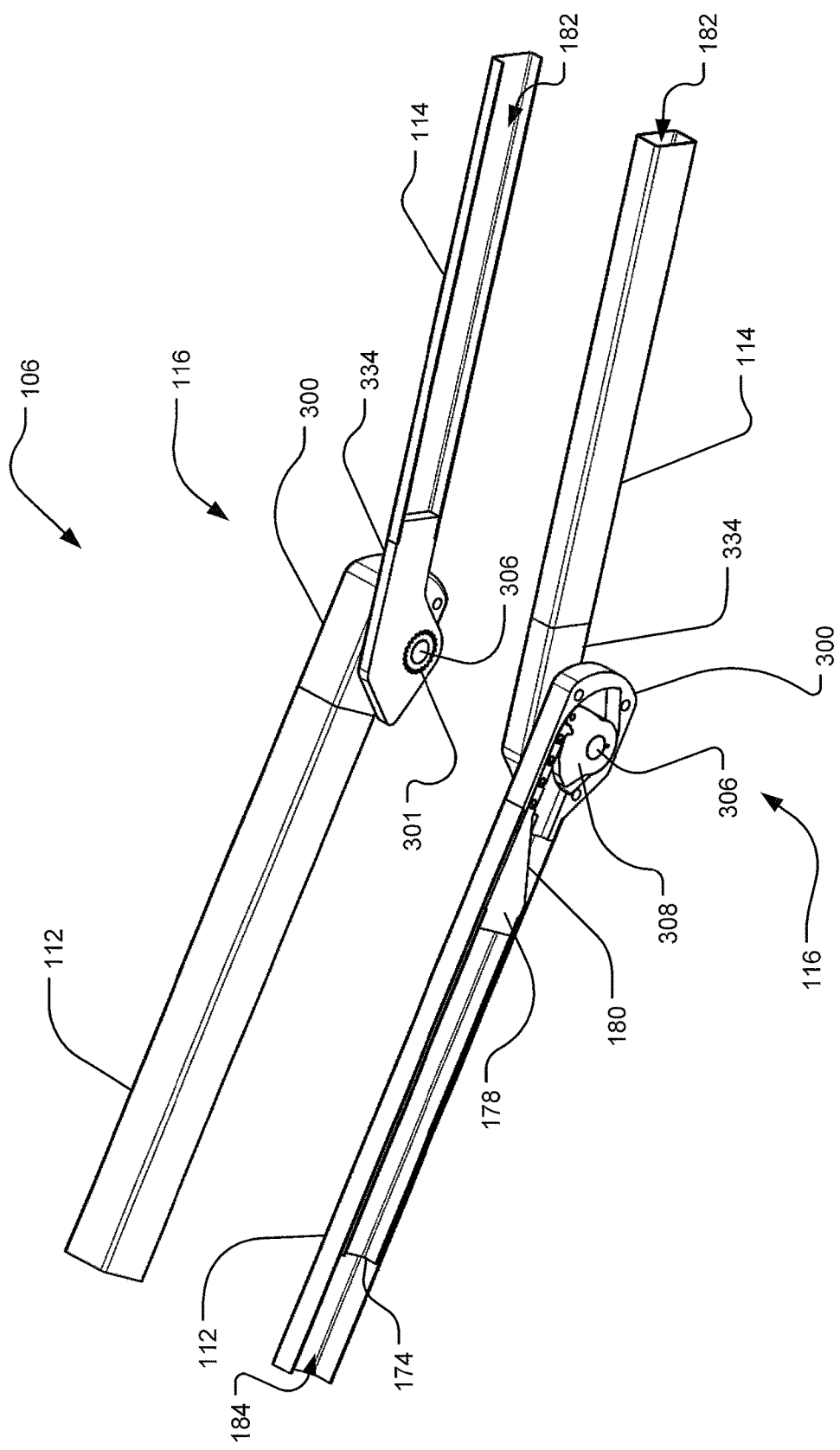
FIG. 14B shows a longitudinal cross section of a right foot end section of the frame and a longitudinal cross section of a left head end section of the frame of FIG. 14A.
Figure 15A:
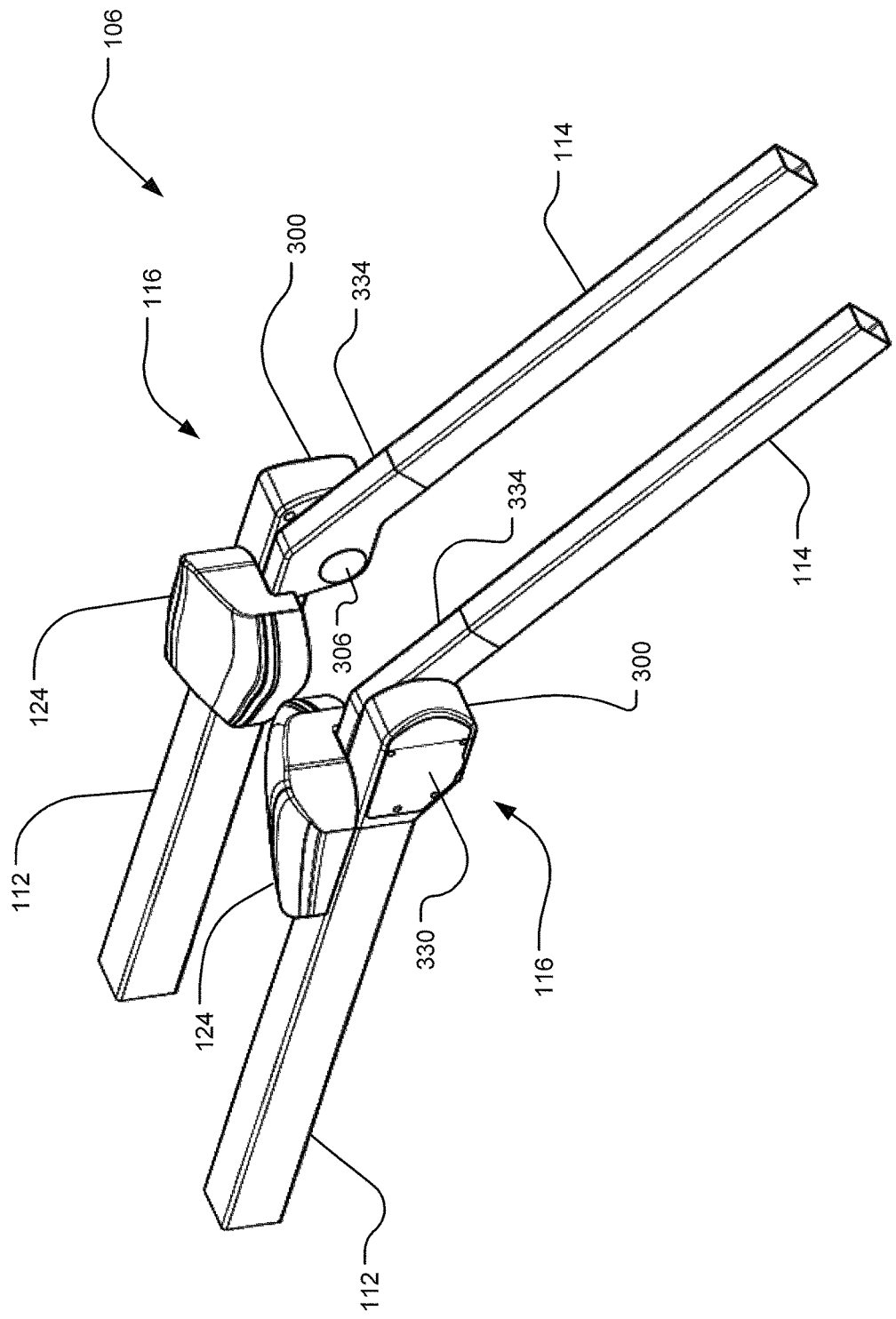
FIG. 15A illustrates a perspective view of a frame of the patient support in the flexion position.
Figure 15B:
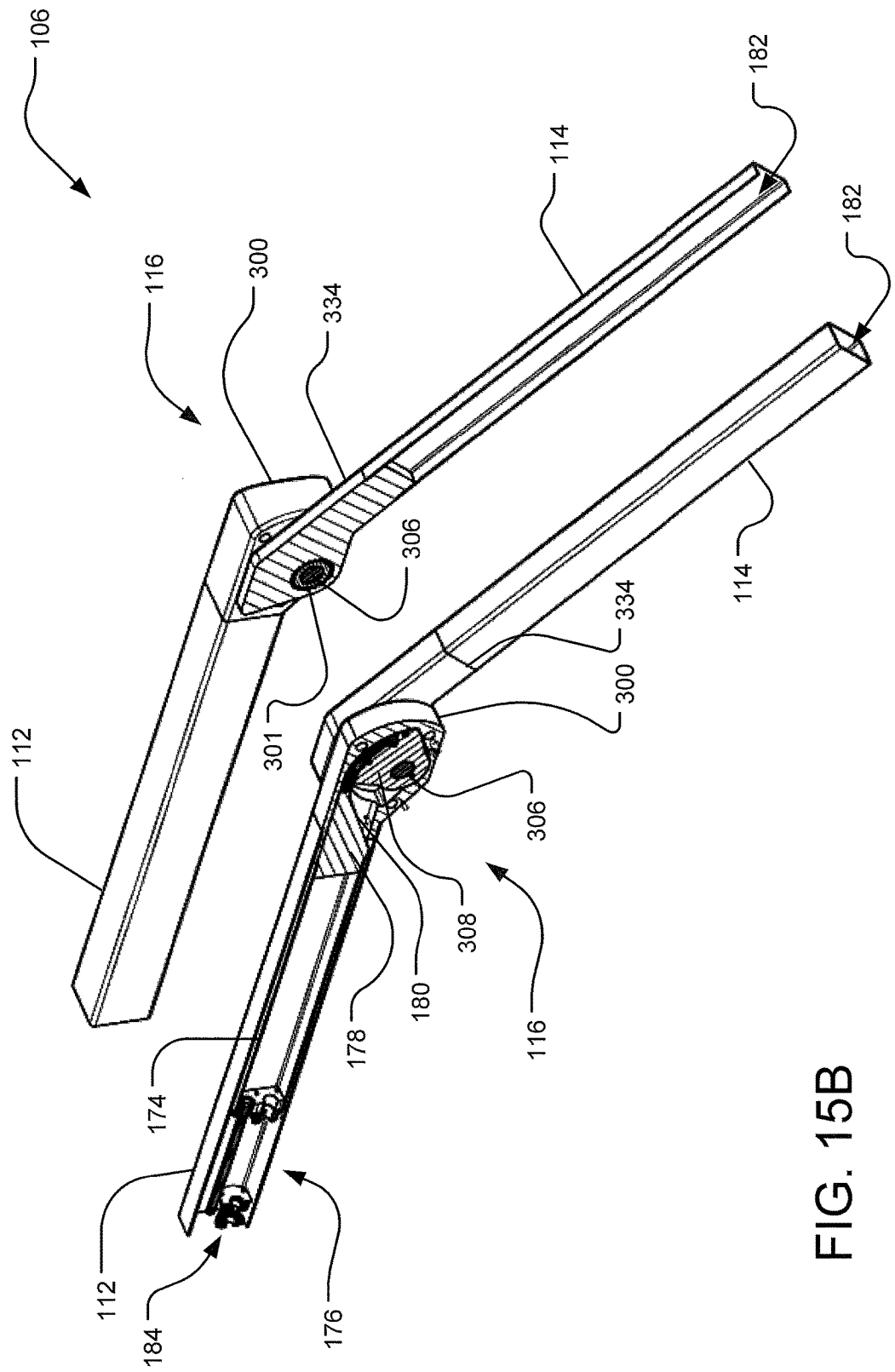
FIG. 15B shows a longitudinal cross section of a right foot end section of the frame and a longitudinal cross section of a left head end section of the frame of FIG. 15A.

Referring to FIGS. 13A-13B, when the sprocket 308 is in the neutral position, the sprocket 308 is oriented generally centrally, such that neither the foot end surface 358 of the sprocket 308 is in contact with the foot end surface 386 of the housing 300 nor the head end surface 362 of the sprocket 308 is in contact with the head end surface 382 of the housing 300. Referring to FIGS. 14A-14B, when the sprocket 308 is actuated to the extension position, the sprocket 308 is oriented towards the foot end 110, such that the foot end surface 358 of the sprocket 308 oriented towards and/or in contact with the foot end surface 386 of the housing 300. As shown in FIGS. 14A-14B, when the sprocket 308 is actuated to the flexion position, the sprocket 308 is oriented towards the head end 108, such that the head end surface 362 of the sprocket 308 oriented towards and/or in contact with the head end surface 382 of the housing 300.

Figure 16E:
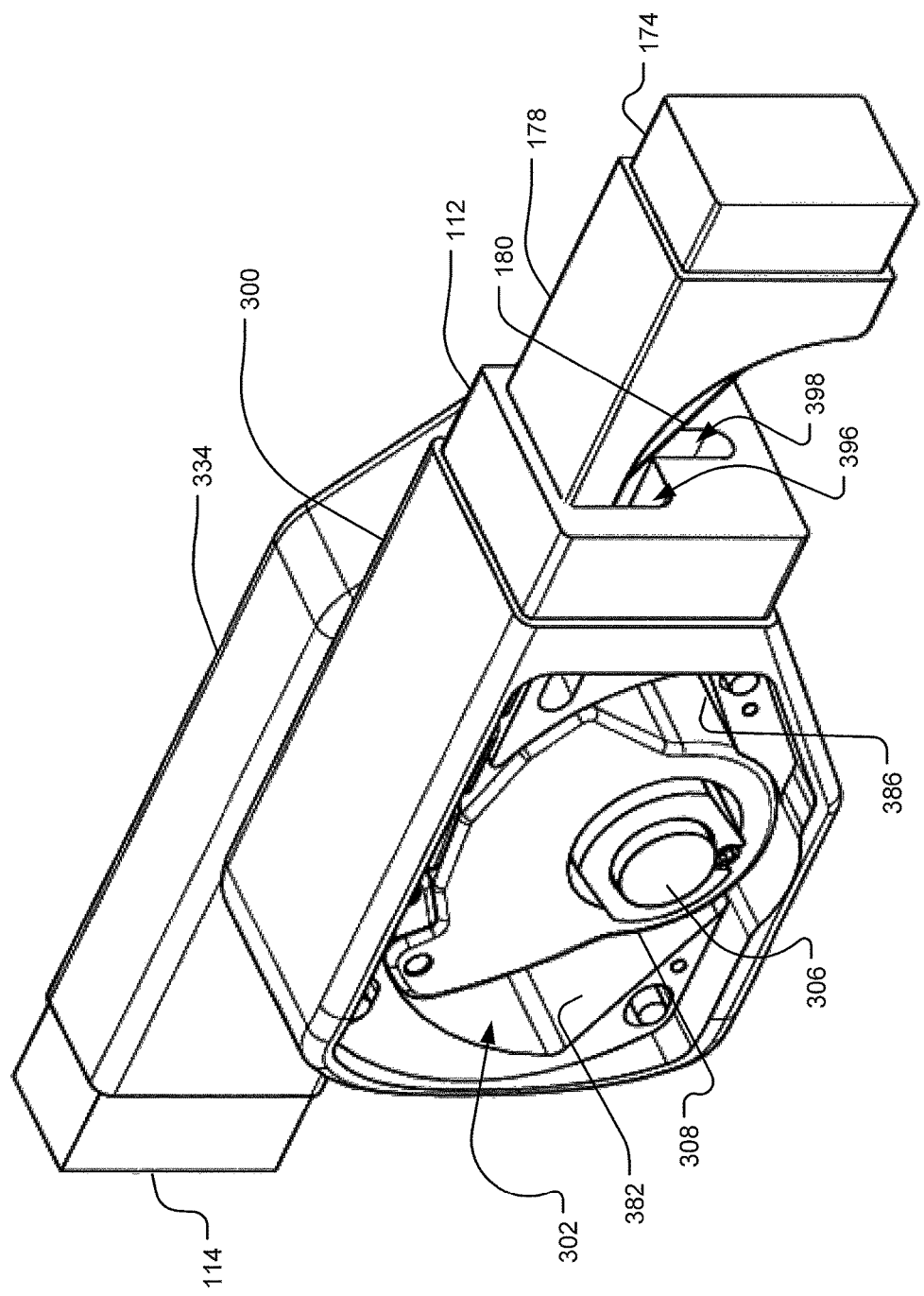
FIG. 16E illustrates a perspective view of the radiolucent hinge in the neutral position with the cover removed.
Figure 16F:
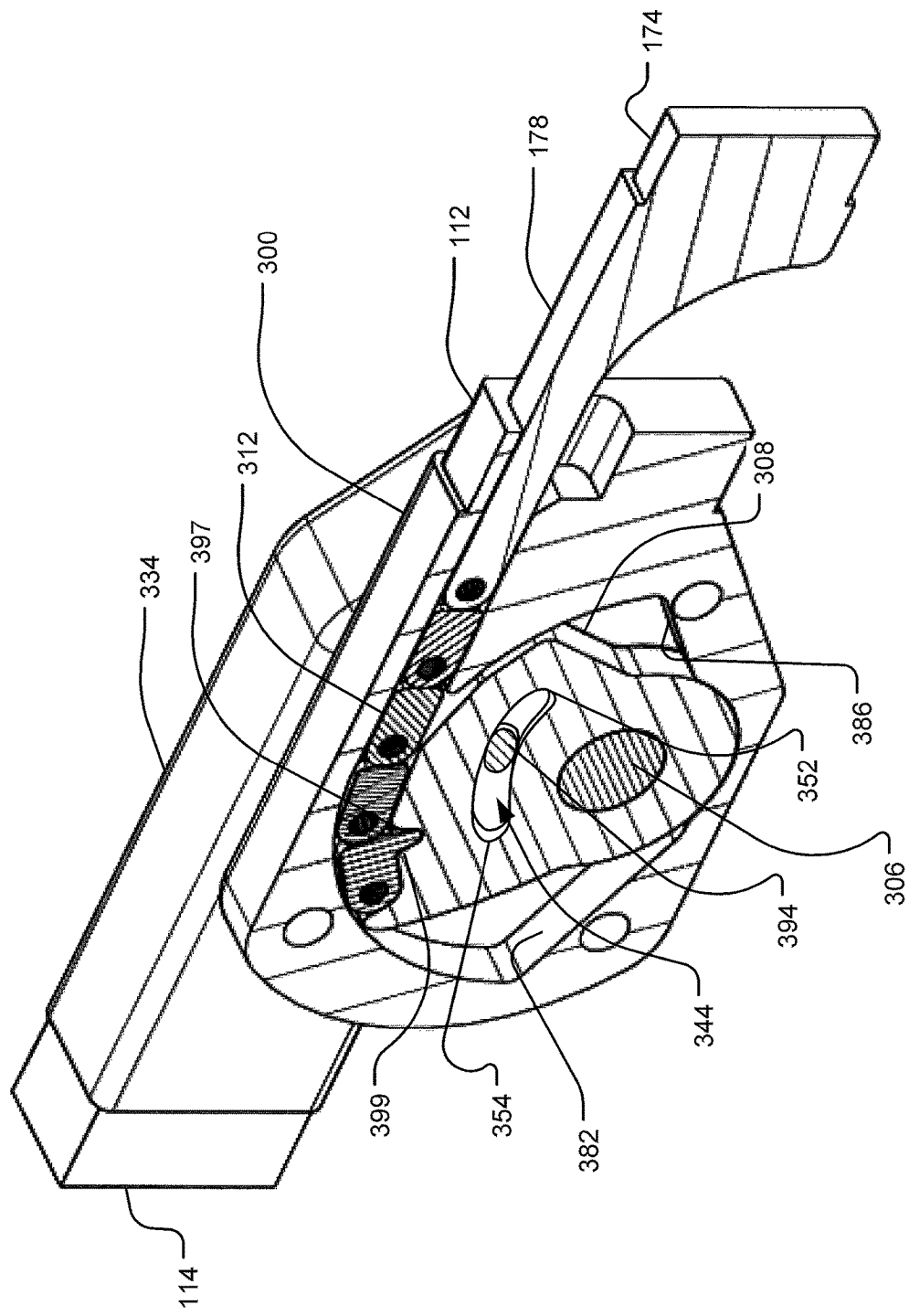
FIG. 16F shows a longitudinal cross section of the radiolucent hinge of FIG. 16E.

For a detailed description of the orientation of the various components of the hinge 116 when in the neutral position, reference is made to FIGS. 16A to 16F. FIG. 16A is a perspective view of right and left hinges 116, shown with the head end spar attachment 334 of the left hinge 116 removed and with the housing 300 of the right hinge 116 removed. FIG. 16B shows the right and left hinges 116 of FIG. 16A with the housing 300 of the left hinge 116 removed. FIG. 16C shows a foot end view of the hinge 116 in the neutral position, and FIG. 16D illustrates a longitudinal cross-section taken along the section line shown in FIG. 16C. FIG. 16E illustrates a perspective view of the hinge 116 in the neutral position with the cover 330 removed. Finally, FIG. 16F shows a longitudinal cross section of the hinge 116 of FIG. 16E.

In one implementation, in the neutral position, the sprocket 308 is oriented generally centrally, such that the chain drive is generally parallel to the drive link 178 and the head end spar attachment 334 and approximately half of the links 312 are in contact with the faceted surface 310. Furthermore, as shown in FIG. 16F, the sprocket 308 is oriented generally centrally, such that the key 394 is positioned in the general center of the channel 340 between the foot end edge 352 and the head end edge 354.

Figure 17E:
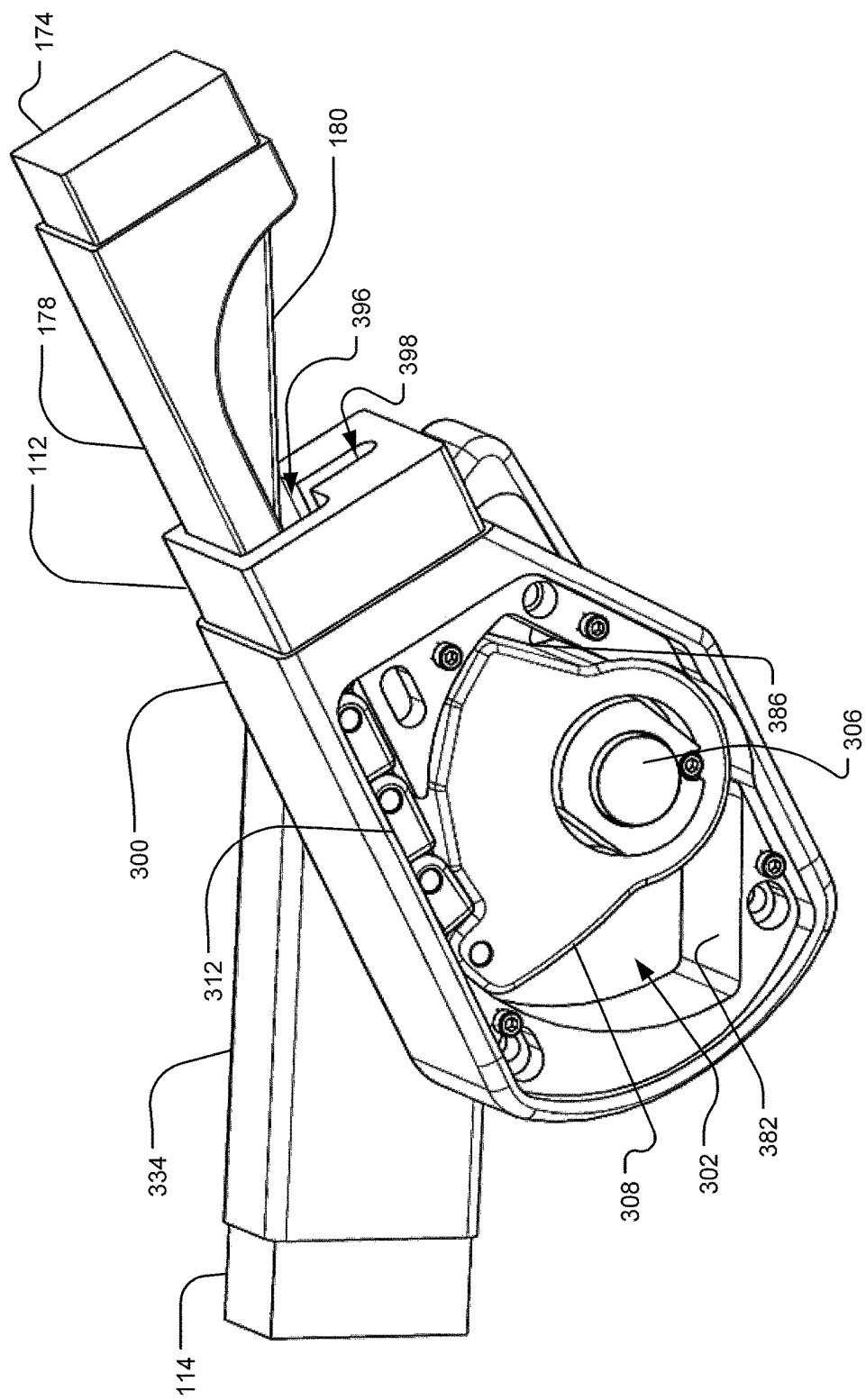
FIG. 17E illustrates a side perspective view of the radiolucent hinge in the extension position with the cover removed.
Figure 17F:
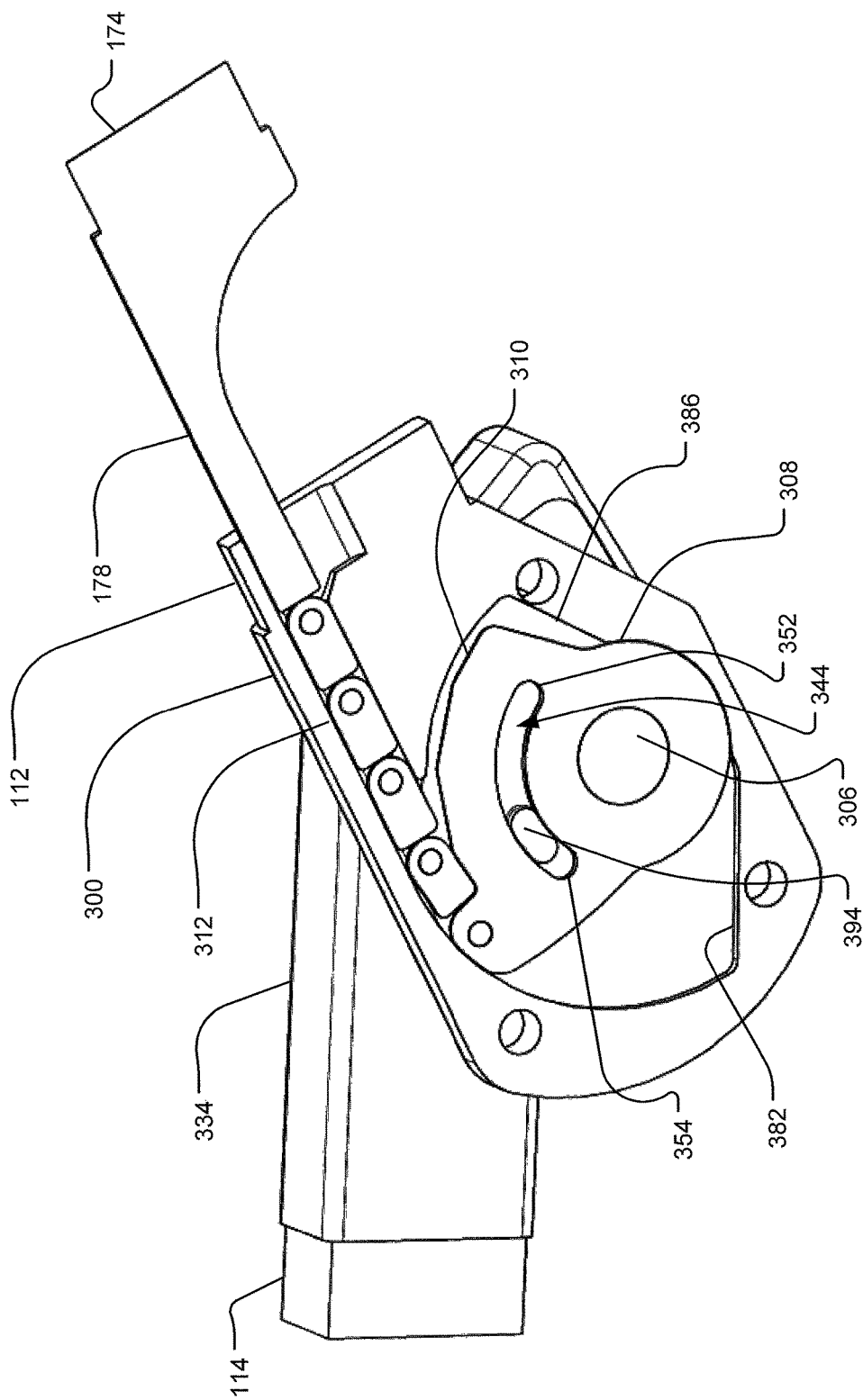
FIG. 17F shows a longitudinal cross section of the radiolucent hinge of FIG. 17E.

For a detailed description of the orientation of the various components of the hinge 116 when articulated to the extension position, reference is made to FIGS. 17A to 17F. FIG. 17A is a perspective view of the right and left hinges 116 in the extension position. FIG. 17B shows the right and left hinges 116 of FIG. 17A shown with the head end spar attachment 334 of the left hinge 116 removed and with the housing 300 of the right hinge 116 removed. FIG. 17C shows a foot end view of the hinge 116 in the extension position, and FIG. 17D illustrates a longitudinal cross-section taken along the section line shown in FIG. 17C. FIG. 17E illustrates a side perspective view of the hinge 116 in the extension position with the cover 330 removed. Finally, FIG. 17F shows a longitudinal cross section of the radiolucent hinge of FIG. 17E.

In one implementation, in the extension position, the sprocket 308 is oriented towards the foot end 110, such that the chain drive is generally parallel to the drive link 178 and at an angle to the head end spar attachment 334. As shown in FIGS. 17A-E, the sprocket 308 is oriented towards the foot end 110, such that only one of the links 312 are in contact with the faceted surface 310, and the remaining links 312 are retracted towards the foot end 110 along the surface 392 of the protrusion 388. In one implementation, the faceted surface 310 of the sprocket 308 includes a recess 397 configured to receive and engage a knob 397 extending from the link 312 attached to the sprocket 308. Furthermore, as shown in FIG. 17F, the sprocket 308 is oriented towards the foot end 110, such that the key 394 is positioned near the head end edge 354 of the channel 340. The key 394 and the head end edge 354 prevent the sprocket 308 from actuating further, thereby setting a maximum extension angle. In one implementation, if the key 394 were to fail, the foot end surface 386 of the housing 300 would prevent the sprocket 308 from further actuating and thereby extending the patient support 106.

Figure 18C:
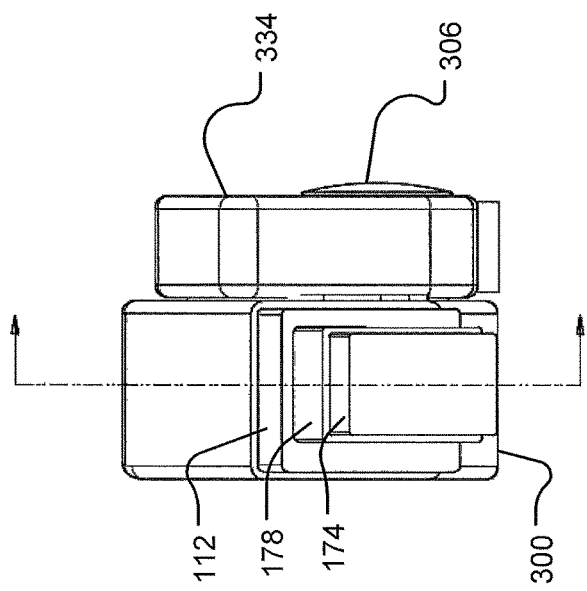
FIG. 18C shows a foot end view of the radiolucent hinge in the flexion position.
Figure 18D:
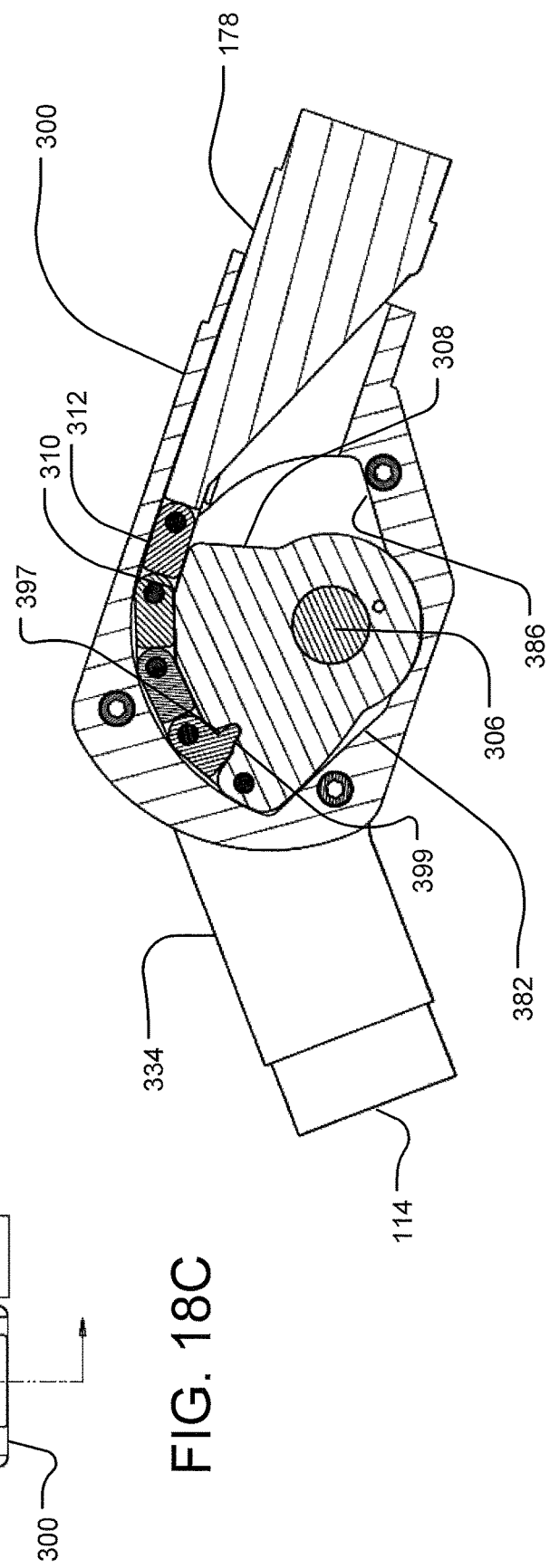
FIG. 18D illustrates a longitudinal cross-section taken along the section line shown in FIG. 18C.
Figure 18E:
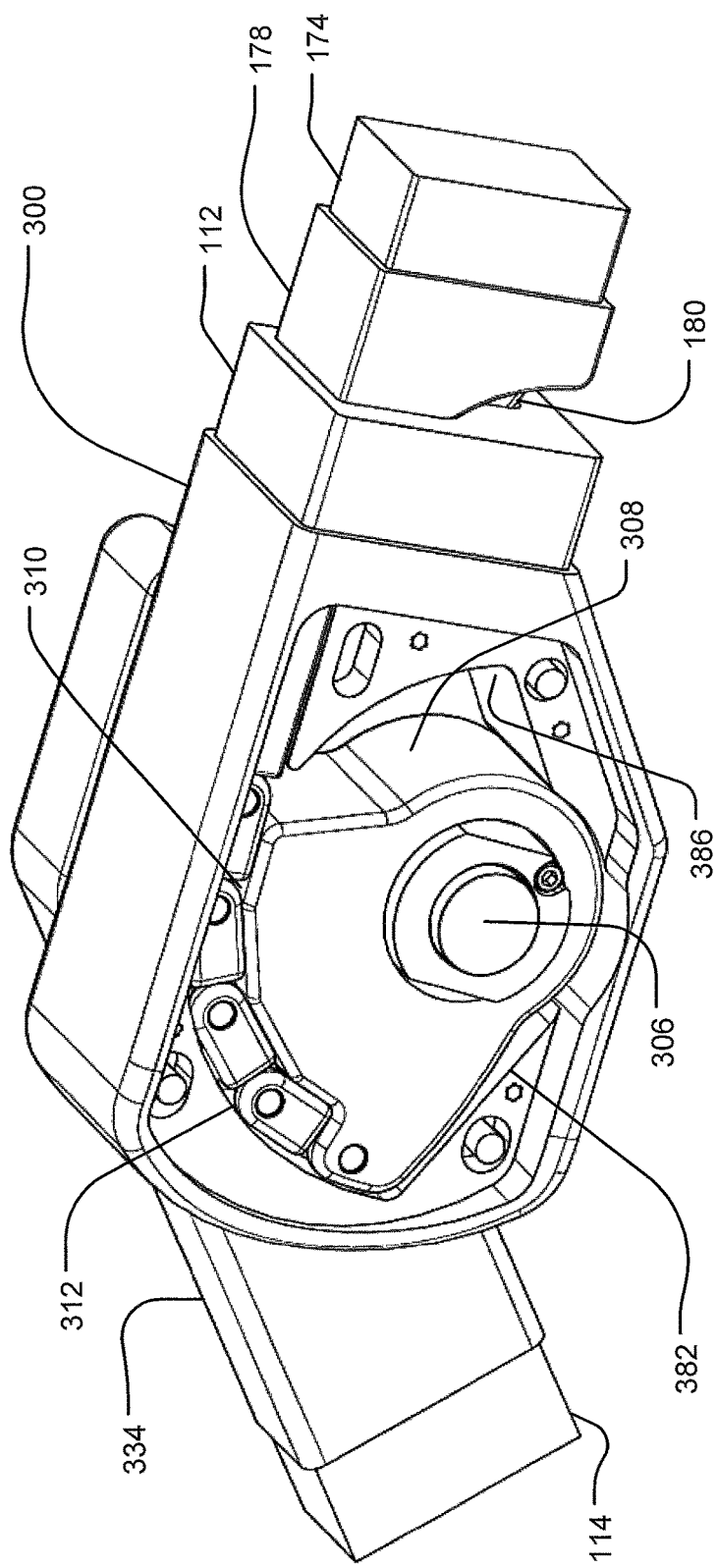
FIG. 18E illustrates a perspective view of the radiolucent hinge in the flexion position with the cover removed.
Figure 18F:
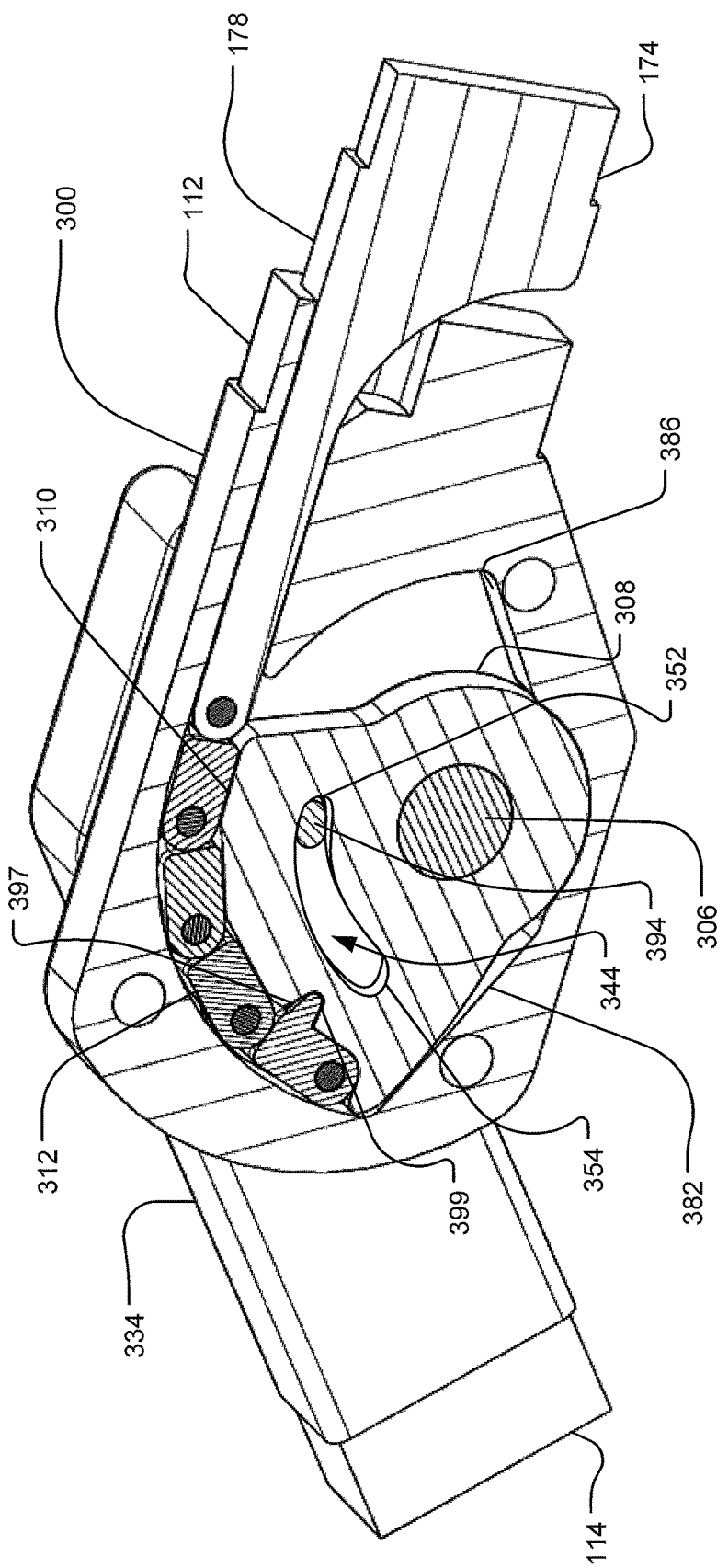
FIG. 18F shows a longitudinal cross section of the radiolucent hinge of FIG. 18E.

For a detailed description of the orientation of the various components of the hinge 116 when articulated to the flexion position, reference is made to FIGS. 18A to 18F. FIG. 18A is a perspective view of right and left hinges 116 shown with the head end spar attachment 334 of the left hinge 116 removed and with the housing 300 of the right hinge 116 removed. FIG. 18B shows the right and left hinges 116 of FIG. 18A with the housing 300 of the left hinge 116 removed. FIG. 18C shows a foot end view of the hinge 116 in the flexion position, and FIG. 18D illustrates a longitudinal cross-section taken along the section line shown in FIG. 18C. FIG. 18E illustrates a perspective view of the hinge 116 in the flexion position with the cover 330 removed. Finally, FIG. 18F shows a longitudinal cross section of the radiolucent hinge of FIG. 18E.

In one implementation, in the flexion position, the sprocket 308 is oriented towards the head end 108, such that the chain drive is wrapped along the faceted surface 310, and the drive link 178 is oriented at an angle to the head end spar attachment 334. As shown in FIGS. 18A-E, the sprocket 308 is oriented towards the head end 108, such that all of the links 312 are in contact with the faceted surface 310, and all the links 312 are extending beyond the surface 392 of the protrusion 388. Furthermore, as shown in FIG. 18F, the sprocket 308 is oriented towards the head end 108, such that the key 394 is positioned near the foot end edge 352 of the channel 340. The key 394 and the foot end edge 352 prevent the sprocket 308 from actuating further, thereby setting a maximum flexion angle. In one implementation, if the key 394 were to fail, the head end surface 382 of the housing 300 would prevent the sprocket 308 from further actuating and thereby flexing the patient support 106.

Figure 19:
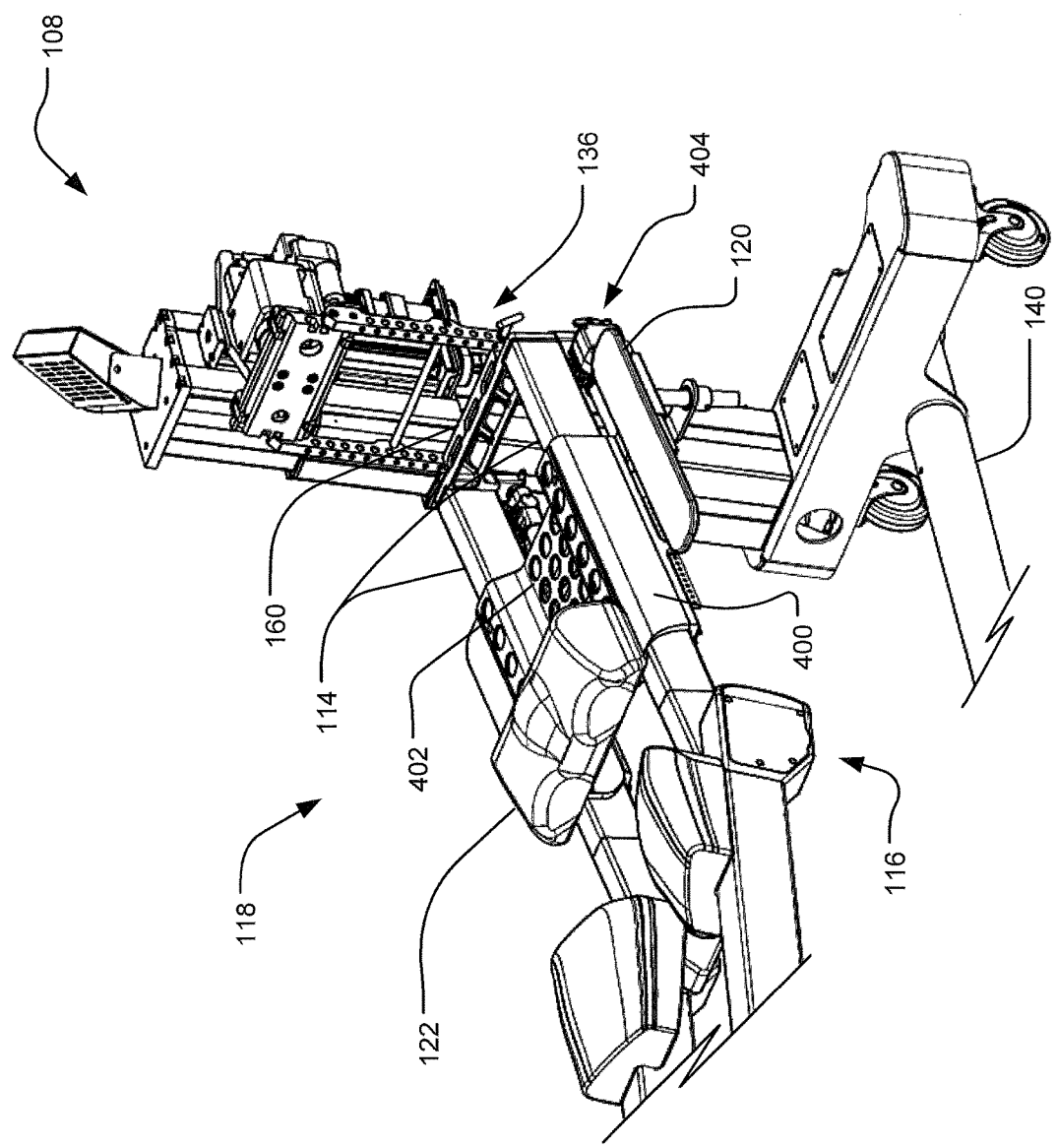
FIG. 19 is a side perspective view of the head end of the surgical table.
Figure 22:
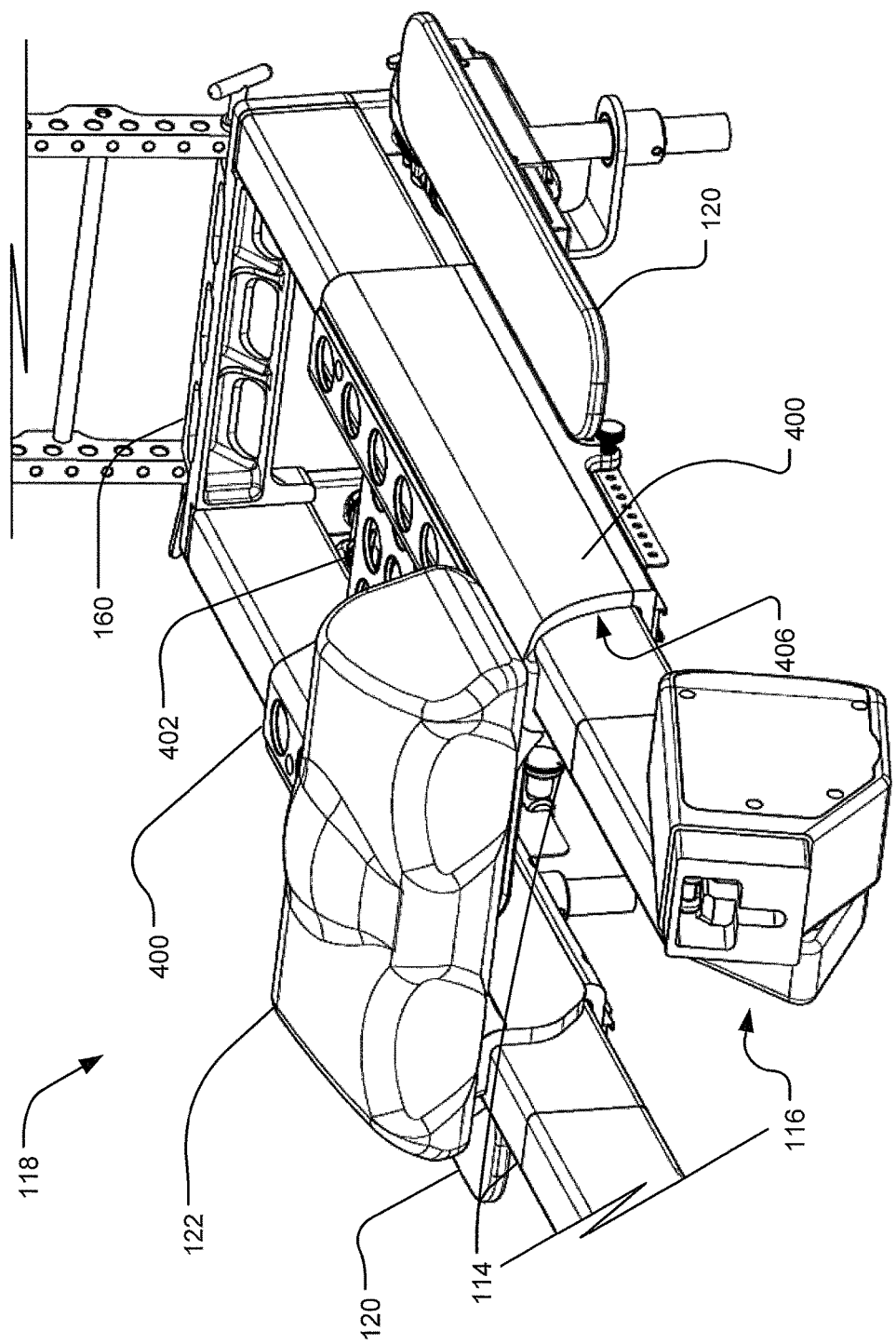
FIG. 22 is a side perspective view of the trunk translator of FIG. 20A.
Figure 23:
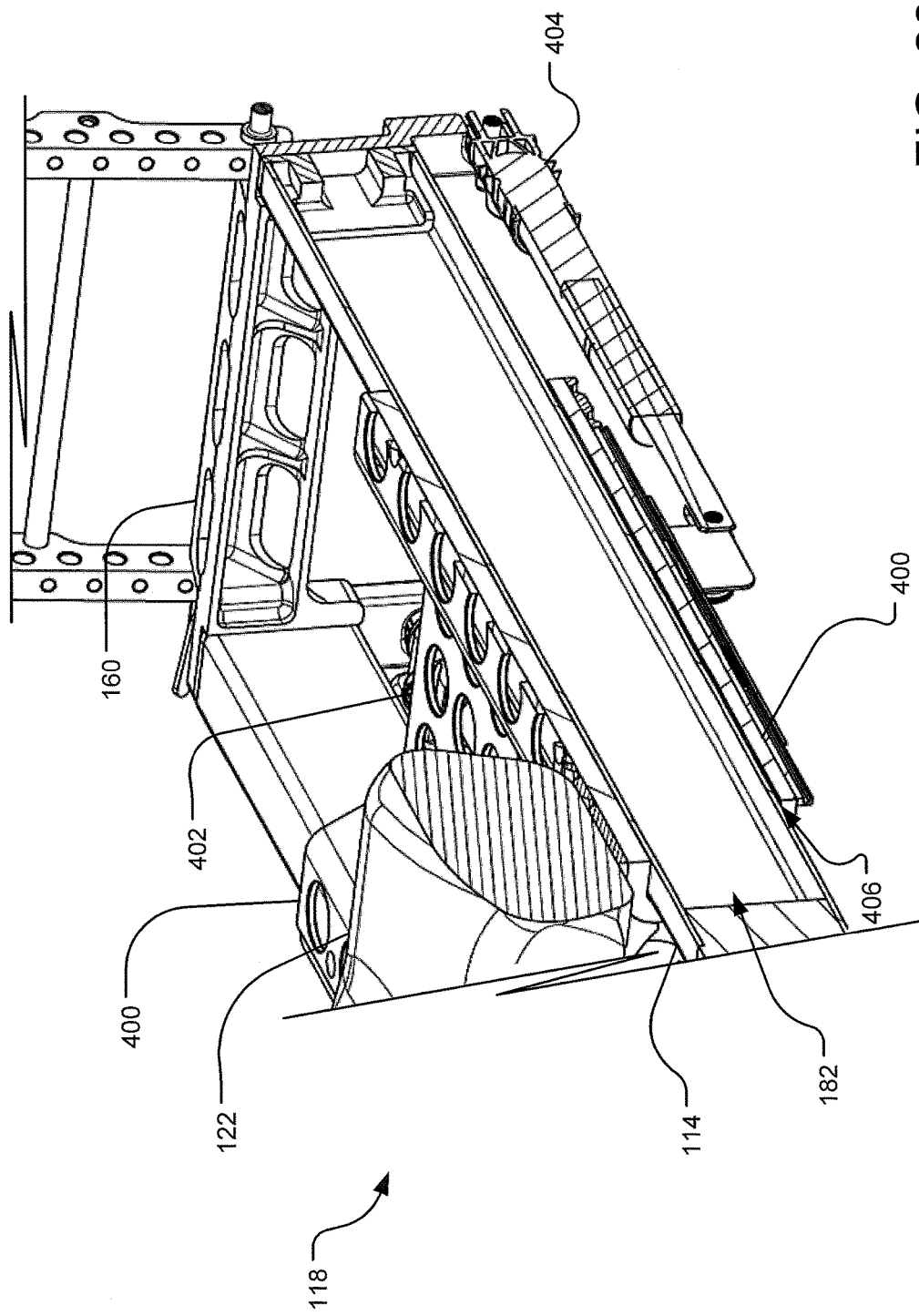
FIG. 23 shows a longitudinal cross section of the trunk translator of FIG. 22.
Figure 24:
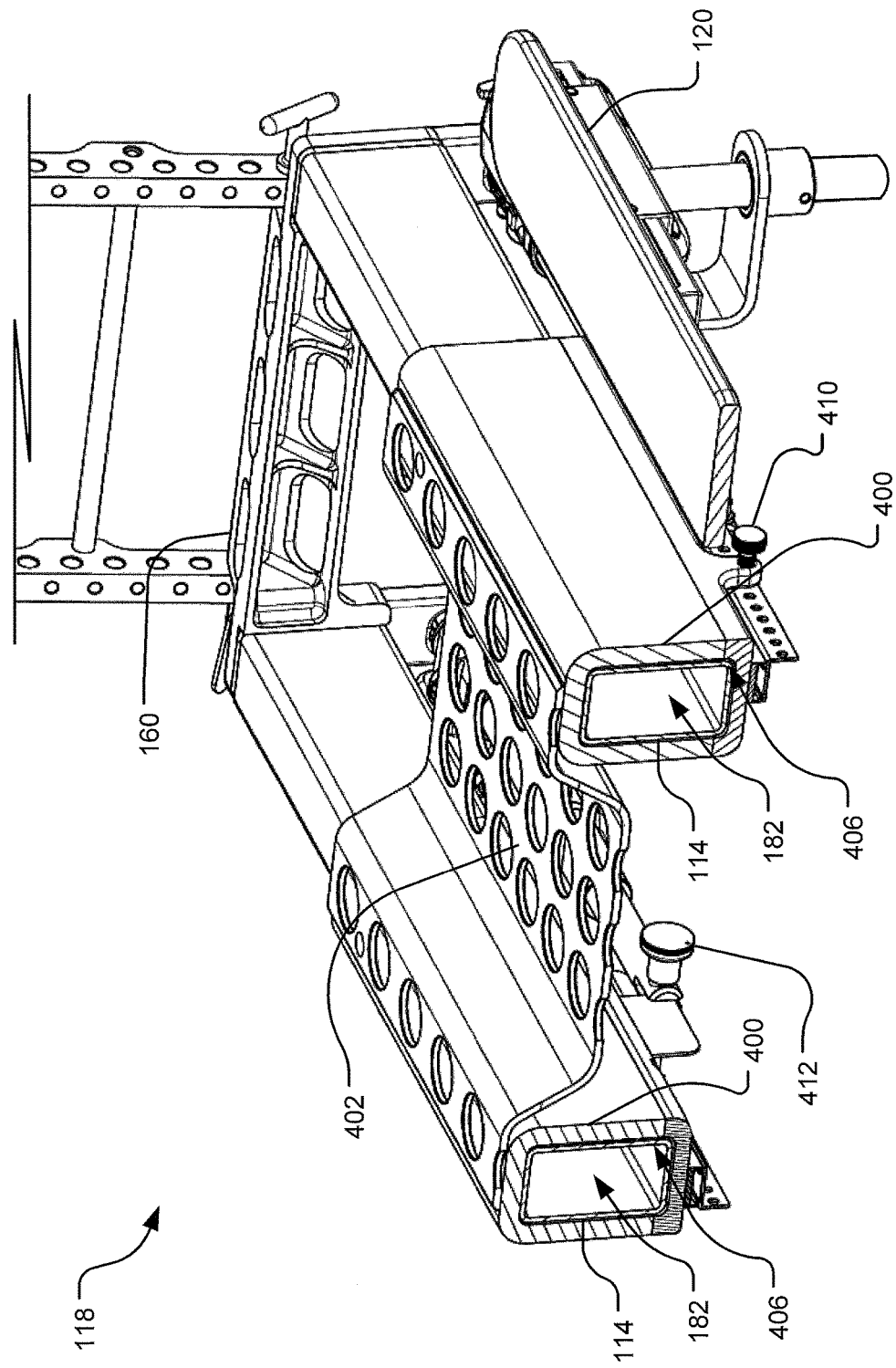
FIG. 24 depicts a horizontal cross section of the trunk translator of FIG. 22.

Turning to FIGS. 19-24, a detailed description of the trunk translator 118 is provided. FIG. 19 is a side perspective view of the head end 108 of the surgical table 100. FIGS. 20A and 20B are respectively a top and a bottom perspective view of the trunk translator 118 and the head end roll assembly 136 mounted to the head end frame 114 of the patient support 106. FIGS. 21 and 22 are a detailed bottom perspective view and a side perspective view, respectively, of the trunk translator 118. FIG. 23 shows a longitudinal cross section of the trunk translator 118 of FIG. 22, and FIG. 24 depicts a horizontal cross section of the trunk translator 118 of FIG. 22.

Figure 20A:
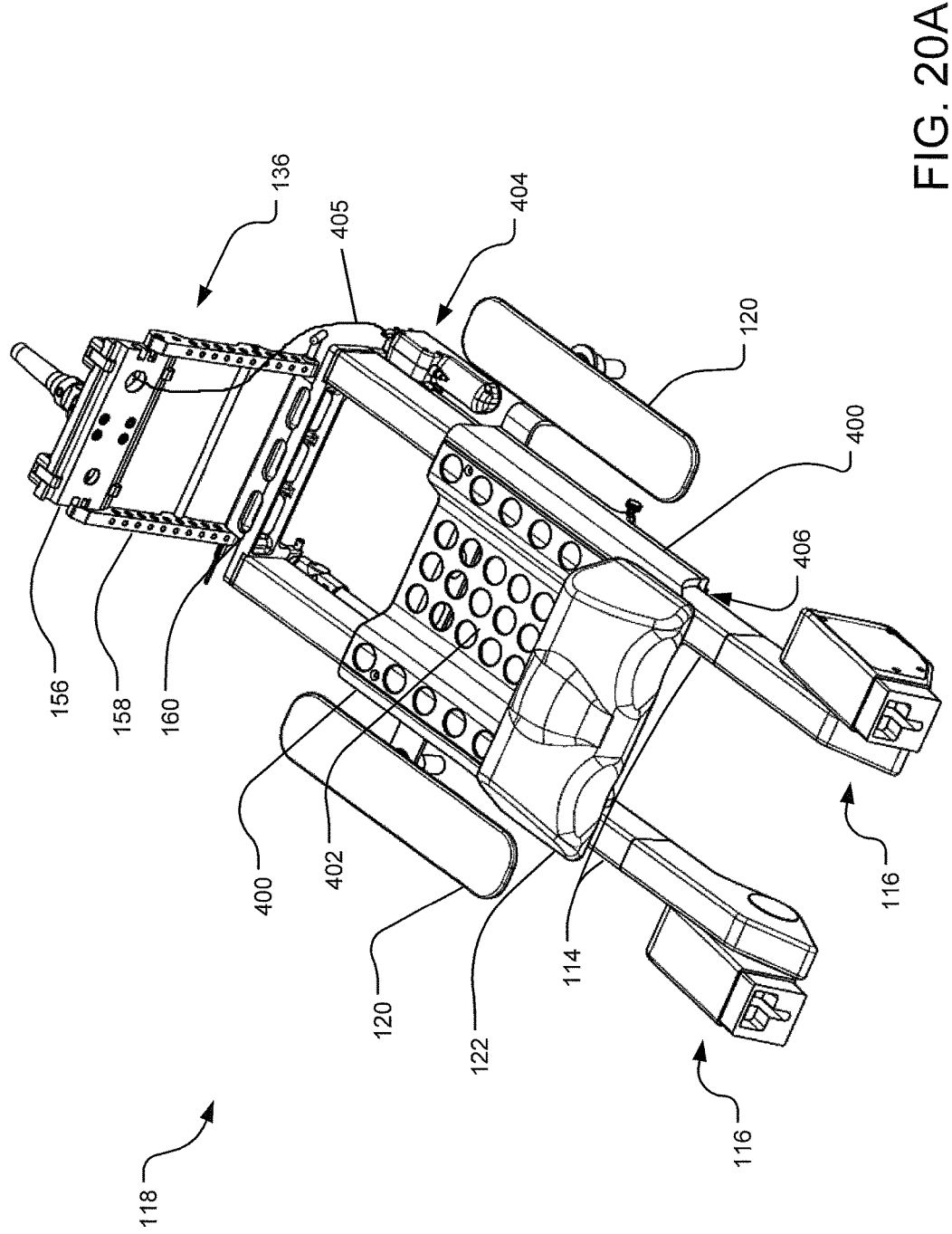
FIGS. 20A and 20B are respectively a top and a bottom perspective view of a trunk translation and roll assembly mounted on the head end frame of the patient support.
Figure 20B:
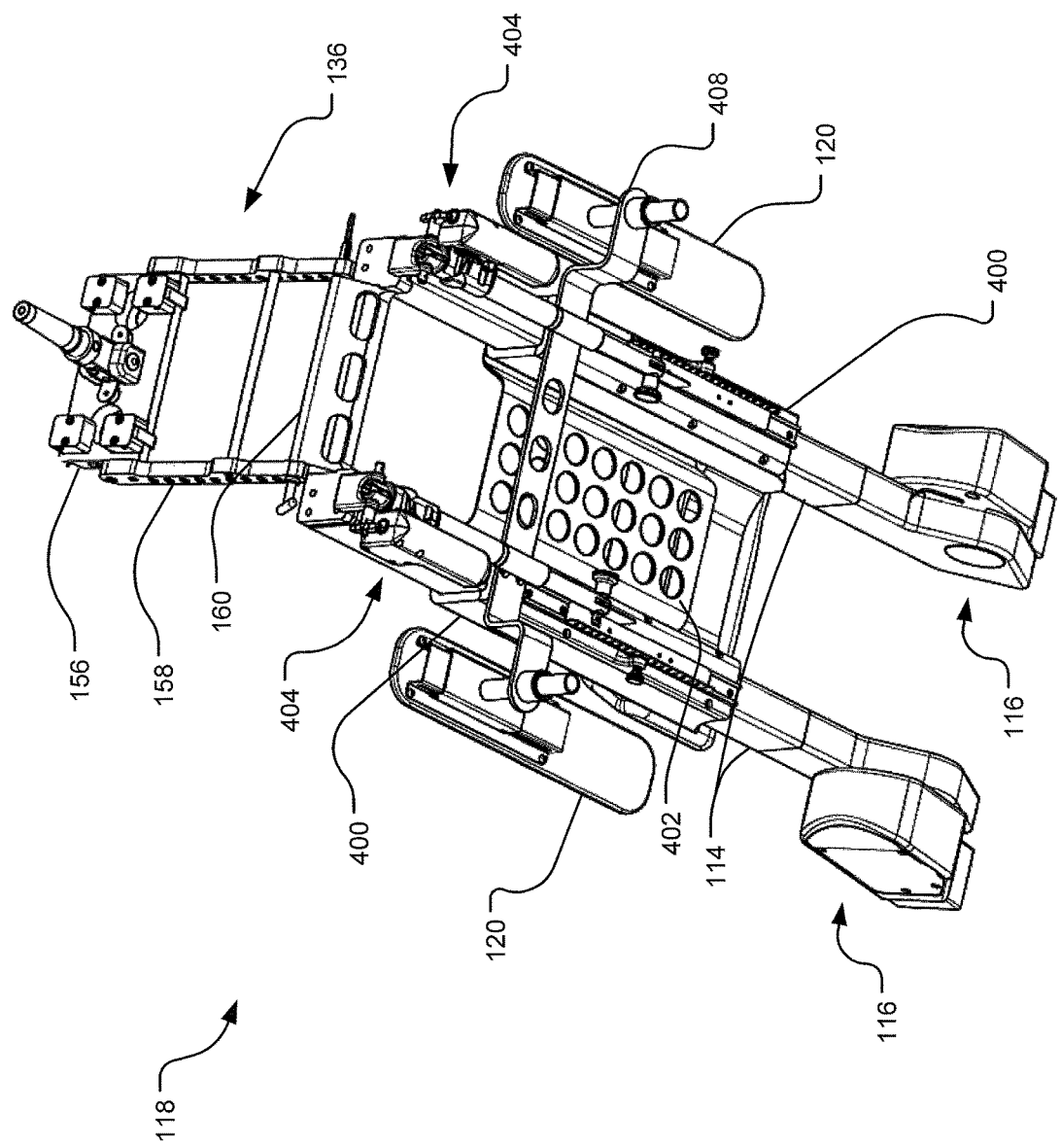

In one implementation, the trunk translator 118 includes arms 400 slidably mounted on the head end frames 114 and connected by a support plate 402 having one or more holes. The arms 400 and/or the support plate 402 are configured to hold and position the chest pad 122, and the arm supports 120 are connected to the arms 400. The arms 400 include a lumen 406 with the head end frames 114 extending therethrough, such that the trunk translator 118 may be moved along the length of the head end frames 114 to compensate for the movement to the various positions described herein to keep the upper body of the patient 102 stationary and prevent compression or stretching of the skin or spine of the patient 102. The movement of the trunk translator 118 is driven by a trunk translator linear actuator 404. A power cord 405 for the linear actuator 404 may be routed up the frame 158, as seen in FIG. 20A, and through a bore in the bracket 156. The power cord 405 may be connected to a "hot plate" for powering the actuator 404. In one implementation, the trunk translator 118 includes a locking pin 410 to lock the trunk translator 118 in place and a quick release pin 412 and handle to release the trunk translator 118.

When the patient 102 is initially positioned on the patient support 106, the trunk translator 118 is set for a torso length of the individual patient 106 and locked with the locking pin 410. Stated differently, the patient 102 is positioned with the pelvis on the hip pads 124, and the trunk translator 118 is moved to position the sternum of the patient 102 on the chest pad 122. The trunk translator 118 is then locked into this position using the locking pin 410. As the table moves to various positions, for example, during flexion and extension articulation, the user device 126 adjusts the position of the trunk translator 118 to keep the distance between the hip pads 124 and the chest pad 122 constant. The constant distance between the pads 122 and 124 prevents distraction and compression of the spine and sheering of the skin of the patient 102 during movement.

Figure 25A:
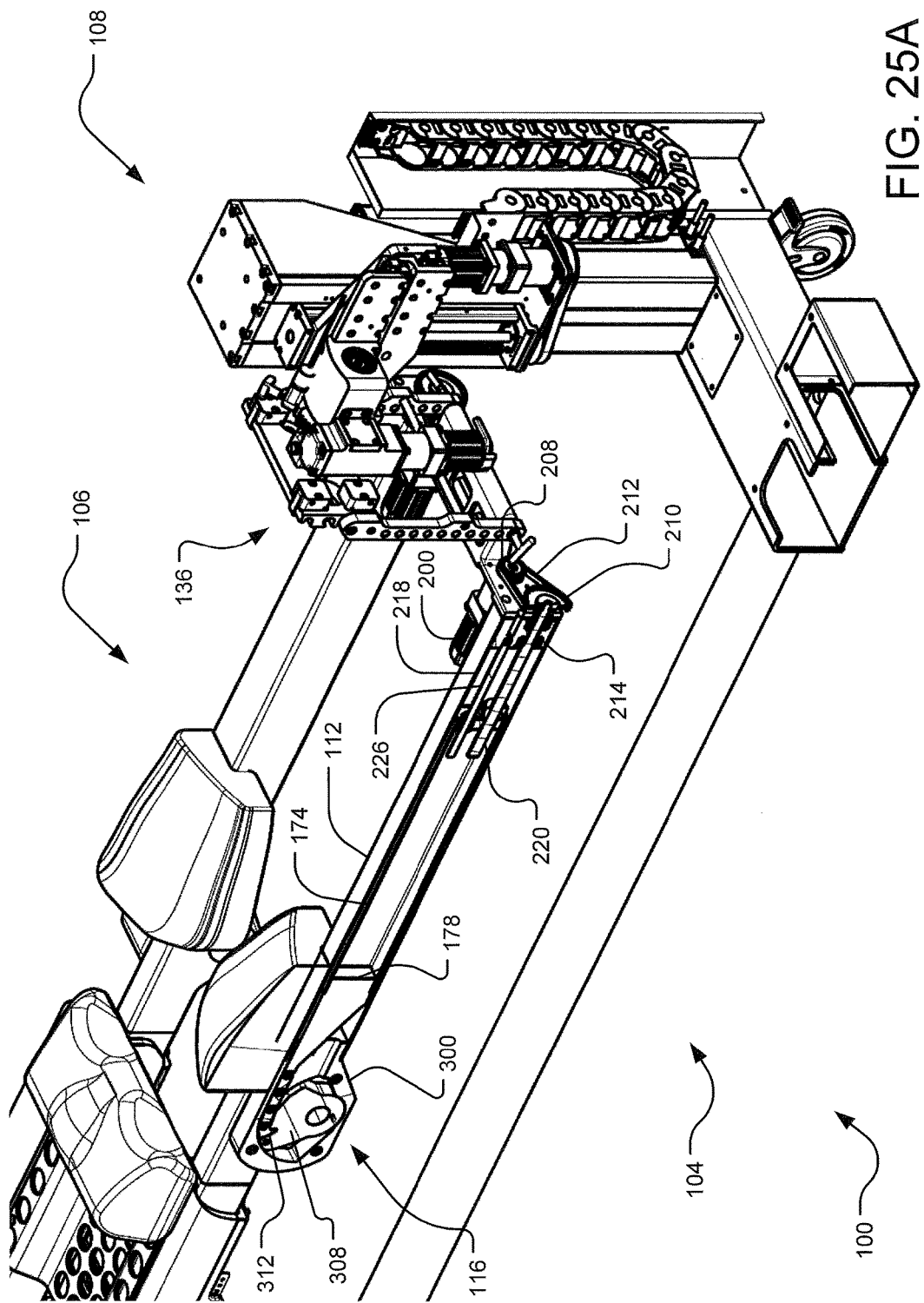
FIG. 25A illustrates foot end perspective view of the surgical table in neutral position with a longitudinal cross section of the right foot end frame.
Figure 25B:
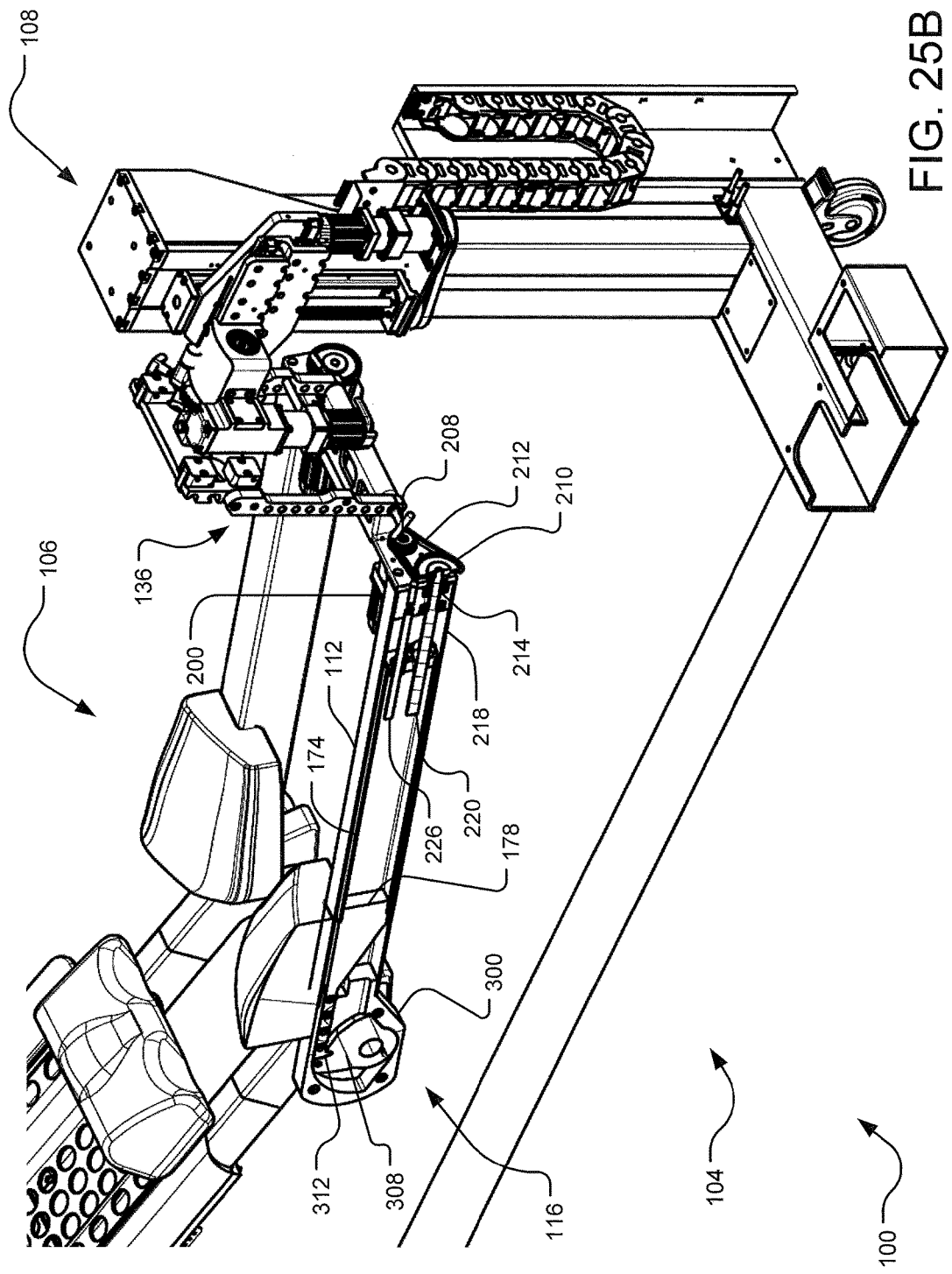
FIG. 25B shows the surgical table of FIG. 25A in the extension position.
Figure 25C:
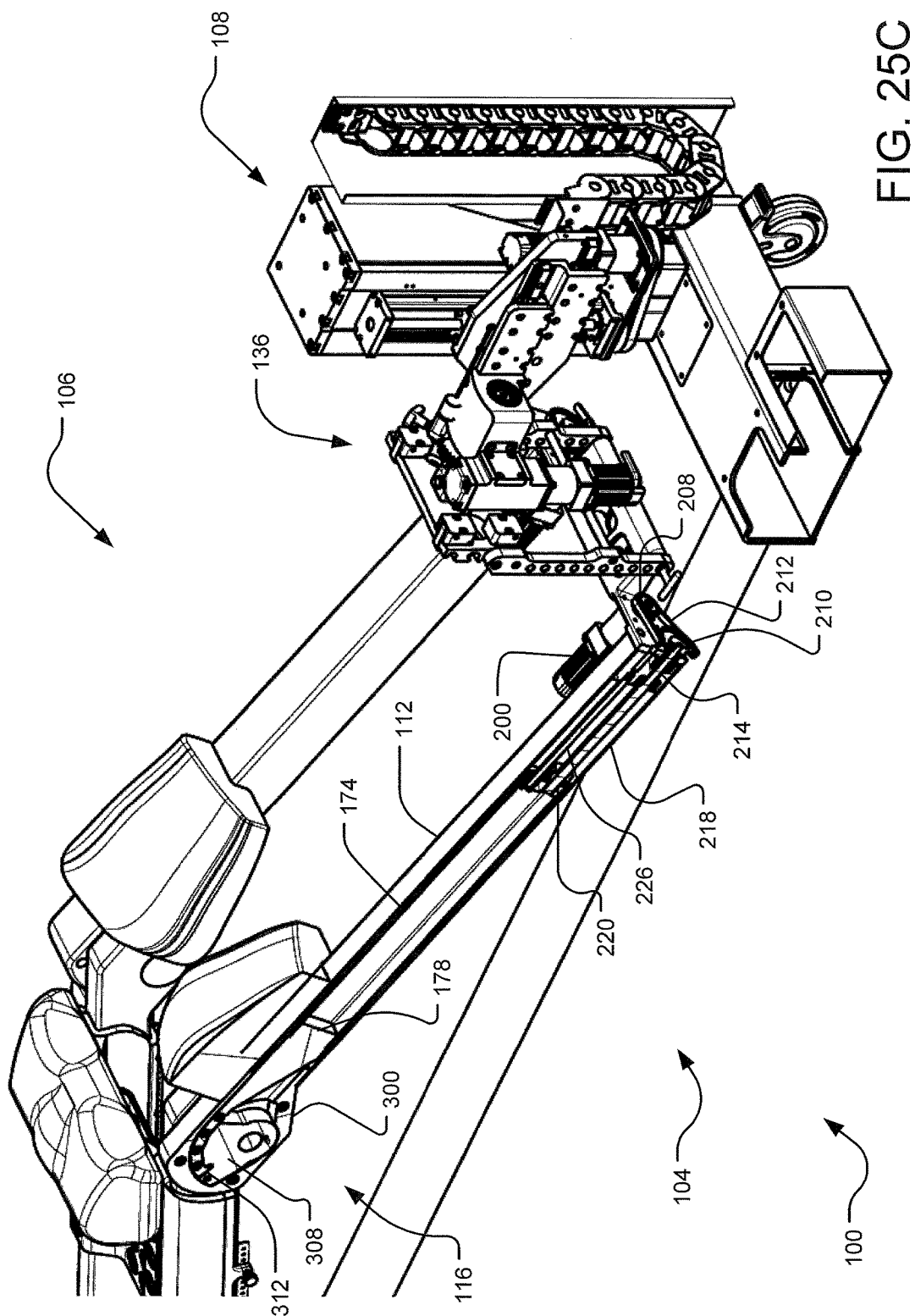
FIG. 25C shows the surgical table of FIG. 25A in the flexion position.

Referring to FIGS. 25A-25C, a foot end perspective view of the surgical table 100 in the neutral position, the extension position, and the flexion position are illustrated, respectively, with a longitudinal cross section of the right foot end frame 112. To move the patient support 106 to the neutral, extension, and flexion positions, the hinges 116 are actuated using the respective driver 176, which drives the a tube 174 extending through the lumen 184 of the foot end frame 112. In one implementation, the drive link 178 extends from the head end of the tube 174, such that when the driver 176 moves the tube 174, the drive link 178 is moved accordingly, thereby actuating the hinge 116.

Turning to FIG. 25A showing the surgical table 100 in the neutral position, in one implementation, the driver 176 actuates the sprocket 308 to orient it generally centrally, such that the chain drive is generally parallel to the drive link 178 and the head end spar attachment 334 and approximately half of the links 312 are in contact with the faceted surface 310.

As can be understood from FIG. 25B, which shows the surgical table 100 in the extension position, in one implementation, the driver 176 actuates the sprocket 308 to orient it towards the foot end 110, such that the chain drive is generally parallel to the drive link 178 and at an angle to the head end spar attachment 334. Further, the sprocket 308 is oriented towards the foot end 110, such that only one of the links 312 is in contact with the faceted surface 310, and the remaining links 312 are retracted towards the foot end 110.

Referring to FIG. 25C, which shows the surgical table 100 in the flexion position, in one implementation, the driver 176 actuates the sprocket 308 to orient it towards the head end 108, such that the chain drive is wrapped along the faceted surface 310, and the drive link 178 is oriented at an angle to the head end spar attachment 334. Further, the sprocket 308 is oriented towards the head end 108, such that all of the links 312 are in contact with the faceted surface 310.

Figure 26:
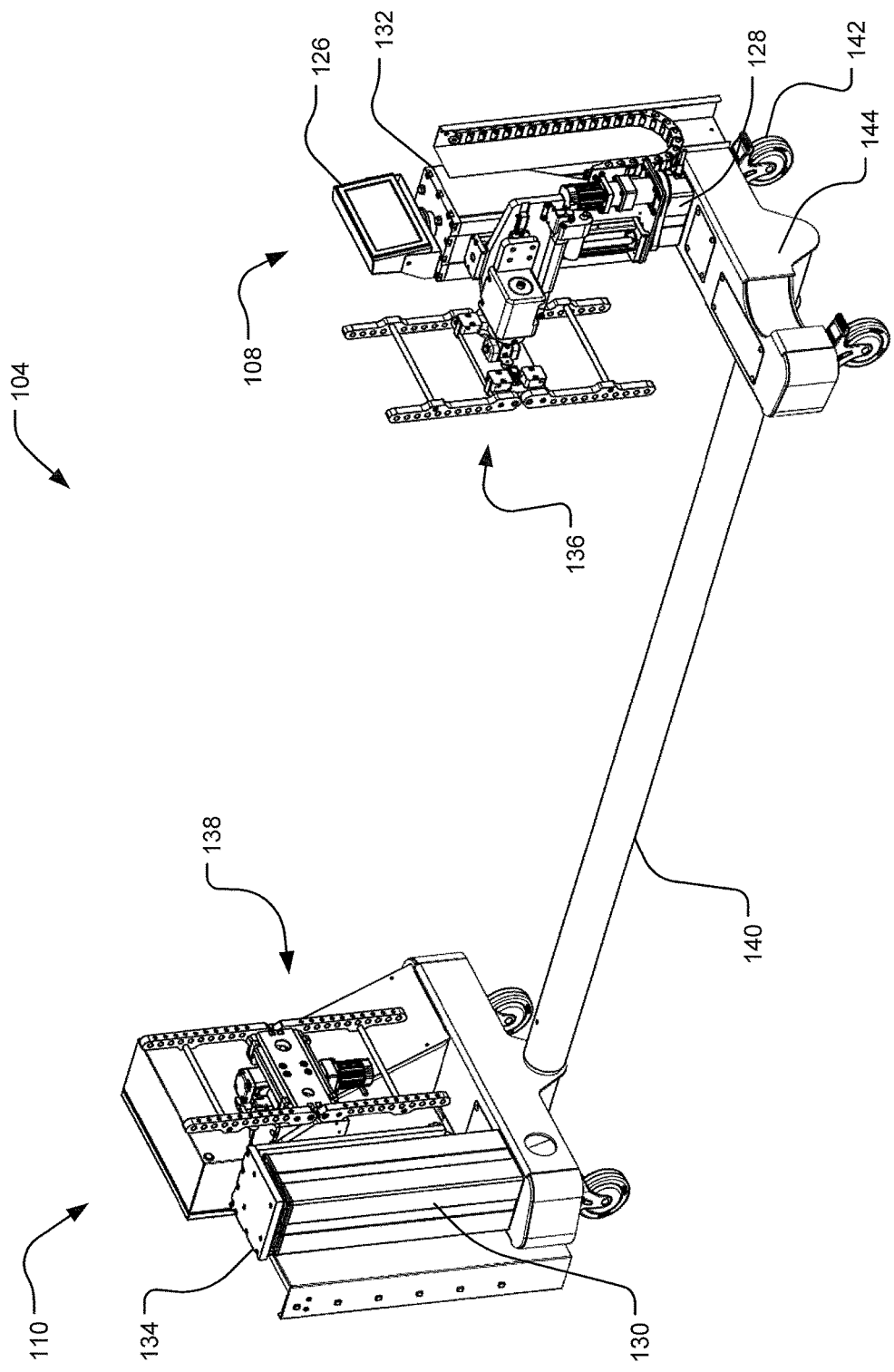
FIG. 26 illustrates an example base of the surgical table.

To begin a detailed description of the base 104, reference is made to FIGS. 26 to 35B. FIG. 26 illustrates an example base of the surgical table. The base may have one or more components substantially similar to the base 104 described with respect to FIGS. 1A-5C and/or the systems and methods described in U.S. patent application Ser. No. 14/012,434, filed on Aug. 28, 2013 and entitled "Patient Positioning Support Apparatus with Virtual Pivot-Shift Pelvic Pads, Upper Body Stabilization and Fail-Safe Attachment Mechanism," which is specifically incorporated by reference in its entirety herein.

Figure 27:
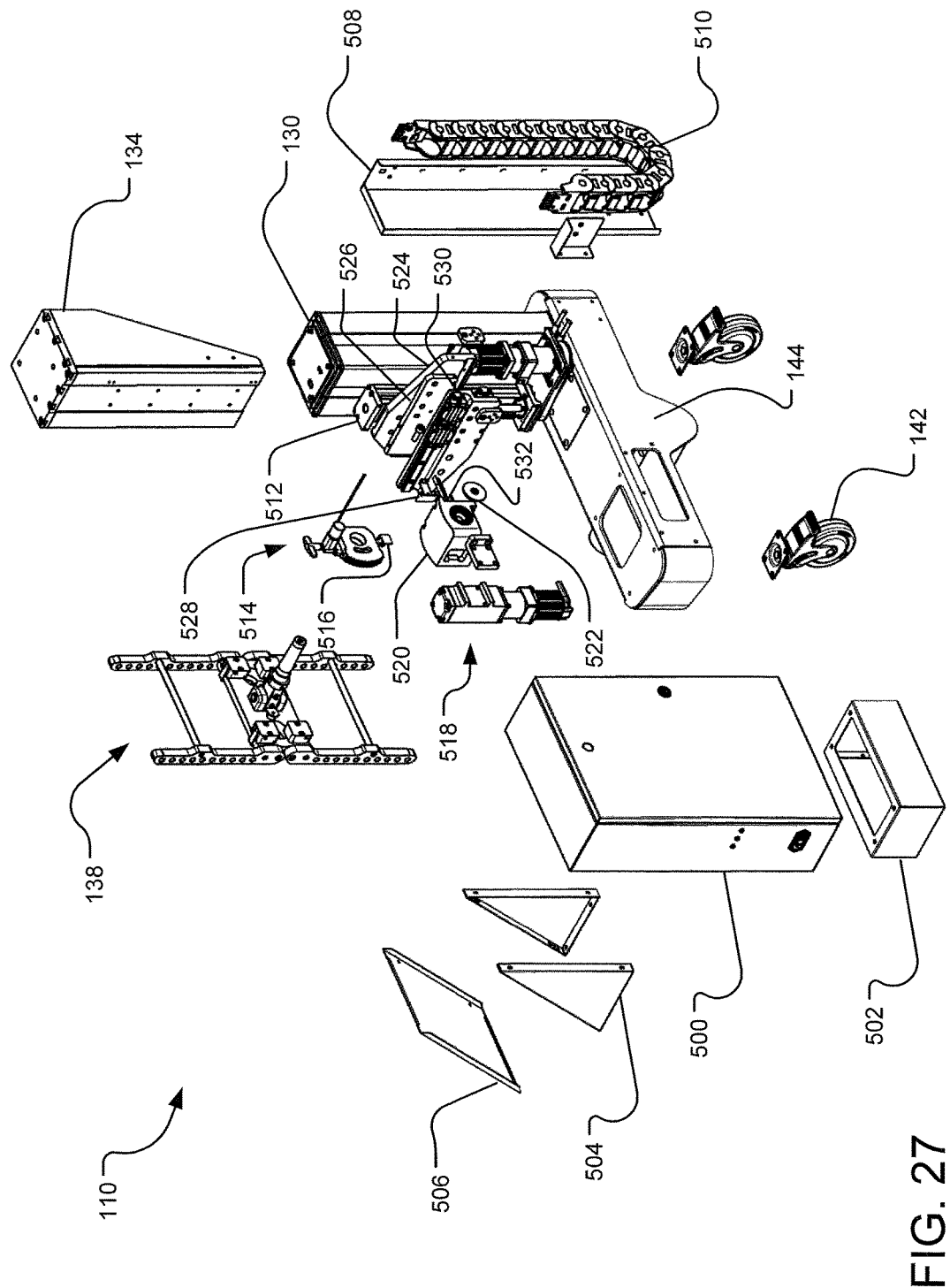
FIG. 27 is an exploded view of the foot end of the base.
Figure 28A:
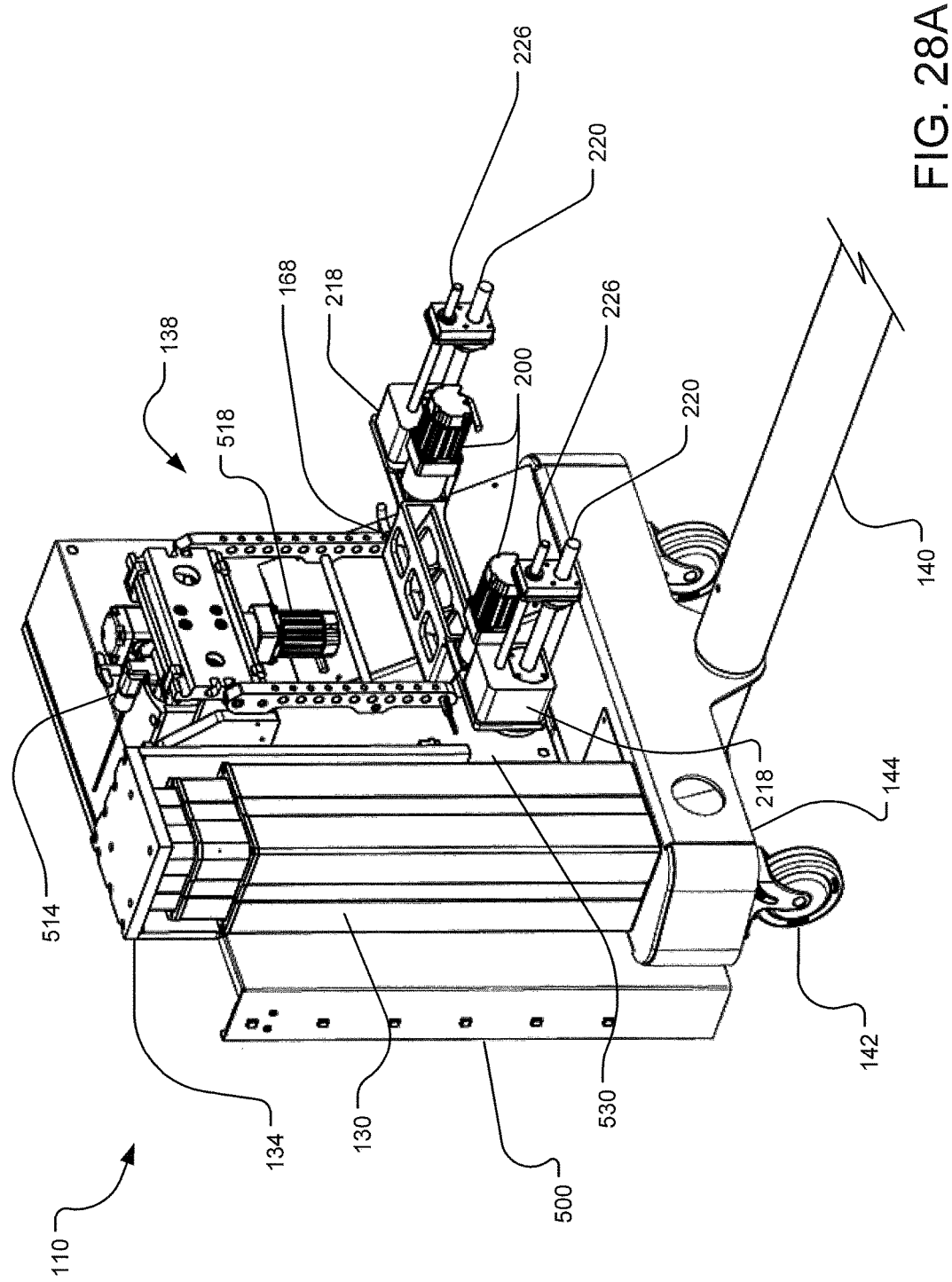
FIGS. 28A and 28B a head end perspective view and a foot end perspective view, respectively, of the foot end of FIG. 27 connected to the driver of the patient support.
Figure 28B:
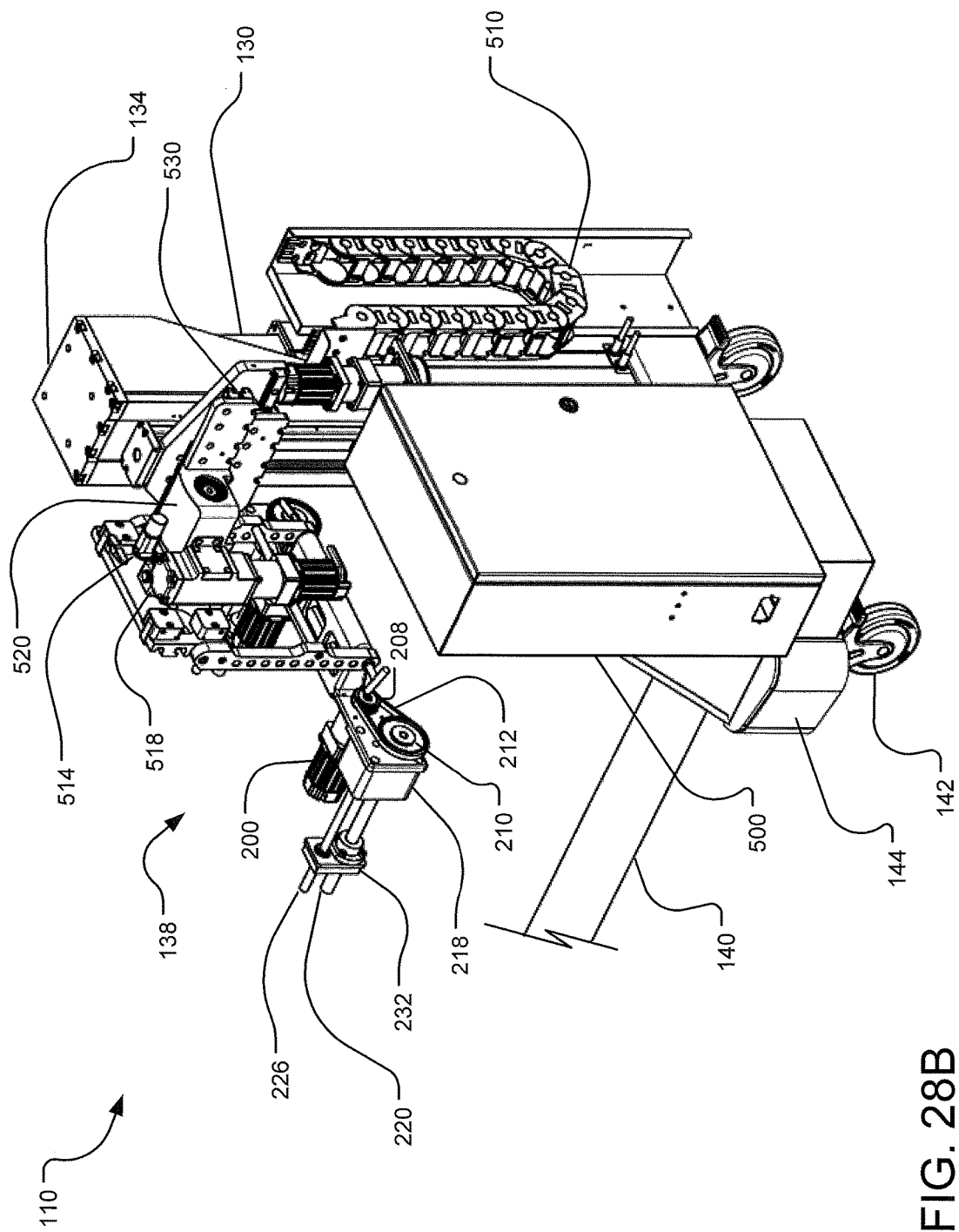

Turning to FIGS. 27 to 28B, a detailed description of the foot end 110 of the base 104 is provided. FIG. 27 shows an exploded view of the foot end 110 of the base 104. FIGS. 28A and 28B show a head end perspective view and a foot end perspective view, respectively, of the foot end 110 connected to the driver 176 of the patient support 106.

In one implementation, the castor 142 is mounted to the moveable base end 144, from which the uprights of the foot end 110 extend, including the linear actuator 130 and the secondary elevator mount assembly 134. As described herein, in one implementation, the linear actuator 130 and secondary elevator mount assembly 134 provide primary and secondary elevator capabilities by vertically translating along a vertical axis through a telescoping motion.

As shown in FIG. 27, an enclosure mount 502 may be mounted to the moveable base end 144 near a control box 500 with mounting gussets 504 and 506 mounted thereto for housing the various electrical components and cables for controlling the operations of the table 100 based on input received via the user interface 126.

In one implementation, a carriage plate 508 is mounted to the foot end, for example, to one of the linear actuator 130 or the secondary elevator mount assembly 134 to secure an energy chain 510. A custom slide 512 is mounted to a roll block 520 and a two stage compensation assembly 530 via a bearing block mount 526 to provide translation compensation, as described herein. The custom slide is connected to the linear actuator 130 and/or the secondary elevator mount assembly 134 using a linear bearing mount 524. The linear actuator 130 and/or the secondary elevator mount assembly 134 may include a home switch bracket 528.

In one implementation, the roll assembly 138 extends through a roll lock assembly 514 having a roll sensor 516 to engage the roll block 520, which provides movement relative to the roll axis as described herein. A roll sensor mount 532 may be provided for receiving the roll sensor 516, which may be used to determine a current orientation of the patient support 106 relative to the roll axis and communicate with the user device 126 to control the operations of the table 100 to provided movement about the roll axis. The roll assembly 138 may be secured to the roll block 520 using a roll shaft end cap 522.

Figure 29A:
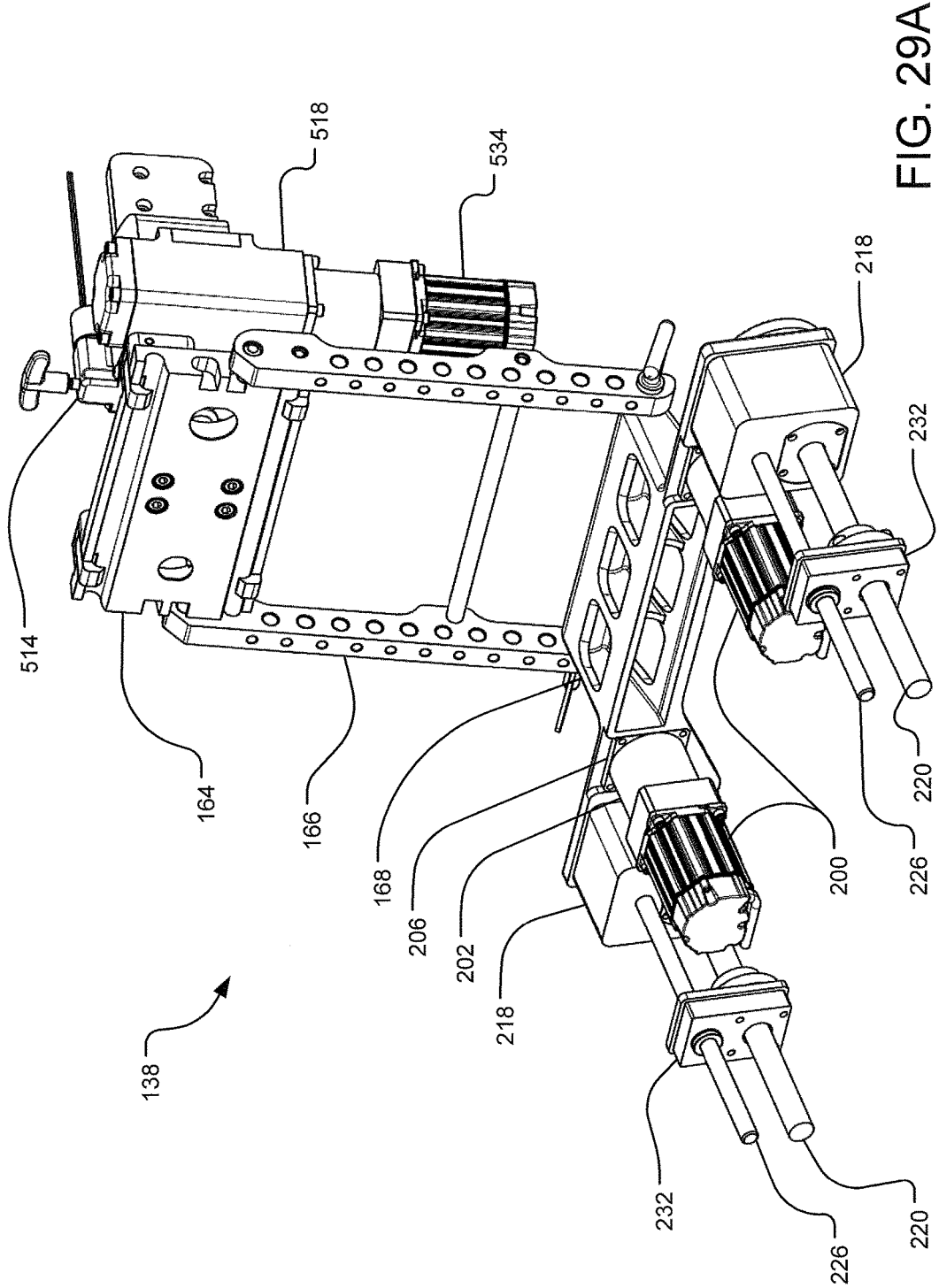
FIGS. 29A and 29B show a head end perspective view and a foot end perspective view, respectively, of a connection assembly of the foot end of FIG. 29A connected to a roll assembly and the driver of the patient support.
Figure 29B:
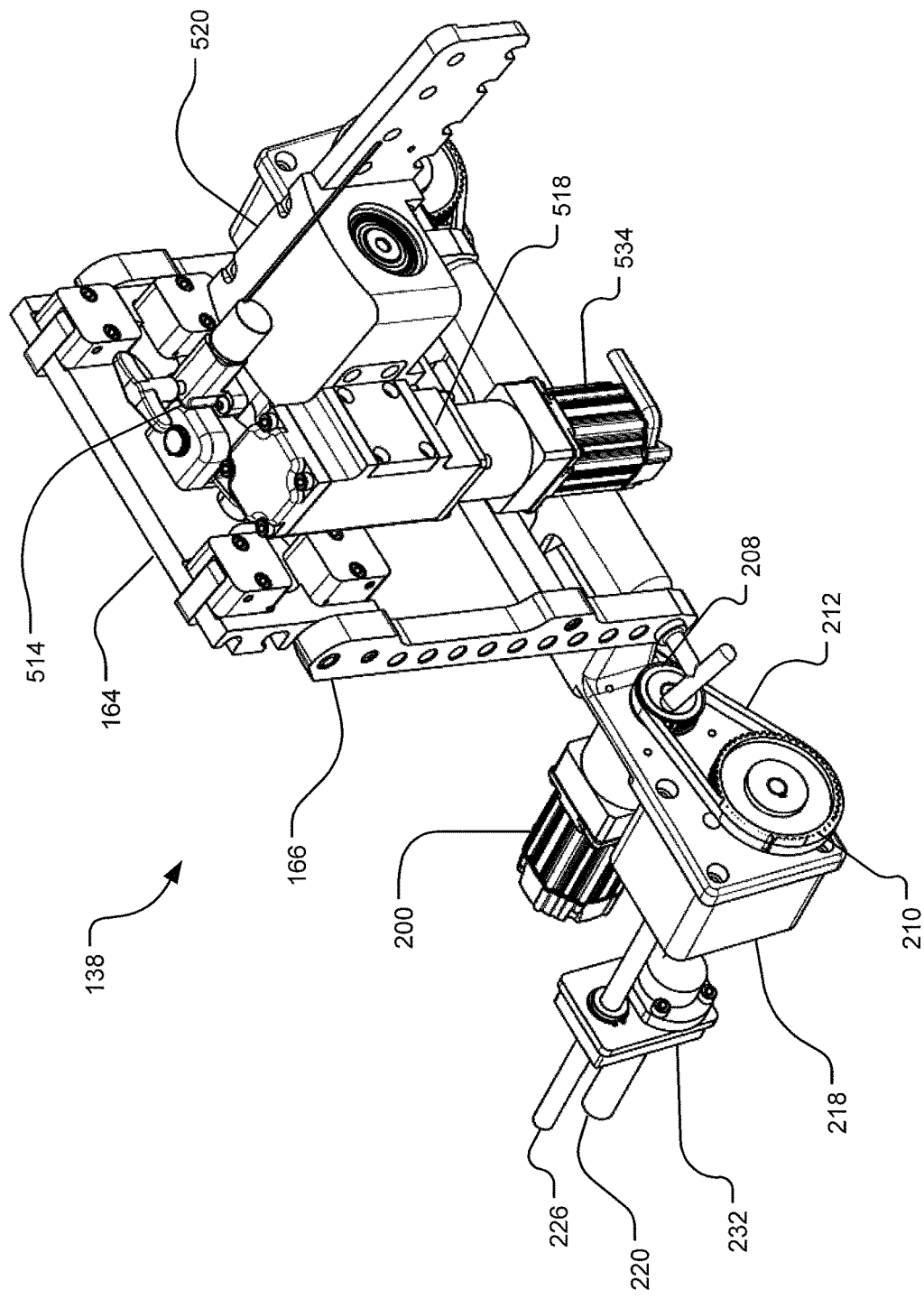

As can be understood from FIGS. 29A to 29B, which are a head end perspective view and a foot end perspective view, respectively, the roll mount assembly 138 is connected to the roll block 520 to provide rotational movement about the rotation axis positioned relative to the bracket 164. In one implementation, a roll motor assembly 518 includes a motor 534 connected to the roll block 520 to provide rotational movement of the roll assembly 138 about the roll axis, which may be positioned relative to the rotation shaft of the bracket 164 as described herein.

Figure 30:
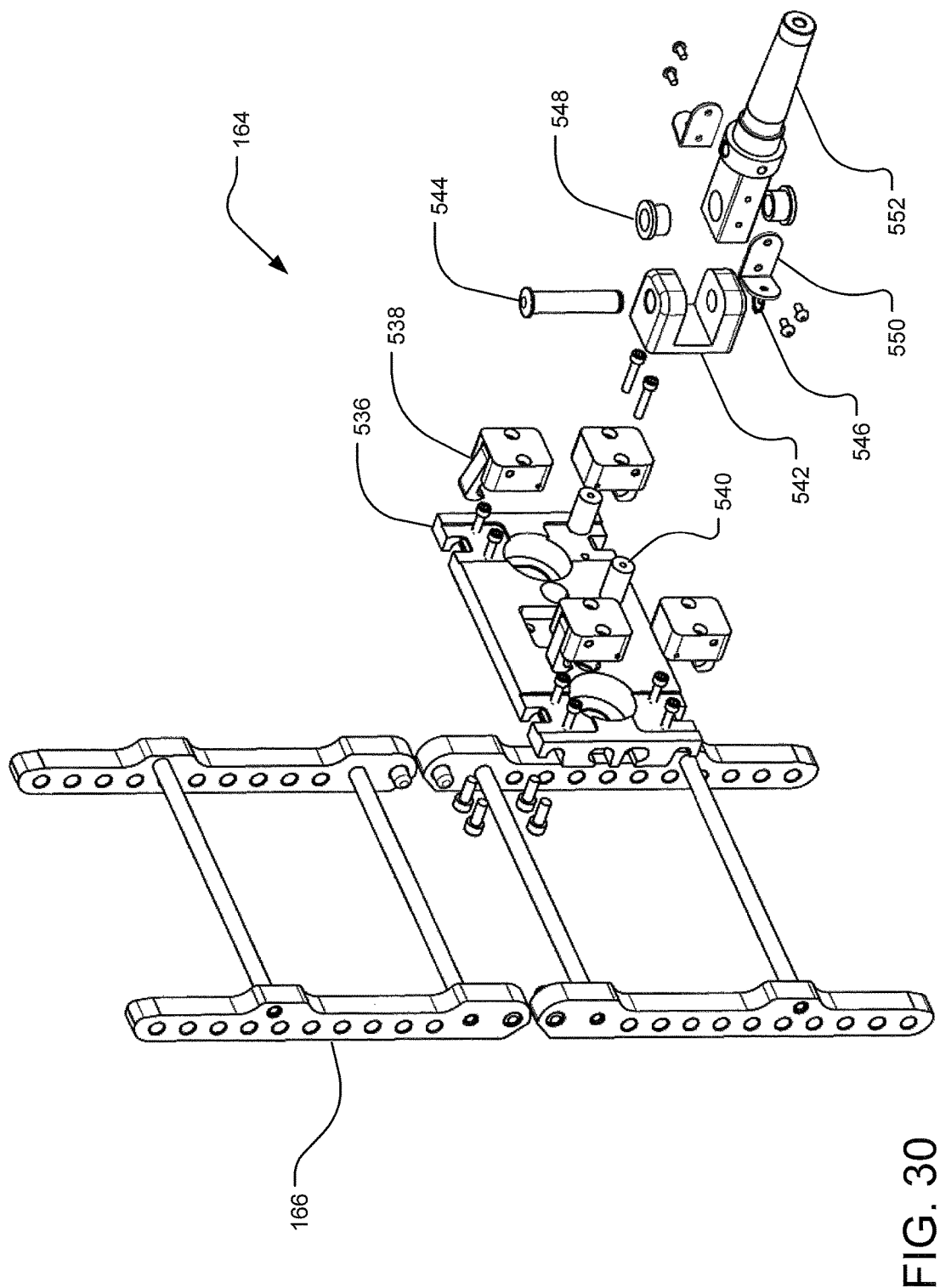
FIG. 30 is an exploded view of the connection assembly.
Figure 31:
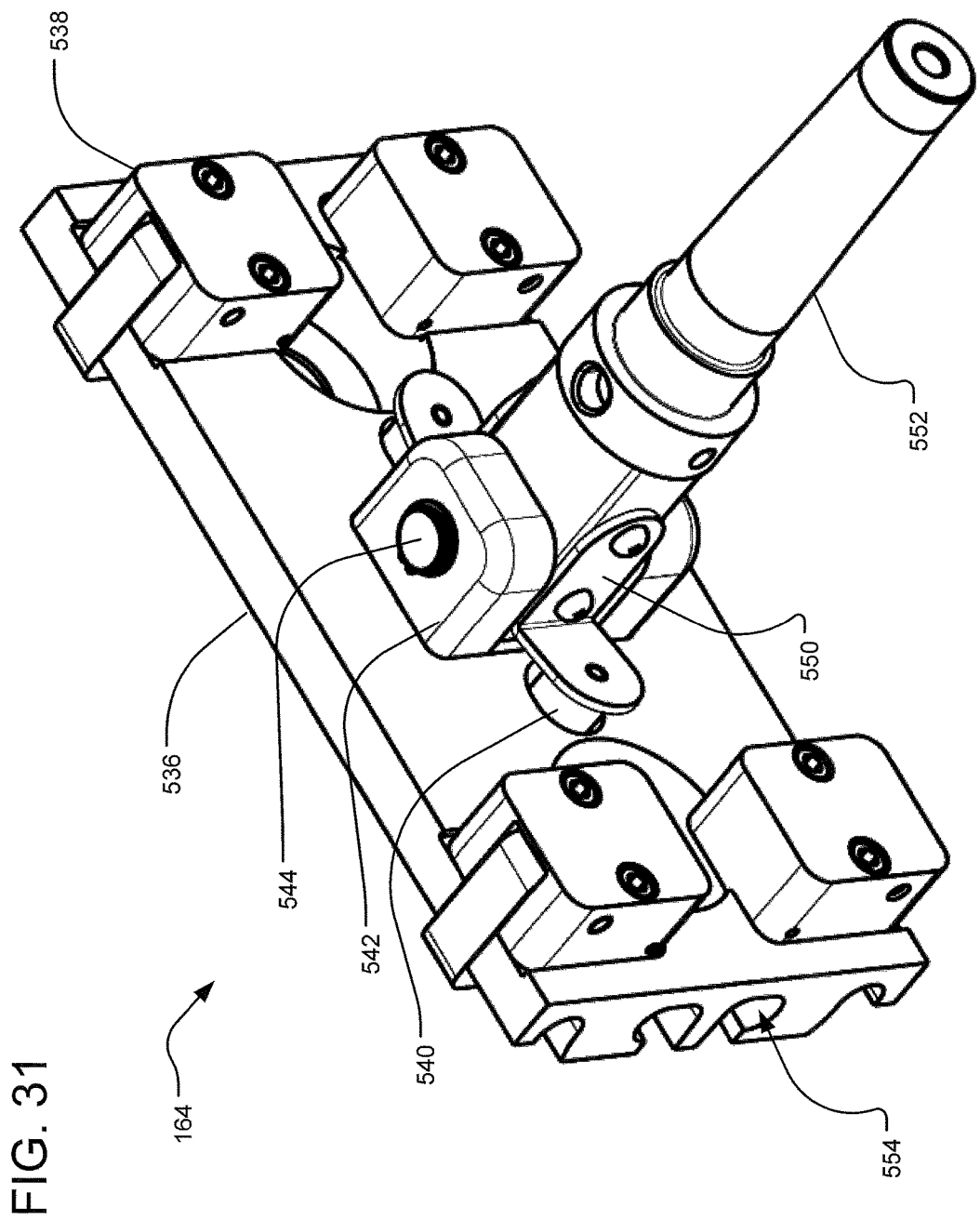
FIG. 31 shows a perspective view of a bracket of the connection assembly of FIG. 30.

Turning to FIGS. 30-31, a detailed description of the foot end roll assembly 138 is provided. It will be appreciated that the head end roll assembly 136 may be substantially similar. In one implementation, the roll assembly 136 includes the frame 166, which may be shaped like an "H" and have one or more ladder rungs extending between and connecting a pair of opposing vertical members. The frame 166 is mounted to the bracket 164 for connection to the roll block 520 and to the driver 176 and patient support 106 as described herein.

In one implementation, the bracket 164 includes a bracket plate 536 having one or more indents 554 to engage the rungs of the frame 166. One or more latches 538 may be mounted to the bracket plate 536 to further facilitate the connection to the frame 166. One or more yaw springs 540 are connected to a respective yaw spring bracket 550 to provide the motion about the yaw axis as detailed herein. In one implementation, a pin block 542 is mounted to the bracket plate 536 using the yaw bracket 550. A head pin 544 is inserted through holes in the pin block 542, a roll shaft 552, one or more flange bushings 548, and a snap ring 546 to mount the roll shaft 552 to the bracket plate 536. As detailed herein, the roll shaft 552 is configured to engage the roll block 520 to provide rotational movement of the roll assembly 138 and thus the patient support 106 about the roll axis. In one implementation, the roll axis extends longitudinally through the roll shaft 552.

Figure 32:
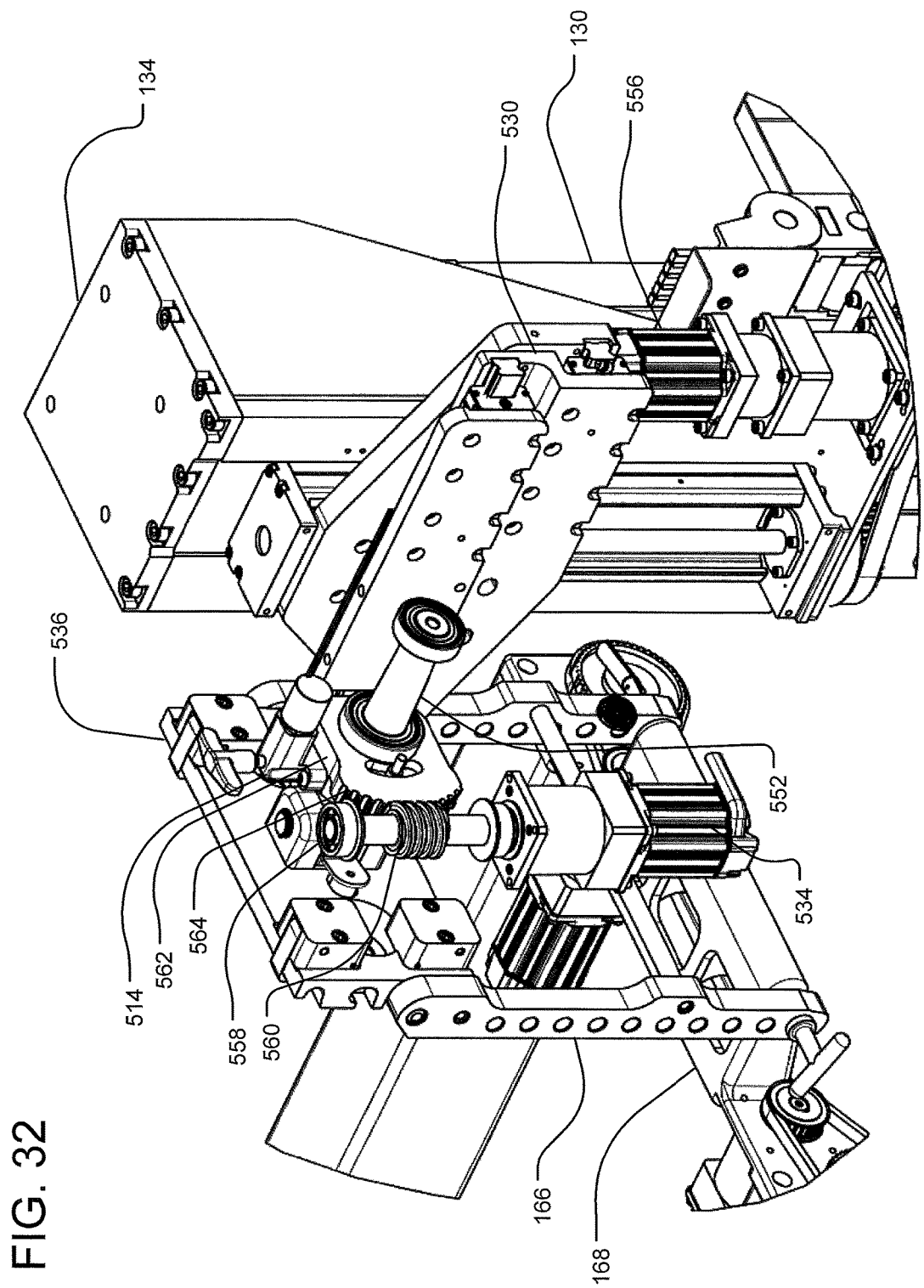
FIG. 32 shows a detailed view of the foot end of FIG. 28B with the housings of roll block assembly and roll motor assembly removed.

To provide a detailed description of the interaction of the roll block 520 with the roll motor assembly 518 and the roll assembly 138, FIG. 32 shows a detailed view of the foot end 100 with the housings of the roll block 520 and the roll motor assembly 518 removed. As can be understood from FIG. 32, the roll motor assembly 518 includes a stationary screw 558 with threaded features 560 configured to engage a gear 562 having corresponding features 558. The roll shaft 552 extends through the gear 562, such that when the motor 534 of the roll motor shaft assembly 518 drives the screw 558, the threaded features 560 turn the gear 562, thereby rotating the roll shaft 552. In one implementation, the gear 562 includes a channel through which at least a portion of the roll lock assembly 514 may extend to lock the roll assembly 138 into position and prevent further rotational movement.

Figure 33:
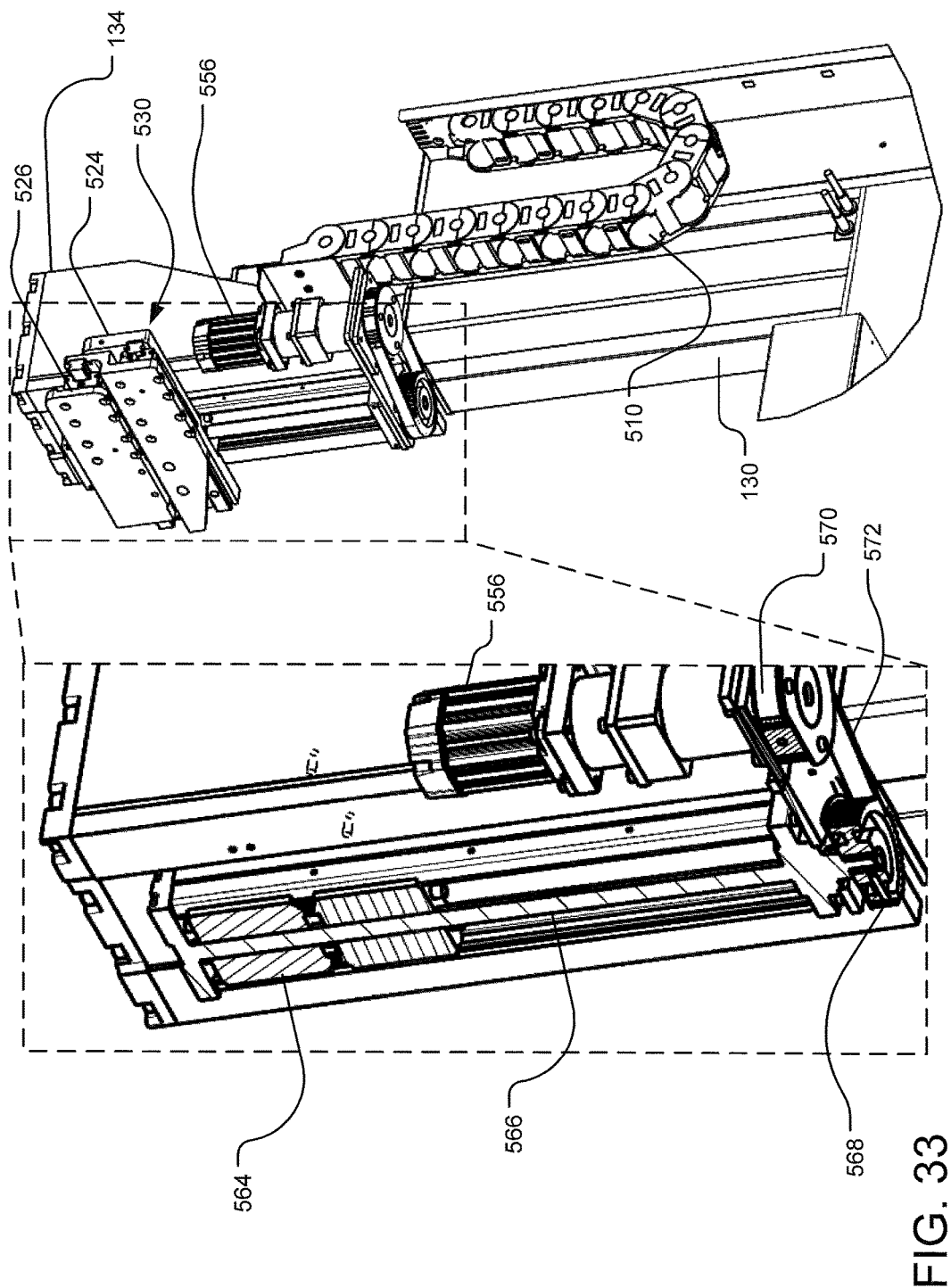
FIG. 33 shows a detailed view and a cross sectional view of a two stage compensation assembly of the foot end of FIG. 28B.

Turning to FIG. 33, a detailed view and a cross sectional view of the slide 512 and the two stage compensation assembly 530 are shown. In one implementation, a motor 556 is connected to a first pulley 570 to provide rotational translation, which is provided to a second pulley 568 via a drive belt 572. The second pulley 568 rotates a shaft 566 extending through slide members 564, thereby providing linear translation compensation as detailed herein.

Figure 34:
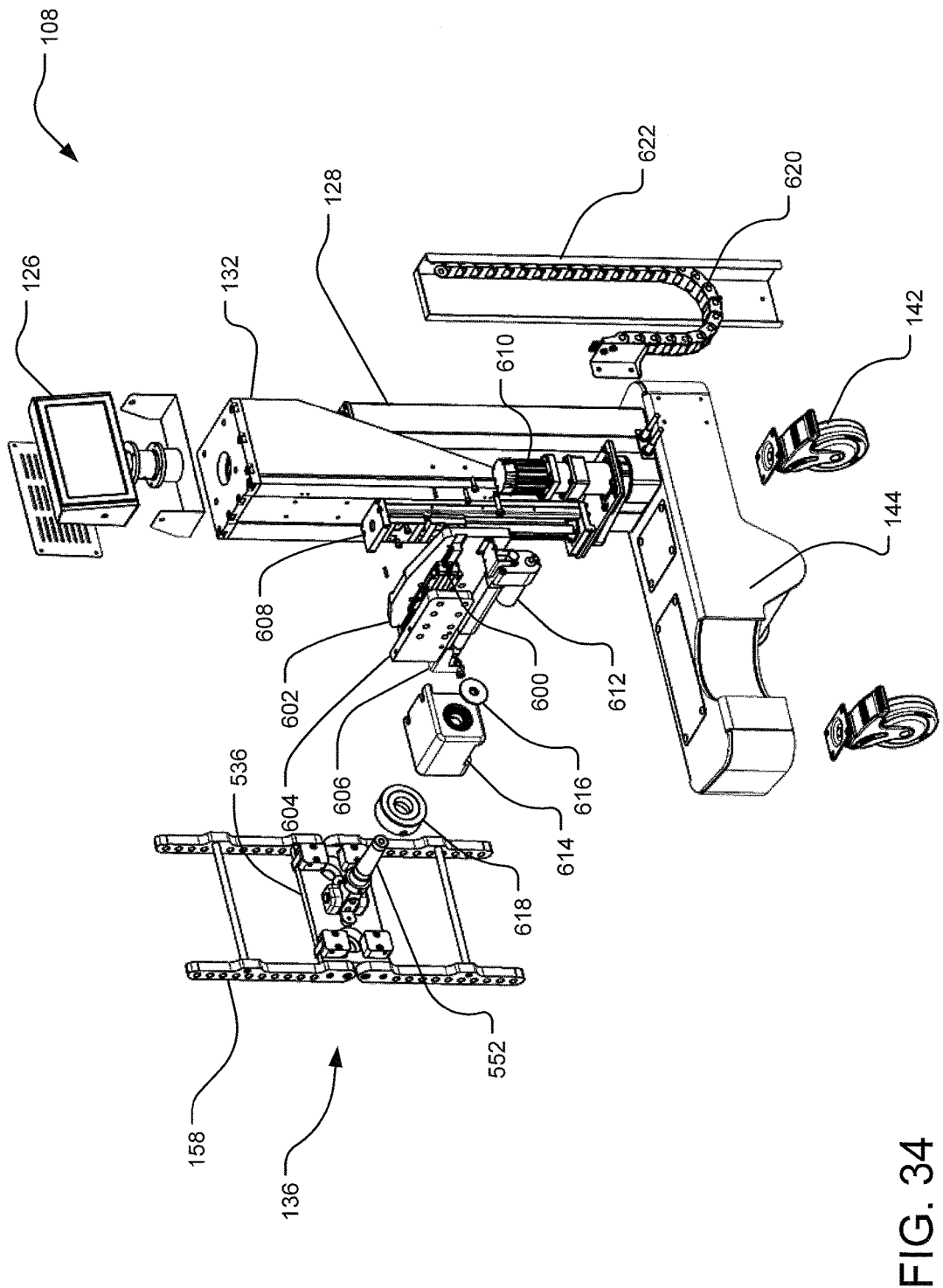
FIG. 34 illustrates an exploded view of the head end of the base.
Figure 35A:
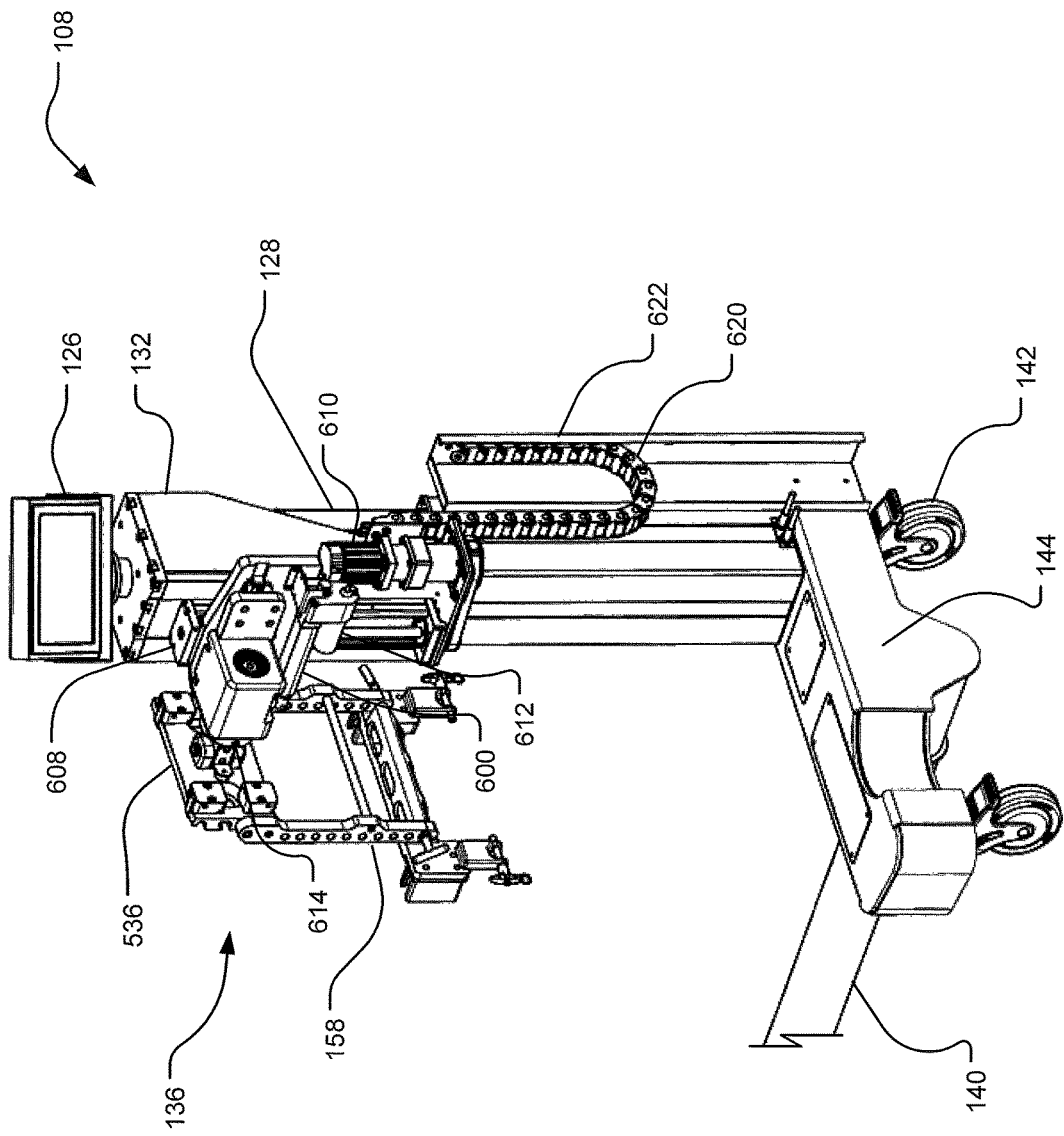
FIGS. 35A and 35B show a head end perspective view and a foot end perspective view, respectively, of the head end of FIG. 34.
Figure 35B:
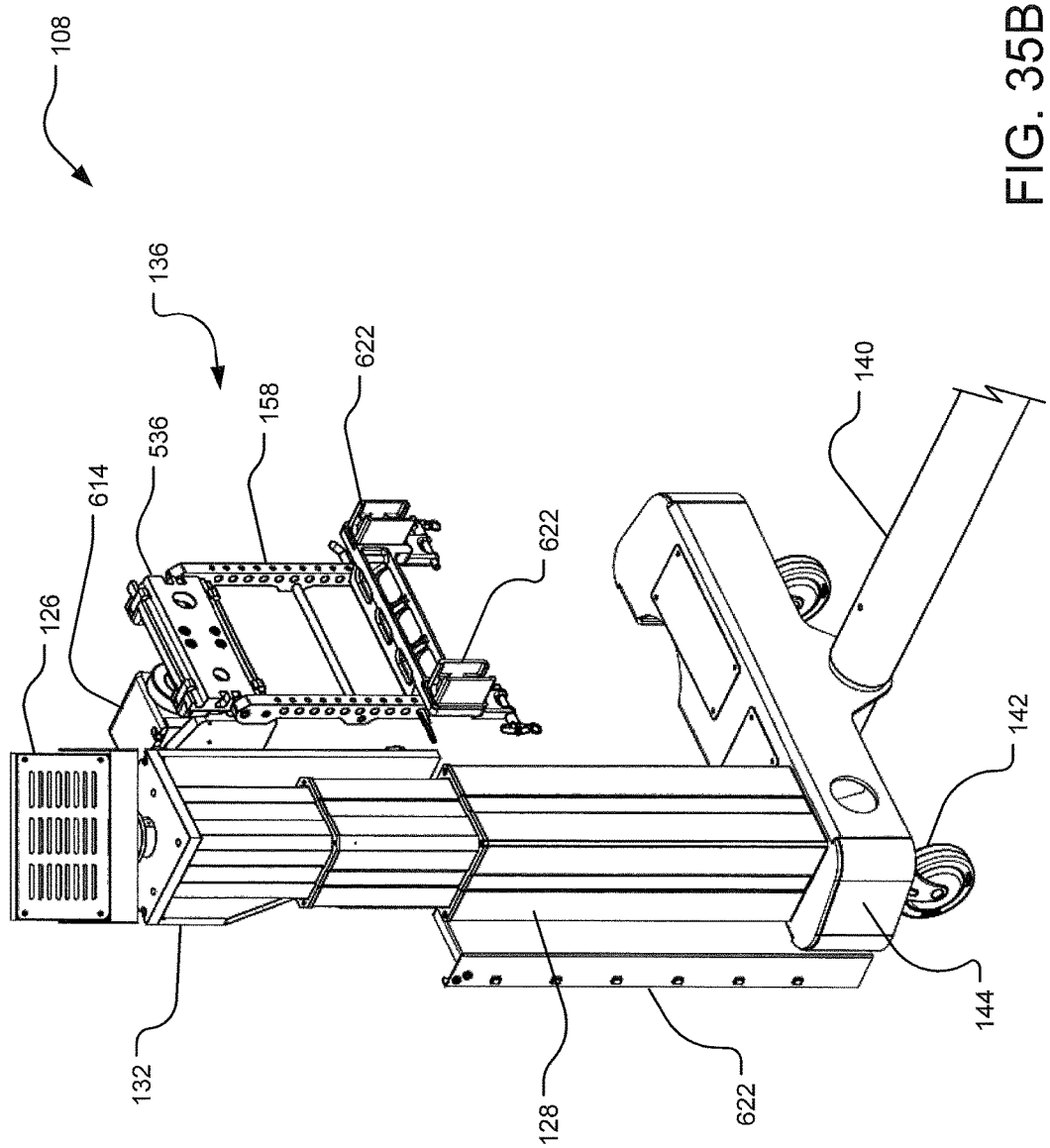

For a detailed description of the head end 108 of the base 104, reference is made to FIGS. 34 to 35B. FIG. 34 illustrates an exploded view of the head end 108 of the base 104, and FIGS. 35A and 35B show a head end perspective view and a foot end perspective view, respectively, of the head end 108.

In one implementation, the castor 142 is mounted to the moveable base end 144, from which the uprights of the head end 108 extend, including the linear actuator 128 and the secondary elevator mount assembly 132. As described herein, in one implementation, the linear actuator 128 and secondary elevator mount assembly 132 provide primary and secondary elevator capabilities by vertically translating along a vertical axis through a telescoping motion. The user device 126 is mounted to the secondary elevator mount assembly 132 for easy access by a user to control the table 100.

As can be understood from FIGS. 34 to 35B, the head end 108 includes a linear guide 600 for providing linear translation compensation via an actuator 612 and a slide 608 as detailed herein. In one implementation, the actuator 612 is mounted using an actuator mount 606, and the linear guide 600 is mounted to the linear actuator 128 and/or the secondary elevator mount assembly 132 using a linear bearing mount 602 and to a roll block 614 using a bearing block mount 604. A motor 610 is configured to provide the linear translation similar to the motor 556 as described with respect to FIG. 33. In one implementation, the roll block 614 is configured to receive and secure the roll shaft 552 using a roll damper assembly 618 and a roll shaft end cap 616 to maintain the roll axis relative to the roll shaft 552 of the foot end 110.

In one implementation, a lateral translation compensation subassembly is positioned at the head end 108. The lateral translation compensation subassembly includes a drive mount plate 168 with translation brackets 622 connected to the right and left head end frames 114 and configured to telescope outwardly and inwardly from the head end frames 114 to lengthen and shorten the head end frames 114 when the patient support 106 is moved to various positions. The lateral translation compensation subassembly also includes a translation driver disposed within or next to the head end frames 114 and configured to actuate the telescoping of the translation brackets 622.

Figure 36A:
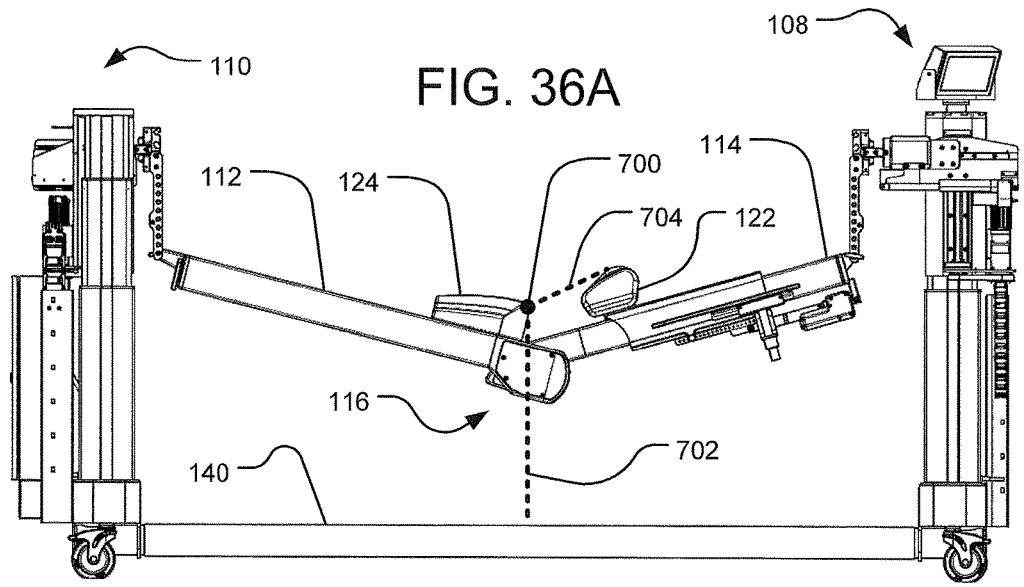
FIGS. 36A-C shows side views of the surgical table in the extension position, the neutral position, and the flexion position, respectively.
Figure 36B:
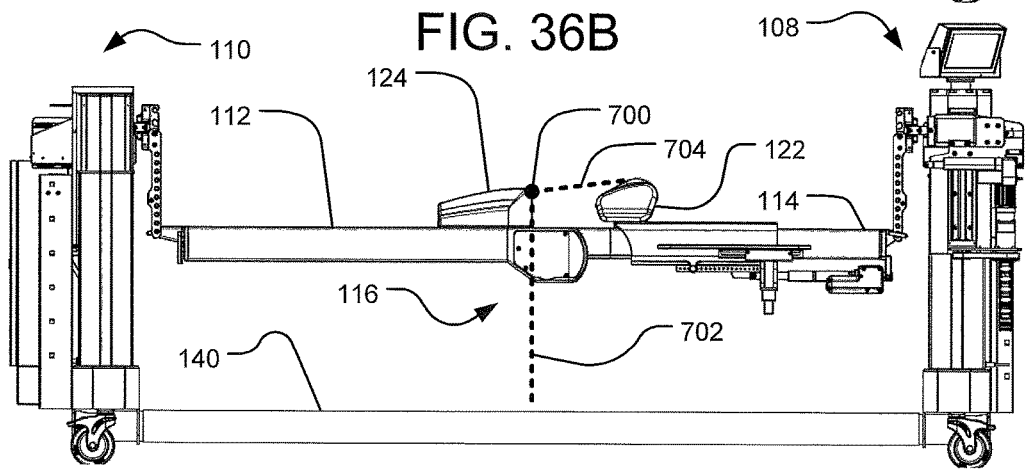
Figure 36C:
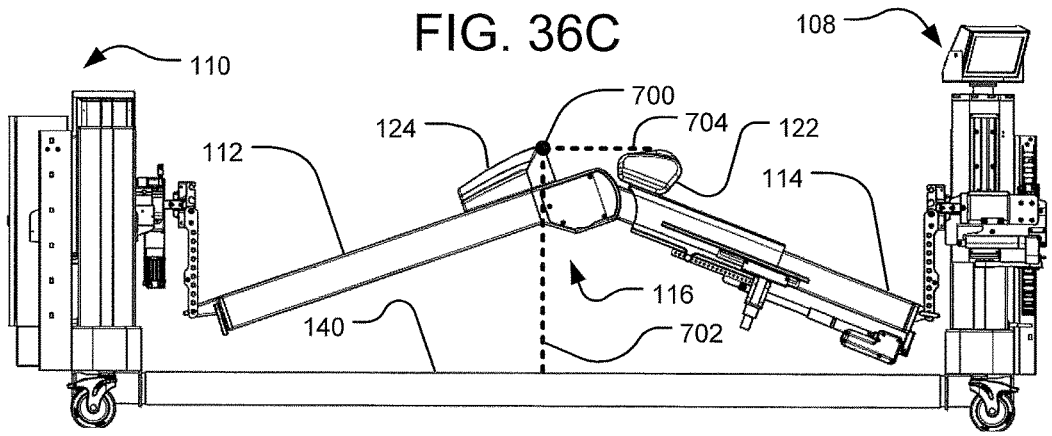

Turning to FIGS. 36A-C side views of the surgical table 100 in the extension position, the neutral position, and the flexion position, respectively, are shown.

In one implementation, the surgical table 100 is configured to articulate to various positions while keeping the surgical field stationary. Stated differently, virtual pivot points 700 positioned on the hip pads 124 at the point of contact with the patient skin are intersected by the first pitch axis and remain stationary while the surgical table 100 moves around them. The virtual pivot points 700 have a height 702 above the base frame member 140 that is substantially constant throughout movement of the table 100 to the various illustrated in FIGS. 36A-C.

Referring to FIG. 36B, in one implementation, when the patient support 106 is positioned with the hinges 116 in the neutral position, such that neither the spine nor hips of the patient 102 are flexed or extended, the virtual pivot point 700 is located at a selected height 702 from the base frame member 140 or the floor. The selected height 702 may be determined based on convenience or comfort for the medical personnel performing the medical procedure on the patient 102. For example, the selected height may be approximately 48 inches.

Turning to FIG. 36A, when the hinges 116 are actuated from the neutral position to the extension position, extending the hips and spine of the patient 102, the selected height 702 of the virtual pivot points 700 remains substantially unchanged. Similarly, referring to FIG. 36C, when the hinges 116 are actuated from the neutral position to the flexion position, flexing the hips and spine of the patient 102, the selected height 702 of the virtual pivot points 700 remains substantially unchanged.

To keep the virtual pivot points 700 stationary and the height 702 unchanged during the articulation of the table 100 between the extension, neutral, and flexion positions, the overall length of the patient support 106 and/or the orientations of the various components of the head end 108 and the foot end 110 may change to compensate for the movement of the patient support 106 as described herein. Stated differently, because the base 104 is fixed in position by the base frame member 140, such that the movable base ends 144 are fixed relative to each other, a change in a height in one or both of the linear actuators 128, 130 and/or the secondary elevator mount assemblies 132, 134 changes the length of the patient support 106 a complementary amount using various components providing lateral translation compensation a described herein.

Thus, as can be understood from FIGS. 36A-C, in one implementation, when articulating to the extension position, the primary and secondary elevators 130, 134 of the foot end 110 and the primary and secondary elevators 128, 132 of the head end 108 of the base 104 move vertically upwards from the base frame member 140 while the actuator in the head end 108 extends the head end frame 114. When articulating to the flexion position, the linear actuators 128, 130 and the secondary elevator mount assemblies 132, 134 of the foot end 110 and the head end 108 of the base 104 move vertically downwards towards the base frame member 140 while the actuator in the head end 108 moves for active linear translation compensation. In other words, the head end 108 and the foot end 110 are fixed relative to each other, so as the patient support articulates between extension, flexion, and neutral, the overall length of the patient support 106 changes and the vertical translation of the head end 108 and the foot end 110 changes.

Similarly, when the patient 102 is initially positioned on the patient support 106, the trunk translator 118 is set for a torso length of the individual patient 106 and locked into place. Stated differently, the patient 102 is positioned with the pelvis on the hip pads 124, and the trunk translator 118 is moved to position the sternum of the patient 102 on the chest pad 122. The trunk translator 118 is then locked into this position with a distance 704 between the hips pads 124 and the chest pad 122. As the table moves to various positions, for example, during flexion and extension articulation, the user device 126 adjusts the position of the trunk translator 118 to keep the distance 704 between the hip pads 124 and the chest pad 122 substantially constant. The constant distance 704 between the pads 122 and 124 prevents distraction and compression of the spine and sheering of the skin of the patient 102 during movement.

FIG. 37 illustrates example operations 800 for articulating a patient support in a surgical table. In one implementation, an operation 802 receives input from a user, such as medical personnel, using a computing device, which may be a user device generating a graphical user interface. The input defines an adjustment to an access angle of a surgical field. An operation 804 articulates a patient support based on the input using a base. The articulation including various motions, as detailed herein, such as moving about one or more pitch axes to and from a neutral position, an extension position, or a flexion position or moving about one or more roll, vertical, and yaw axes. A point area, such as a virtual pivot point, on each of a pair of hip support pads remains stationary during the articulation to keep the surgical field stable during the adjustment to the access angle.

Figure 38:
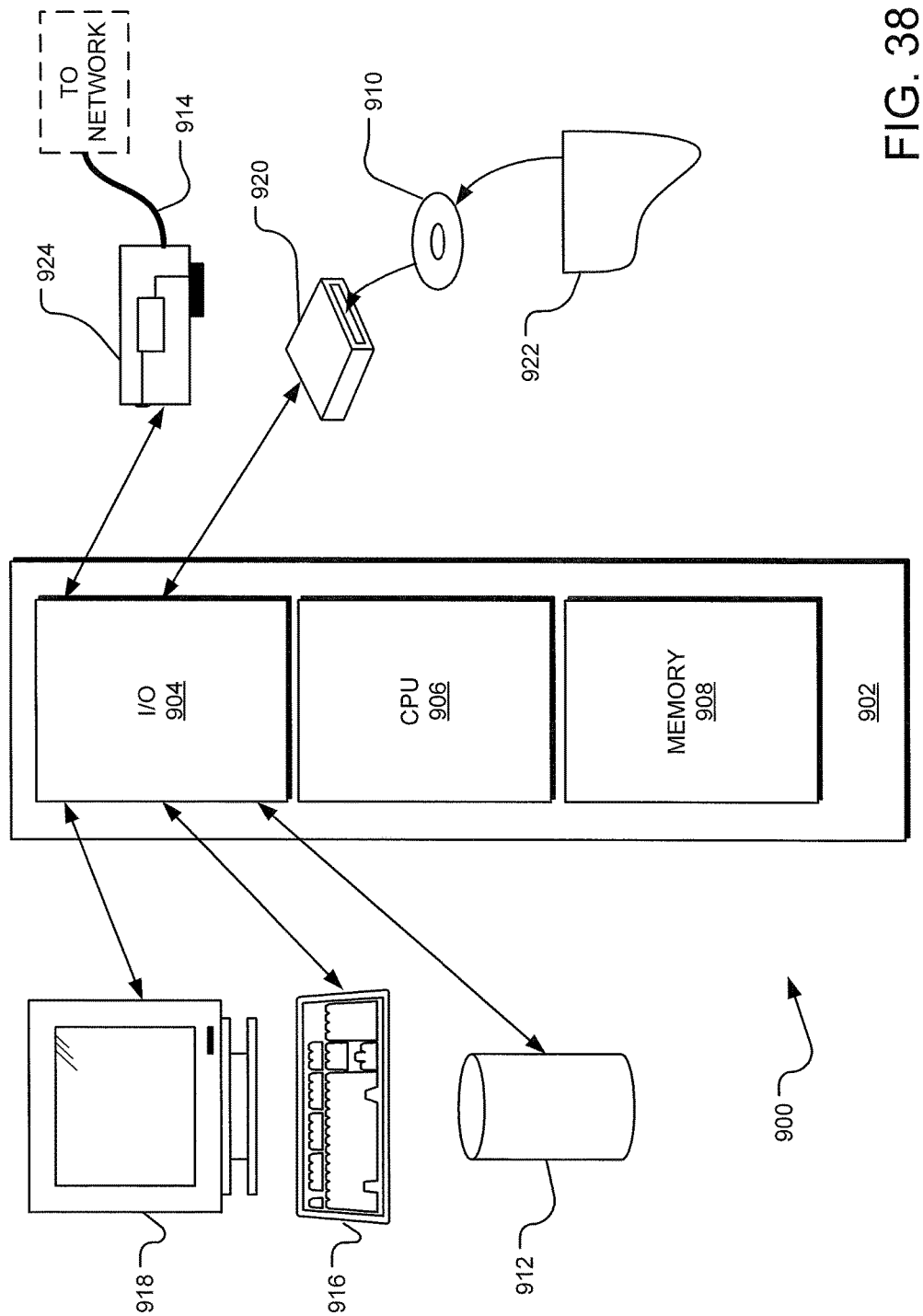
FIG. 38 is an example computing system that may be specifically configured to implement the various systems and methods discussed herein.

Referring to FIG. 38, a detailed description of an example computing system 900 having one or more computing units that may implement various systems and methods discussed herein is provided. The computing system 900 may be applicable to the user device 126, a server in communication with a network, or other computing devices. It will be appreciated that specific implementations of these devices may be of differing possible specific computing architectures not all of which are specifically discussed herein but will be understood by those of ordinary skill in the art.

The computer system 900 may be a general computing system is capable of executing a computer program product to perform a computer process. Data and program files may be input to the computer system 900, which reads the files and executes the programs therein. Some of the elements of a general purpose computer system 900 are shown in FIG. 38 wherein a processor 902 is shown having an input/output (I/O) section 904, a Central Processing Unit (CPU) 906, and a memory section 908. There may be one or more processors 902, such that the processor 902 of the computer system 900 comprises a single central-processing unit 906, or a plurality of processing units, commonly referred to as a parallel processing environment. The computer system 900 may be a conventional computer, a distributed computer, or any other type of computer, such as one or more external computers made available via a cloud computing architecture. The presently described technology is optionally implemented in software devices loaded in memory 908, stored on a configured DVD/CD-ROM 910 or storage unit 912, and/or communicated via a wired or wireless network link 914, thereby transforming the computer system 900 in FIG. 38 to a special purpose machine for implementing the described operations.

The I/O section 904 is connected to one or more user-interface devices (e.g., a keyboard 916 and a display unit 918), a disc storage unit 912, and a disc drive unit 920. In the case of a tablet, a smart phone device, or similar computing device, there may not be a physical keyboard but rather a touch screen with a computer generated touch screen keyboard. Generally, the disc drive unit 920 is a DVD/CD-ROM drive unit capable of reading the DVD/CD-ROM medium 910, which typically contains programs and data 922. Computer program products containing mechanisms to effectuate the systems and methods in accordance with the presently described technology may reside in the memory section 904, on a disc storage unit 912, on the DVD/CD-ROM medium 910 of the computer system 900, or on external storage devices made available via a cloud computing architecture with such computer program products, including one or more database management products, web server products, application server products, and/or other additional software components. Alternatively, a disc drive unit 920 may be replaced or supplemented by an optical drive unit, a flash drive unit, magnetic drive unit, or other storage medium drive unit. Similarly, the disc drive unit 920 may be replaced or supplemented with random access memory (RAM), magnetic memory, optical memory, and/or various other possible forms of semiconductor based memories.

The network adapter 924 is capable of connecting the computer system 900 to a network via the network link 914, through which the computer system can receive instructions and data. Examples of such systems include personal computers, Intel or PowerPC-based computing systems, AMD-based computing systems and other systems running a Windows-based, a UNIX-based, or other operating system. It should be understood that computing systems may also embody devices such as terminals, workstations, personal computers, mobile phones, tablets or slates, multimedia consoles, gaming consoles, set top boxes, etc.

When used in a LAN-networking environment, the computer system 900 is connected (by wired connection or wirelessly) to a local network through the network interface or adapter 924, which is one type of communications device. When used in a WAN-networking environment, the computer system 900 typically includes a modem, a network adapter, or any other type of communications device for establishing communications over the wide area network. In a networked environment, program modules depicted relative to the computer system 900 or portions thereof, may be stored in a remote memory storage device. It is appreciated that the network connections shown are examples of communications devices for and other means of establishing a communications link between the computers may be used.

In an example implementation, table articulation data, imaging data, patient data, a plurality of internal and external databases, source databases, and/or cached data on servers are stored as the memory 908 or other storage systems, such as the disk storage unit 912 or the DVD/CD-ROM medium 910, and/or other external storage devices made available and accessible via a network architecture. Table articulation software, imaging software, and other modules and services may be embodied by instructions stored on such storage systems and executed by the processor 902.

Some or all of the operations described herein may be performed by the processor 902. Further, local computing systems, remote data sources and/or services, and other associated logic represent firmware, hardware, and/or software configured to control operations of the table 100, the user device 126, and/or other computing units or components in communication with the table 100 and/or the user device 126. Such services may be implemented using a general purpose computer and specialized software (such as a server executing service software), a special purpose computing system and specialized software (such as a mobile device or network appliance executing service software), or other computing configurations. In addition, one or more functionalities disclosed herein may be generated by the processor 902 and a user may interact with a Graphical User Interface (GUI) using one or more user-interface devices (e.g., the keyboard 916, the display unit 918, and the user device 126). The system set forth in FIG. 38 is but one possible example of a computer system that may employ or be configured in accordance with aspects of the present disclosure.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to, magnetic storage medium (e.g., floppy diskette), optical storage medium (e.g., CD-ROM); magneto-optical storage medium, read only memory (ROM); random access memory (RAM); erasable programmable memory (e.g., EPROM and EEPROM); flash memory; or other types of medium suitable for storing electronic instructions.

The description above includes example systems, methods, techniques, instruction sequences, and/or computer program products that embody techniques of the present disclosure. However, it is understood that the described disclosure may be practiced without these specific details.

Although various representative implementations have been described above with a certain degree of particularity, those skilled in the art could make numerous alterations to the disclosed embodiments without departing from the spirit or scope of the inventive subject matter set forth in the specification. All directional references (e.g., distal, proximal, front, back, side, top, bottom, fore, aft, right, left, etc.) are only used for identification purposes to aid the reader's understanding of the implementations, and do not create limitations, particularly as to the position, orientation, or use of the invention unless specifically set forth in the claims. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

While the present disclosure has been described with reference to various embodiments, it will be understood that these embodiments are illustrative and that the scope of the disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A surgical table comprising:
a patient support including a first end section comprising a pair of first end frames joined with a second end section comprising a pair of second end frames, the first end section is inwardly joined with the second end section at a pair of hinges constructed of radiolucent material, said hinges being located between the first end frames and the respective second end frames, wherein the hinges are actively driven to cause the first end section to articulate relative to the second end section, wherein each of the pair of hinges comprises a sprocket, a driver, and a drive chain positioned within the second end frame, the drive chain coupled at one end to the sprocket and at the opposite end to the driver, the sprocket being rotatably coupled with the first end frame via a hinge pin, the drive chain being moved in compression by the driver to cause the sprocket to rotate such that the first end section articulates relative to the second end section about the hinge pin.

2. The surgical table of claim 1, wherein the drive chain comprises a plurality of drive links coupled together, the driver operably coupled with a motor configured to move the driver within the second end frame.

3. The surgical table of claim 2, wherein the driver is longitudinally translated within the second end frame via a linear screw and nut.

4. The surgical table of claim 2, wherein the first end section is a head end section and the pair of first end frames is a pair of head end frames, wherein the second end section is a foot end section and the pair of second end frames is a pair of foot end frames.

5. The surgical table of claim 4, wherein the sprocket is positioned within a cavity of a housing at an inner end of the foot end frames, the sprocket including a sprocket head end surface and a sprocket foot end surface, the cavity including a cavity head end surface and a cavity foot end surface, the sprocket configured to rotate within the cavity about the hinge pin a certain angle between the cavity head end surface and the cavity foot end surface.

6. The surgical table of claim 5, wherein the certain angle is up to seventy degrees.

7. The surgical table of claim 5, wherein the sprocket rotates toward the head end surface up to forty degrees from a position where the first end section is aligned with the second end section along a longitudinal axis of the patient support to another position where the patient support is articulated into flexion.

8. The surgical table of claim 5, wherein the sprocket rotates toward the foot end surface up to thirty degrees from a position where the first end section is aligned with the second end section along a longitudinal axis of the patient support to another positioner where the patient support is articulated into extension.

9. The surgical table of claim 2, wherein the sprocket is a faceted sprocket including a plurality of facet surfaces configured to maintain alignment of the plurality of drive links as the drive chain causes the sprocket to rotate.

10. The surgical table of claim 9, wherein a planar portion of the plurality of drive links is configured to contact at least some of the plurality of facet surfaces as the sprocket rotates.

11. The surgical table of claim 9, wherein alignment of the plurality of drive links is maintained by at least some of the plurality of drive links being sandwiched between at least some of the plurality of facet surfaces and an inner top wall of a cavity of a housing surrounding the sprocket.

12. The surgical table of claim 2, wherein each of the plurality of drive links includes a body having protrusions and indents that matingly engage with corresponding indents and protrusions of neighboring drive links.

13. The surgical table of claim 12, wherein pairs of the plurality of drive links are coupled together via a drive link pin.

14. The surgical table of claim 2, wherein the hinges are made of a radiolucent material.

15. The surgical table of claim 1, further comprising a base comprising a pair of opposed end supports operably coupled with outer ends of the patient support, at least one of the end supports comprising a roll assembly configured to rotate the patient support about a roll axis.

* * * * *